United States Patent
Klinghoffer et al.

(10) Patent No.: US 12,121,508 B2
(45) Date of Patent: *Oct. 22, 2024

(54) PHARMACEUTICAL COMBINATIONS FOR THE TREATMENT OF CANCER

(71) Applicant: Presage Biosciences, Inc., Seattle, WA (US)

(72) Inventors: Richard Klinghoffer, Seattle, WA (US); Joyoti Dey, Shoreline, WA (US)

(73) Assignee: Presage Biosciences, Inc., Seattle, WA (US)

( * ) Notice: Subject to any disclaimer, the term of this patent is extended or adjusted under 35 U.S.C. 154(b) by 174 days.

This patent is subject to a terminal disclaimer.

(21) Appl. No.: 17/371,774

(22) Filed: Jul. 9, 2021

(65) Prior Publication Data

US 2022/0023261 A1     Jan. 27, 2022

Related U.S. Application Data

(63) Continuation of application No. 16/089,276, filed as application No. PCT/US2017/024618 on Mar. 28, 2017, now Pat. No. 11,135,198.

(60) Provisional application No. 62/314,356, filed on Mar. 28, 2016.

(51) Int. Cl.

| | |
|---|---|
| *A61K 31/4025* | (2006.01) |
| *A61K 9/00* | (2006.01) |
| *A61K 31/407* | (2006.01) |
| *A61K 31/453* | (2006.01) |
| *A61K 31/519* | (2006.01) |
| *A61K 31/635* | (2006.01) |
| *A61K 31/69* | (2006.01) |
| *A61K 31/7072* | (2006.01) |
| *A61K 45/06* | (2006.01) |
| *A61K 47/06* | (2006.01) |
| *A61P 35/02* | (2006.01) |

(52) U.S. Cl.
CPC ........ *A61K 31/4025* (2013.01); *A61K 9/0019* (2013.01); *A61K 31/407* (2013.01); *A61K 31/453* (2013.01); *A61K 31/519* (2013.01); *A61K 31/635* (2013.01); *A61K 31/69* (2013.01); *A61K 31/7072* (2013.01); *A61K 45/06* (2013.01); *A61K 47/06* (2013.01); *A61P 35/02* (2018.01)

(58) Field of Classification Search
CPC .............. A61K 31/4025; A61K 31/453; A61K 31/635; A61K 45/06; A61K 31/407; A61K 31/7072; A61K 31/519; A61K 31/69; A61K 35/0019; A61K 47/06; A61P 35/102

See application file for complete search history.

(56) References Cited

U.S. PATENT DOCUMENTS

| | | |
|---|---|---|
| 8,563,596 B2 | 10/2013 | Sivakumar |
| 2009/0142337 A1 | 6/2009 | Squires |
| 2013/0237582 A1 | 9/2013 | Rathos et al. |
| 2014/0080838 A1 | 3/2014 | Wendel et al. |
| 2016/0222012 A1 | 8/2016 | Ruan |

FOREIGN PATENT DOCUMENTS

| | | |
|---|---|---|
| CA | 2219867 A1 | 4/1999 |
| WO | 2007148158 A1 | 12/2007 |
| WO | 2008139271 A2 | 11/2008 |
| WO | 2009/061345 A3 | 5/2009 |
| WO | 2009061345 A2 | 5/2009 |
| WO | 2012164497 A1 | 12/2012 |
| WO | 2015084892 A1 | 6/2015 |
| WO | 2015130585 A1 | 9/2015 |
| WO | 2015181737 A1 | 12/2015 |
| WO | 2016024230 A1 | 2/2016 |

OTHER PUBLICATIONS

Office Action for Chinese Patent Application No. 201780032783.3 dated Jan. 12, 2022, 16 pages.
Office Action for Mexican Patent Application No. 2018/011666 dated May 27, 2021, 7 pages.
Office Action for Russian Patent Application No. 2020121147 dated Sep. 8, 2020, 3 pages.
Translation of Hearing Notice for Indian Patent Application No. 201817039382 dated Aug. 4, 2021, 2 pages.
Office Action for Japanese Patent Application No. 2018-550790 mailed Aug. 30, 2021, 6 pages.
Translation of Office Action for Korean Patent Application No. 10-2021-7021031 dated Sep. 3, 2021, 6 pages.

(Continued)

*Primary Examiner* — Shirley V Gembeh
(74) *Attorney, Agent, or Firm* — Morgan, Lewis & Bockius LLP

(57) ABSTRACT

The disclosure herein provides combination therapies for the treatment of cancers such as Leukemia, lymphoma and triple negative breast cancer. The disclosure provides combination therapies of CDK inhibitors, e.g., a CDK inhibitor represented by Formula I:

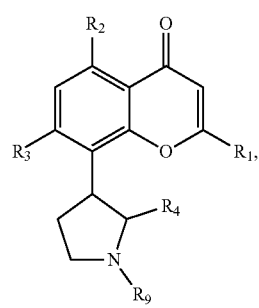

or a pharmaceutically acceptable salt thereof together with a BCL-2 inhibitor or proteasome inhibitor for the treatment of cancer.

11 Claims, 44 Drawing Sheets

(56) References Cited

OTHER PUBLICATIONS

Notice of First Refusal for Korean Patent Application No. 10-2021-7021031, mailed Jul. 15, 2022, 5 pages.
Notice of Acceptance for Australian Patent Application No. 2020201247 dated Aug. 12, 2021, 3 pages.
Office Action for Canadian Application No. 3,103,604 mailed Feb. 18, 2022, 4 pages.
Office Action for Mexican Application No. 2018/011666 mailed Mar. 1, 2022, 6 pages.
Office Action for Canadian Patent Application No. 3,103,604 mailed Sep. 15, 2022, 3 pages.
Office Action for Israel Patent Application No. 261824; dated Oct. 21, 2020; 4 pages.
Shirsath et al.,; Molecular Cancer 2012, 11:77; "P276-00, a cyclin-dependent kinase inhibitor, modulates cell cycle and induces apoptosis in vitro and in vivo in mantle cell lymphoma cell lines"; 12 pages.
Phillips et al., Blood Cancer Journal 2015, 5, e368; "Loss in MCL-1 function sensitizes non-Hodgkin's lymphoma cell ines to the BCL-2 selective inhibitor venetoclax (ABT-199)"; 8 pages.
Chen et al., Cancer Research 2012, 72(16):4225-4237; "CDK Inhibitors Upregulate BH3-Only Proteins to Sensitize Human Myeloma Cells to BH3 Mimetic Therapies"; 14 pages.
Office Action for Chinese Patent Application No. 201780032783.3; dated Sep. 30, 2020; 22 pages.
Translation of Office Action for Chinese Patent Application No. 201780032783.3; dated Sep. 30, 2020; 14 pages.
Examination Report mailed Aug. 11, 2020 in connection with AU application No. 2020201247.
Office action mailed Aug. 13, 2020 in connection with CA application No. 3,018,932.
Office Action for Korean Patent Application No. 10-2018-7030575 dated Nov. 28, 2020; 9 pages.
Office Action for Japanese Patent Application No. 2018-550790 dated Feb. 10, 2021; 9 pages.
Raje, N. et al., Leukemia, 2009, vol. 23, No. 5, pp. 961-970.
Office Action for Israel Patent Application No. 261824 dated Jun. 29, 2021; 4 pages.
Office Action for Chinese Patent Application No. 201780032783.3 dated Apr. 20, 2021; 30 pages.
Office Action for Mexican Patent Application No. MX/a/2018/011666 dated May 19, 2022, 6 pages.
Office Action for Mexican Patent Application No. 2018/011666 mailed Oct. 26, 2021, 8 pages.
Examination Report issued in Australian Patent Application No. 2021273532, dated Aug. 4, 2023, 2 pages.
Examination Report issued in European Patent Application No. 17776498, dated Sep. 10, 2023, 5 pages.
Notice of Reason for Rejection issued in Japanese Patent Application No. 2022-119166 dated Jun. 16, 2023, 6 pages.
Examination Report issued in European Patent Application No. 17776498.2, dated Oct. 9, 2023, 5 pages.
Office Action for European Patent Application No. 17776498.2 dated Feb. 17, 2023, 5 pages.
Office Action for Israel Patent Application No. 295472 dated Feb. 23, 2023, 4 pages.
Translation of Official Action issued in Russian Patent Application No. 2020121147, dated Nov. 8, 2023, 4 pages.
Examination Report mailed Feb. 25, 2019 in connection with AU application No. 2017241914.
Examination Report mailed Feb. 6, 2020 in connection with AU application No. 2017241914.
Office action mailed Oct. 18, 2019 in connection with CA application No. 3,018,932.
Extended Search Report mailed Nov. 7, 2019 in connection with European application No. 17776498.2.
Nitesh P. Shirsath et al: "P276-00, acyclin-dependent kinase inhibitor, modulates cell cycle and induces apoptosis in vitro and in vivo in mantle cell lymphoma eel I lines", Molecular Cancer, Biomed Central, London, GB, vol. 11, No. I, Oct. 18, 2012.
DC Phillips et al.: "Loss in MCL-1 1-15 function sensitizes non-Hodgkin's lymphoma cell lines to the BCL-2-selective inhibitor venetoclax (ABT-199)", Blood Cancer Journal, vol. 5, No. 11, Nov. 13, 2015 (Nov. 13, 2015), p. e368.
Shuang, C., et al.: "CDK Inhibitors Upregulate BH3-Only Proteins to Sensitize Human Myeloma Cells to BH3 Mimetic Therapies", Cancer Research, vol. 72, No. 16, Aug. 15, 2012, pp. 4225-4237.
Dai, Y., et al.: "Proteasome Inhibitors Potentiate Leukemic Cell Apoptosis Induced By The Cyclin-Dependent Kinase Inhibitor Flavopiridol Through a SAPK/JNK- and NF-KAPPABDEPENDENT Process", Oncogene, vol. 22, No. 46, Oct. 16, 2003, pp. 7108-7122.
Wang, S., et al.: "Cyclin-dependent kinase 9: a key transcriptional regulator and potential drug target in oncology, virology and cardiology", Trends in Pharmacological Sciences, vol. 29, No. 6, Jun. 1, 2008, pp. 302-313.
Examination Report mailed Oct. 17, 2019 in connection with Indian application No. 201817039382.
Notification of Provisional Rejection mailed Jan. 28, 2020 in connection with Korean application No. 10-2018-7030575.
First Examination Report mailed Mar. 13, 2019 in New Zealand application No. 747404.
Paiva et al. 2015. Cyclin-Dependent Kinase Inhibitor P1446A Induces Apoptosis in a JNK/p38 MAPK-Dependent Manner in Chronic Lymphocytic Leukemia B-Cells. Public Library of Science One, 25(11).
Second Examination Report mailed Nov. 5, 2019 in New Zealand application No. 747404.
Dey et al. (2016).Voruciclib Sensitizes High Risk Diffuse Large B Cell Lymphoma to BCL2 Inhibition Mediated Cell Death and Tumor Regression. Blood, 128(22): 4167.
Third Examination Report mailed Feb. 18, 2020 in New Zealand application No. 747404.
First official action mailed Aug. 8, 2019 in connection with Russian application No. 2018137687.
Bogenberger et al., Oncotarget. 2017; 8:107206-107222.
Second official action mailed Dec. 26, 2019 in connection with Russian application No. 2018137687.
International Search Report mailed May 18, 2017 in connection with International patent application No. PCT/US2017/024618.
Written Opinion mailed May 18, 2017 in connection with International patent application No. PCT/US2017/024618.
Decision on Grant mailed Apr. 28, 2020 in connection with Russian application No. 2018137687.
D.A. Kharkevich, Farmakologiya [Pharmacology], M., Meditsina, 1987.
Notice of Acceptance issued in Australian Patent Application No. 2021273532, dated Jan. 18, 2024, 3 pages.
Notification of Provisional Rejection issued in Korean Patent Application No. 10-2023-7037917, dated Jan. 29, 2024, 10 pages.
Translation of Official Action issued in Russian Patent Application No. 2020121147, dated Feb. 8, 2024, 8 pages.
Office Action issued in Mexican Patent Application No. MX/a/2020/013517, mailed Apr. 11, 2024, 4 pages.

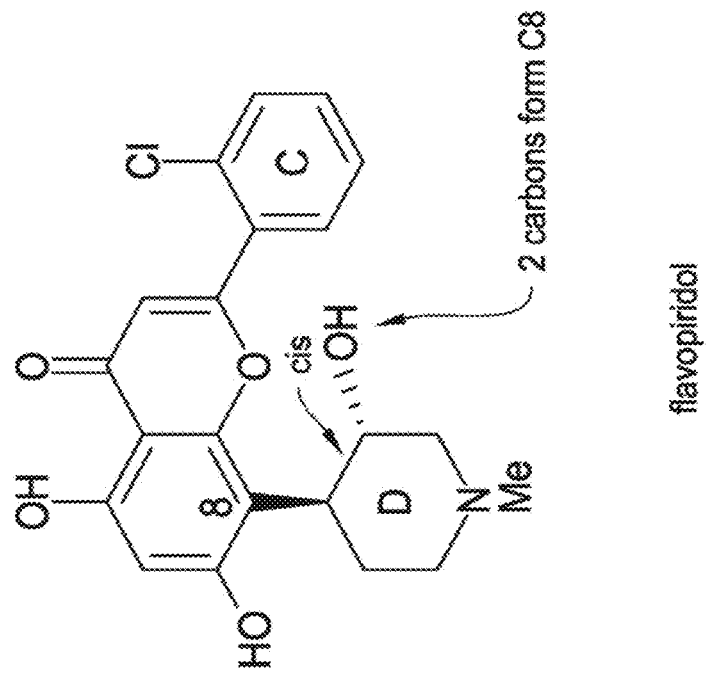
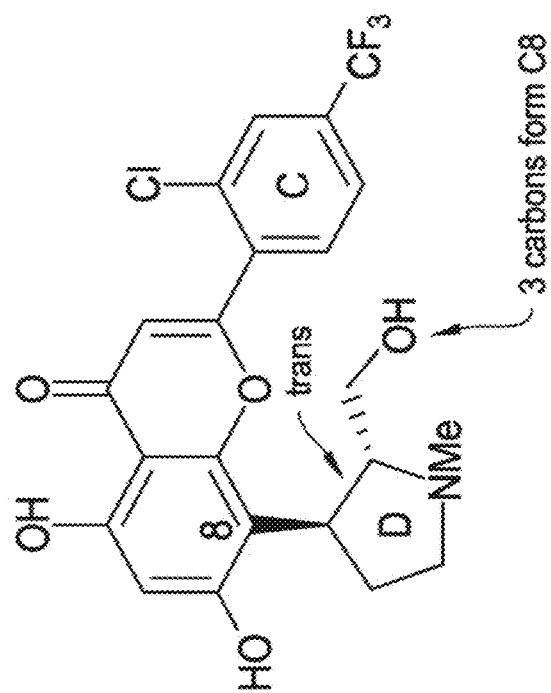
FIG. 1A

| Target | Ki (nM) |
|---|---|
| CDK9/cyc T2 | 0.626 |
| CDK9/cyc T1 | 1.68 |
| CDK6/cyc D1 | 2.92 |
| CDK4/cyc D1 | 3.96 |
| CDK1/cyc B | 5.4 |
| CDK1/cyc A | 9.1 |

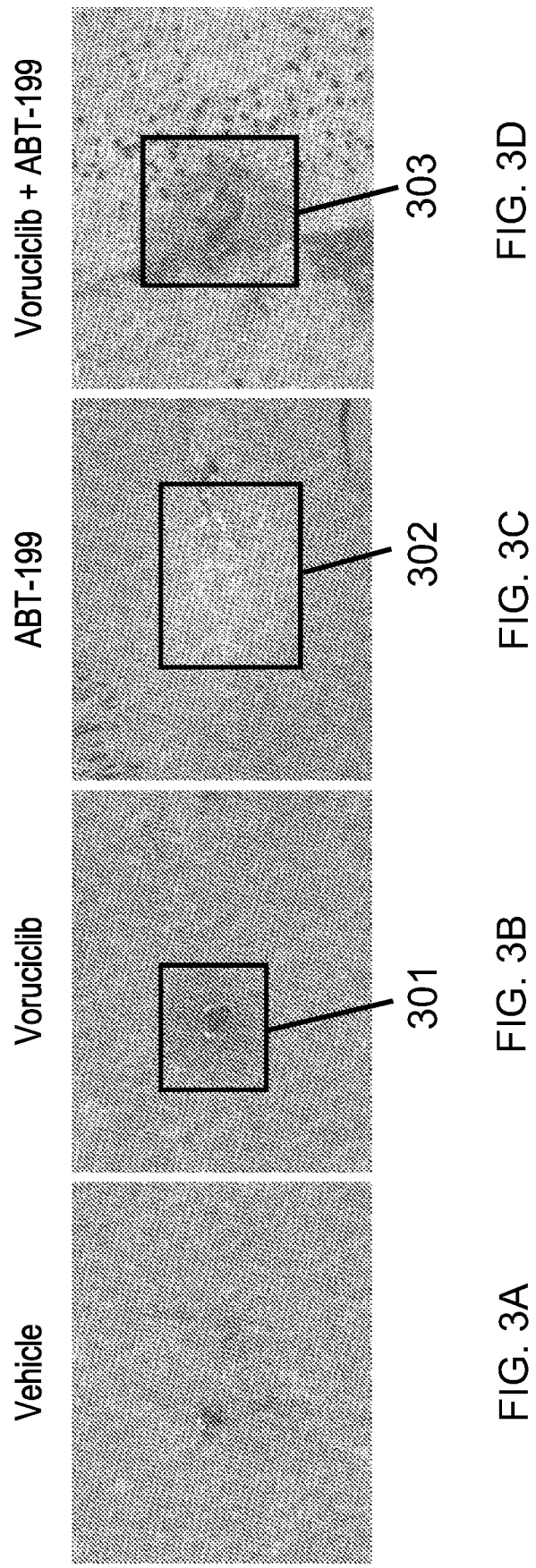

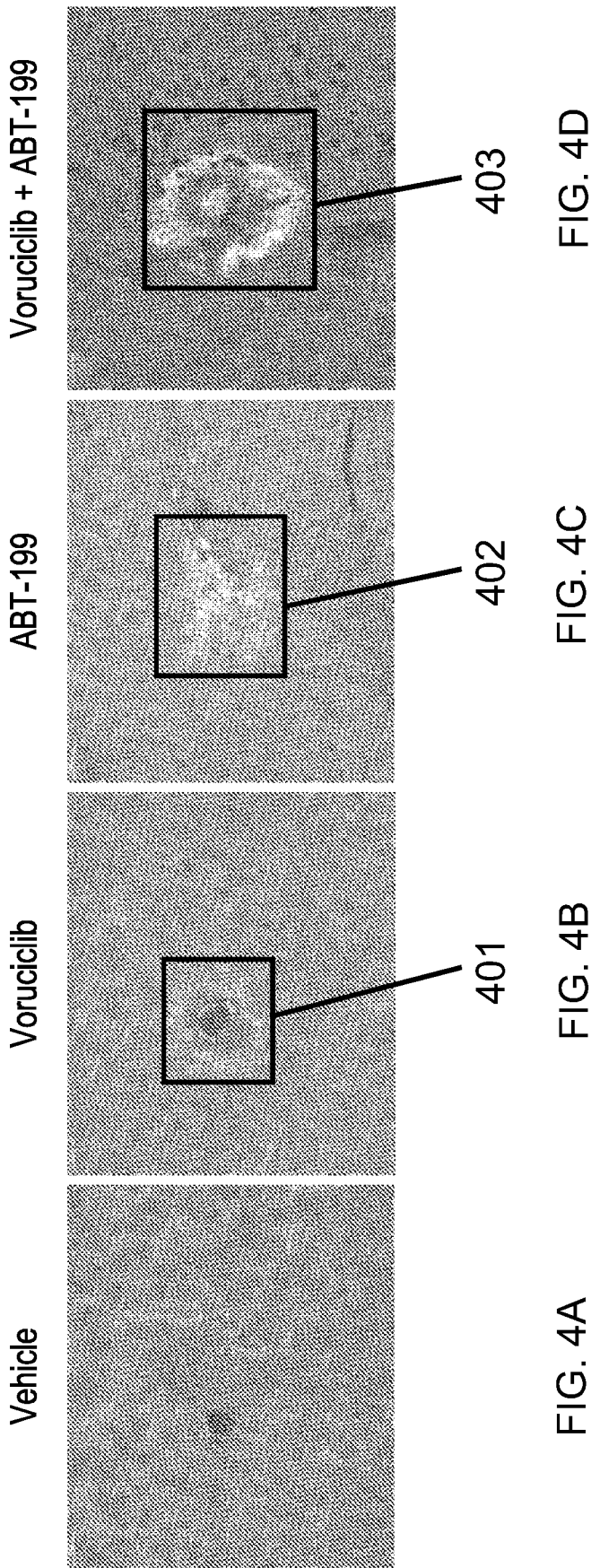

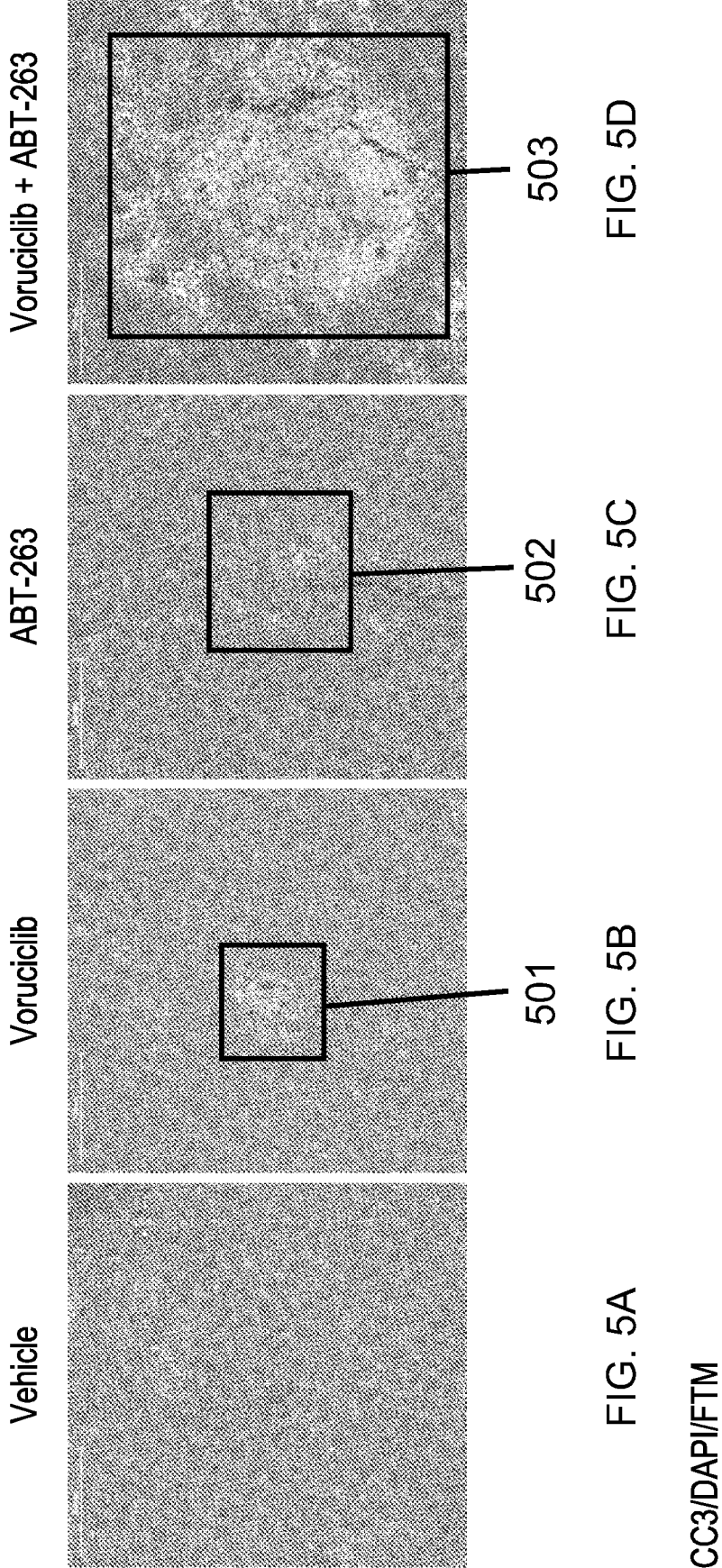

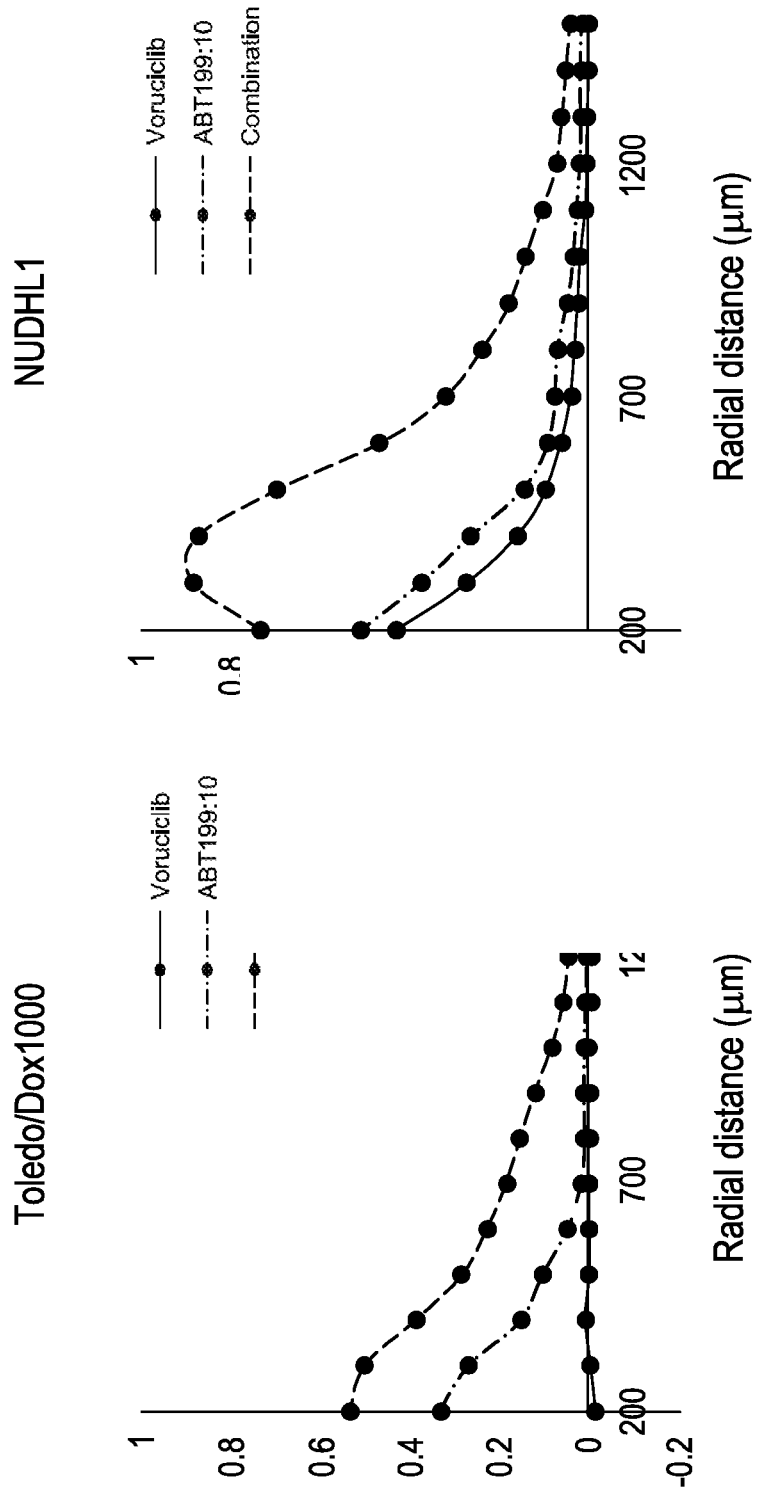

| CIVO screen in HCC1187 | |
|---|---|
| Chemo/DNA Damaging agent | Doxorubicin |
| Platinating agent | Carboplatin |
| S phase toxin | 5-FU |
| Mitotic inhibitor | Abraxane |
| PARP inhibitor | Olaparib |
| MEK inhibitor | Trametinib |
| mTOR inhibitor | Everolimus |
| PI3K inhibitor | BEZ235 |
| HSP90 inhibitor | PU-H71 |
| JAK2 inhibitor | Ruxolitinib |
| EGFR inhibitor | Erlotinib |
| VEGFR TK | Sunitinib |
| VEGFR TK | Sorafenib |
| Src inhibitor | Dasatinib |
| Proteasome inhibitor | Bortezomib |
| Proteasome inhibitor | Ixazomib |

FIG. 8A

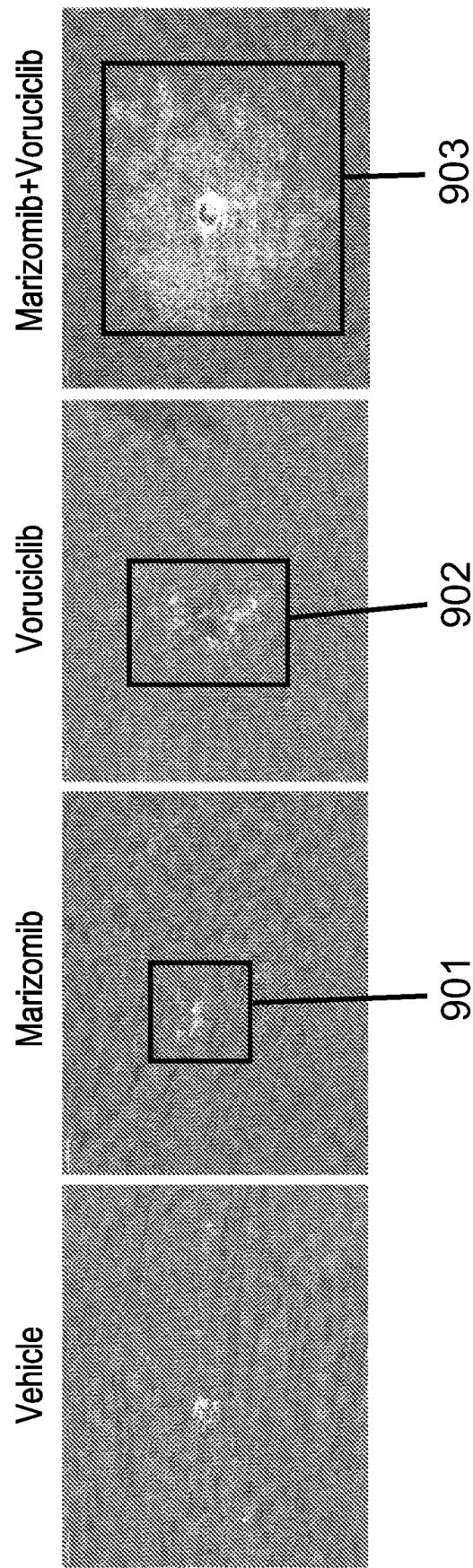

CC3/DAPI/FTM

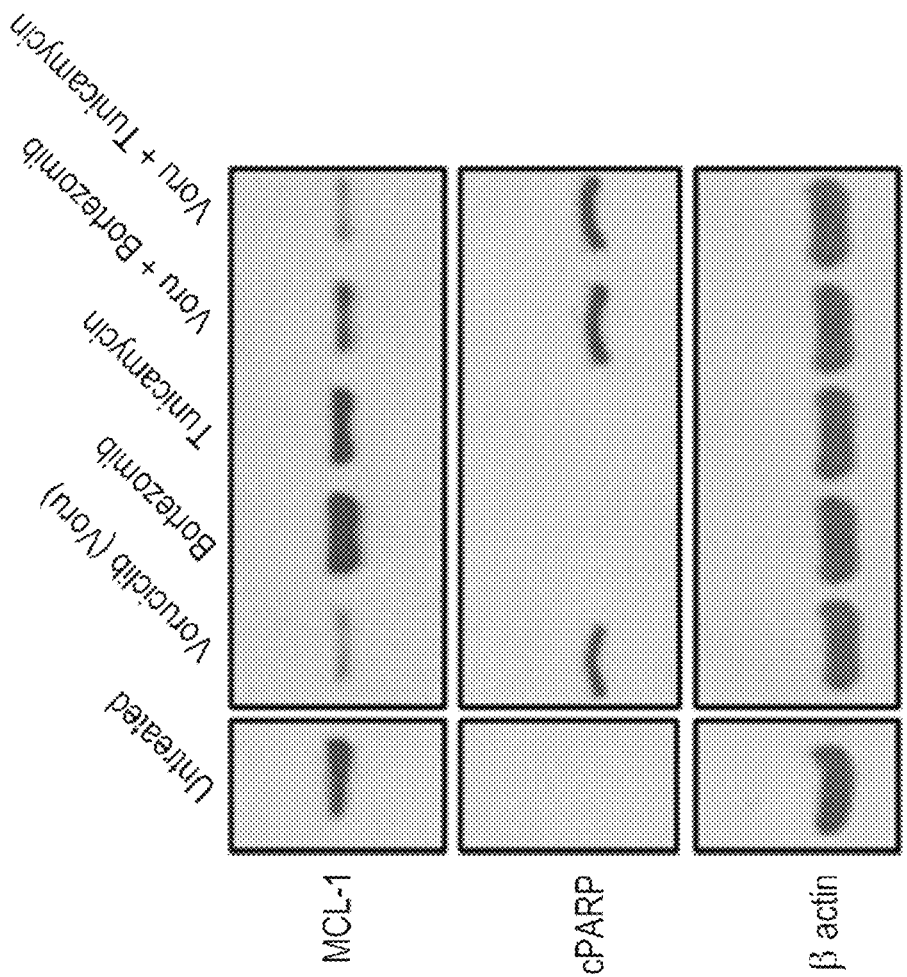
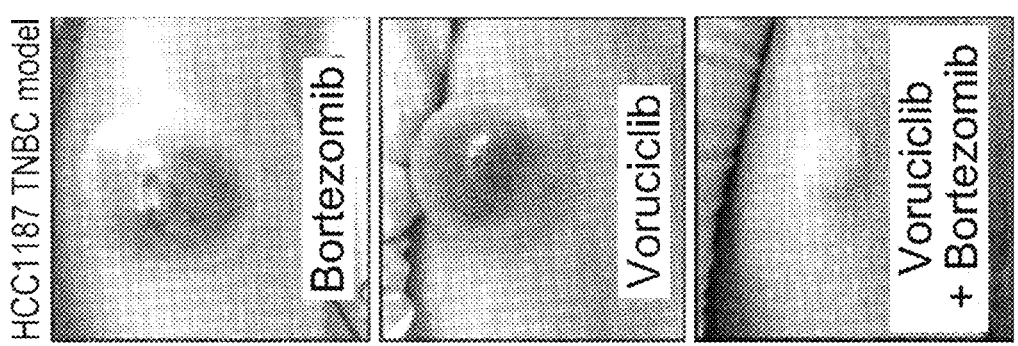
FIG. 12B
FIG. 12C
FIG. 12D

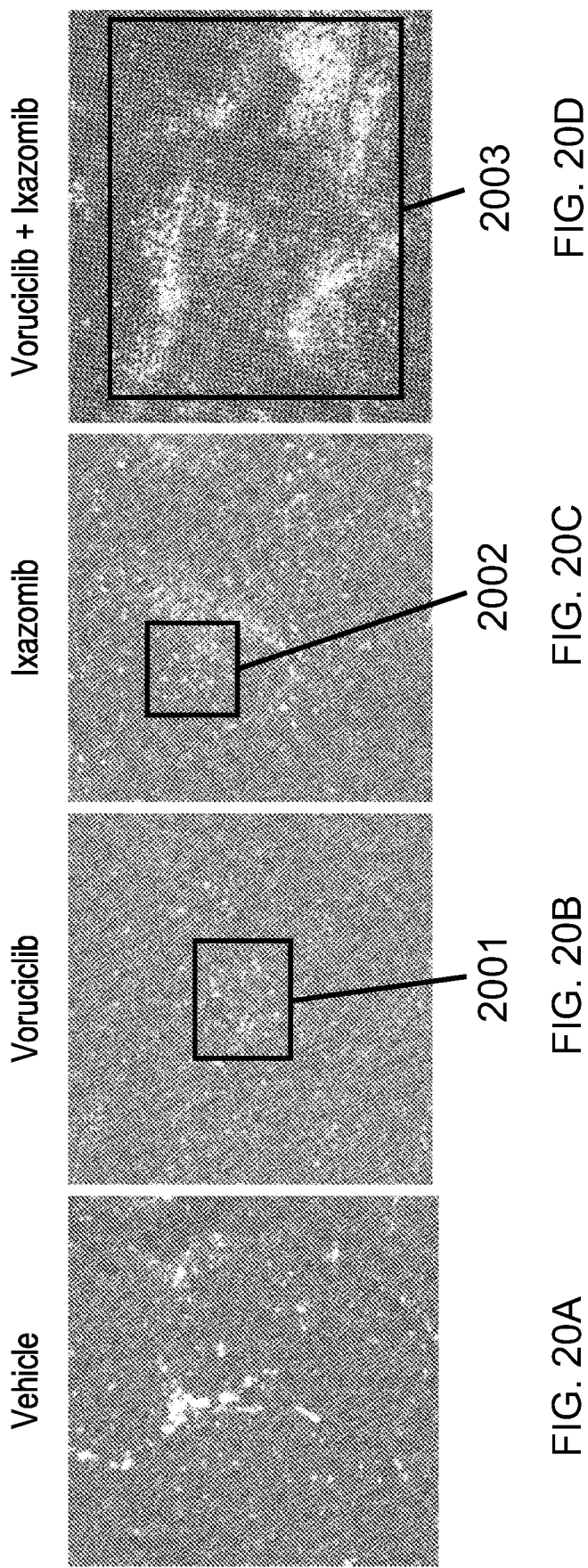

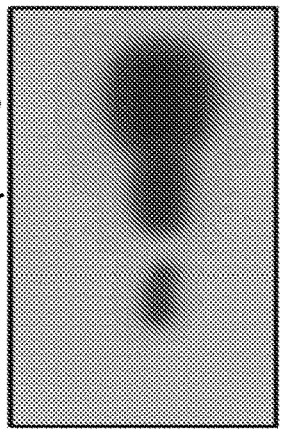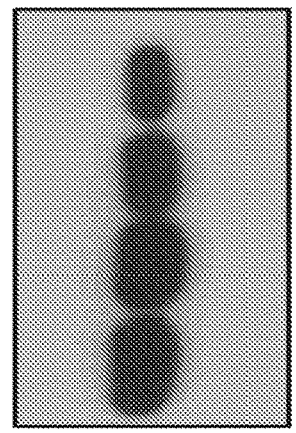
FIG. 23A  FIG. 23B  FIG. 23C

PHARMACEUTICAL COMBINATIONS FOR THE TREATMENT OF CANCER

CROSS-REFERENCE TO RELATED APPLICATIONS

This application is a continuation of U.S. patent application Ser. No. 16/089,276, filed Sep. 27, 2018, now granted U.S. Pat. No. 11,135,198, which is the U.S. National Stage Patent Application of International Application No. PCT/US2017/024618, filed Mar. 28, 2017, which claims priority to U.S. Provisional Patent Application Ser. No. 62/314,356, filed Mar. 28, 2016, each of which applications is incorporated herein by reference in its entirety.

BACKGROUND

Numerous cancer-related therapeutics are under phase I or phase II clinical trial and evaluations at any particular time; however, most of them will fail to advance. In fact, it is estimated that more than 90% of cancer-related therapeutics will fail phase I or II clinical trial evaluation. The failure rate in phase III trials is almost 50%, and the cost of new drug development from discovery through phase III trials is between $0.8 billion and $1.7 billion and can take between eight and ten years.

In addition, many patients fail to respond even to standard drugs that have been shown to be efficacious. For reasons that are not currently well understood or easily evaluated, individual patients may not respond to standard drug therapy. In some cases, administration of drug combinations may be more efficacious for treating cancer than drugs administered individually. These drug combinations may act synergistically to enhance the anti-cancer activity of the drugs. In some cases, drugs that are not particularly efficacious may find new and unexpected uses when combined with additional drug therapies.

SUMMARY

In one aspect, the disclosure provides a method of treating a blood cancer comprising administering to a subject in need thereof a therapeutically effective amount of a CDK inhibitor represented by Formula I:

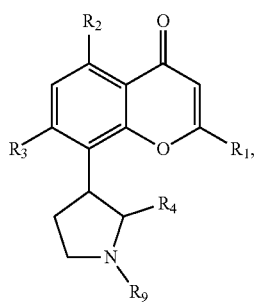

I or a pharmaceutically acceptable salt thereof, wherein:
$R_1$ is optionally substituted phenyl;
$R_2$ and $R_3$ are each independently selected from hydroxy and $OR_8$, wherein $R_8$ is optionally substituted $C_1$-$C_{10}$-alkyl;
$R_4$ is optionally substituted $C_1$-$C_4$-alkyl; and
$R_9$ is hydrogen or optionally substituted $C_1$-$C_4$-alkyl;
and a therapeutically effective amount of a BCL-2 inhibitor.

In certain aspects, the disclosure provides a method of treating a cancer comprising administering to a subject in need thereof a therapeutically effective amount of a CDK inhibitor represented by Formula I:

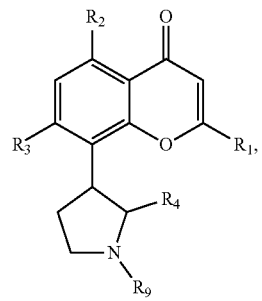

I or a pharmaceutically acceptable salt thereof, wherein:
$R_1$ is optionally substituted phenyl;
$R_2$ and $R_3$ are each independently selected from hydroxy and $OR_8$, wherein $R_8$ is optionally substituted $C_1$-$C_{10}$-alkyl;
$R_4$ is optionally substituted $C_1$-$C_4$-alkyl; and
$R_9$ is hydrogen or optionally substituted $C_1$-$C_4$-alkyl;
and a therapeutically effective amount of a proteasome inhibitor. In certain embodiments, the cancer is selected from a blood cancer and triple negative breast cancer (TNBC).

In certain embodiments, the compound of Formula I is represented by Formula Ia:

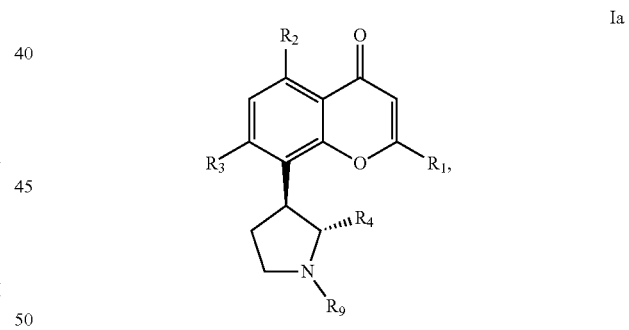

Ia or a pharmaceutically acceptable salt thereof.

In certain embodiments for a compound or salt of Formula I or Ia, $R_1$ is optionally substituted with one or more substituents independently selected from hydroxy, cyano, halo, amino, $C_1$-$C_4$-alkyl, $C_1$-$C_4$-alkoxy, $C_1$-$C_4$-hydroxyalkyl, $C_1$-$C_4$-haloalkyl, and nitro. In certain embodiments, $R_1$ is substituted with one or more substituents independently selected from halo and $C_1$-$C_4$-haloalkyl. In certain embodiments, $R_1$ is 2-chloro-4-trifluoromethylphenyl.

In certain embodiments for a compound or salt of Formula I or Ia, $R_2$ and $R_3$ are each independently selected from hydroxy and $OR_8$, wherein $R_8$ is $C_1$-$C_{10}$-alkyl optionally substituted with one or more substituents independently selected from hydroxy, cyano, halo, amino, =O, =S, $C_1$-$C_4$-alkoxy, and nitro. In certain embodiments, $R_2$ and $R_3$ are each hydroxy.

In certain embodiments for a compound or salt of Formula I or Ia, $R_4$ is $C_1$-$C_4$-alkyl substituted with one or more substituents selected from hydroxy, cyano, halo, amino, =O, =S, $C_1$-$C_4$-alkoxy, and nitro. In certain embodiments, $R_4$ is $C_1$-$C_4$-alkyl substituted with one or more substituents selected from hydroxy, cyano, halo, amino, =O, =S, $C_1$-$C_4$-alkoxy, and nitro. In certain embodiments, $R_4$ is 2-hydroxymethyl.

In certain embodiments for a compound or salt of Formula I or Ia, $R_9$ is $C_1$-$C_4$-alkyl optionally substituted with hydroxy, cyano, halo, amino, =O, =S, $C_1$-$C_4$-alkoxy, and nitro. In certain embodiments, $R_9$ is methyl. In certain embodiments the compound of Formula I is represented by formula Ib:

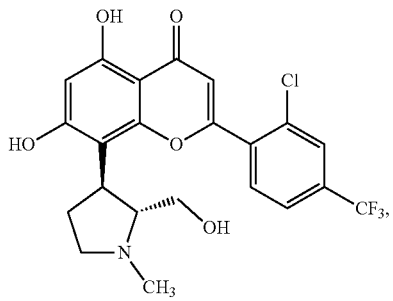

Ib or a pharmaceutically acceptable salt thereof.

In certain embodiments, the BCL-2 inhibitor of the methods described herein is a BH3-mimetic. The BCL-2 inhibitor may specifically inhibit the Bcl-2 protein. The BCL-2 inhibitor may be selected from navitoclax, venetoclax, A-1155463, A-1331852, ABT-737, obatoclax, S44563, TW-37, A-1210477, AT101, HA14-1, BAM7, sabutoclax, UMI-77, gambogic acid, maritoclax, MIM1, methylprednisolone, iMAC2, Bax inhibitor peptide V5, Bax inhibitor peptide P5, Bax channel blocker, and ARRY 520 trifluoroacetate. In certain embodiments, the BCL-2 inhibitor of the methods described herein is selected from navitoclax and venetoclax or a pharmaceutically acceptable salt of either one thereof.

In certain embodiments, the blood cancer of the methods described herein is selected from acute myeloid leukemia (AML), chronic myeloid leukemia (CML), acute lymphocytic lymphoma (ALL), and chronic lymphocytic leukemia (CLL), diffuse large B-cell lymphoma (DLBCL), primary mediastinal B-cell lymphoma, intravascular large B-cell lymphoma, follicular lymphoma, small lymphocytic lymphomia (SLL), mantle cell lymphoma, marginal zone B-cell lymphomas, extranodal marginal zone B-cell lymphomas, nodal marginal zone B-cell lymphoma, splenic marginal zone B-cell lymphoma, Burkitt lymphoma, lymphoplasmacytic lymphoma, and primary central nervous system lymphoma. The blood cancer may be diffuse large B-cell lymphoma, acute myeloid leukemia or chronic lymphocytic leukemia.

For certain methods described herein, the CDK inhibitor and BCL-2 inhibitor may be administered concurrently. For the methods described herein, the CDK inhibitor and BCL-2 inhibitor may be administered sequentially within about 12 hours of each other, such as within about 5 hours of each other.

For certain methods described herein, the CDK inhibitor and BCL-2 inhibitor may be co-formulated in a pharmaceutical composition.

For certain methods described herein, the CDK inhibitor and BCL-2 inhibitor may be administered daily, every other day or every third day.

For certain methods described herein, the proteasome inhibitor is selected from bortezomib, marizomib, ixazomib, disulfiram, epigallocatechin-3-gallate, salinosporamide A, carfilzomib, ONX 0912, CEP-18770, MLN9708, epoxomicin, MG132 and a pharmaceutically acceptable salt of any one thereof. In certain embodiments, the proteasome inhibitor is selected from bortezomib, marizomib, ixazomib, and a pharmaceutically acceptable salt of any one thereof.

In certain methods described herein, the CDK inhibitor and proteasome inhibitor are administered concurrently. The CDK inhibitor and proteasome inhibitor may be administered sequentially within about 12 hours of each other, such as within 5 hours of each other.

In certain methods described herein, the CDK inhibitor and proteasome inhibitor are co-formulated in a pharmaceutical composition.

In certain methods described herein, the CDK inhibitor and BCL-2 inhibitor are administered daily, every other day or every third day.

In certain aspects the disclosure provides a pharmaceutical composition comprising a therapeutically effective amount of a CDK inhibitor represented by Formula I:

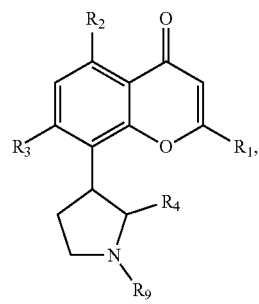

I or a pharmaceutically acceptable salt thereof, wherein:
  $R_1$ is optionally substituted phenyl;
  $R_2$ and $R_3$ are each independently selected from hydroxy and $OR_8$, wherein $R_8$ is optionally substituted $C_1$-$C_{10}$-alkyl;
  $R_4$ is optionally substituted $C_1$-$C_4$-alkyl; and
  $R_9$ is hydrogen or optionally substituted $C_1$-$C_4$-alkyl;
a therapeutically effective amount of a BCL-2 inhibitor or a proteasome inhibitor, and a pharmaceutically acceptable excipient.

In certain embodiments, the compound or salt of Formula I is represented by Formula Ia:

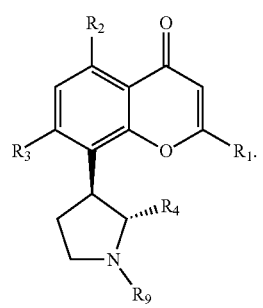

Ia

For the compositions described herein, for a compound or salt of Formula I or Ia, $R_1$ may be optionally substituted with one or more substituents independently selected from hydroxy, cyano, halo, amino, $C_1$-$C_4$-alkyl, $C_1$-$C_4$-alkoxy, $C_1$-$C_4$-hydroxyalkyl, $C_1$-$C_4$-haloalkyl, and nitro. In certain embodiments, $R_1$ is substituted with one or more substituents independently selected from halo and $C_1$-$C_4$-haloalkyl. In certain embodiments, $R_1$ is 2-chloro-4-trifluoromethylphenyl.

For the compositions described herein, for a compound or salt of Formula I or Ia, $R_2$ and $R_3$ may each independently selected from hydroxy and $OR_8$, wherein $R_8$ is $C_1$-$C_{10}$-alkyl optionally substituted with one or more substituents independently selected from hydroxy, cyano, halo, amino, $=O$, $=S$, $C_1$-$C_4$-alkoxy, and nitro. In certain embodiments, $R_2$ and $R_3$ are each hydroxy.

For the compositions described herein, for a compound or salt of Formula I or Ia, $R_4$ is $C_1$-$C_4$-alkyl substituted with one or more substituents selected from hydroxy, cyano, halo, amino, $=O$, $=S$, $C_1$-$C_4$-alkoxy, and nitro. In certain embodiments, $R_4$ is $C_1$-$C_4$-alkyl substituted with one or more substituents selected from hydroxy, cyano, halo, amino, $=O$, $=S$, $C_1$-$C_4$-alkoxy, and nitro. In certain embodiments, $R_4$ is 2-hydroxymethyl.

For the compositions described herein, for a compound or salt of Formula I or Ia, $R_9$ may be $C_1$-$C_4$-alkyl optionally substituted with hydroxy, cyano, halo, amino, $=O$, $=S$, $C_1$-$C_4$-alkoxy, and nitro. In certain embodiments, $R_9$ is methyl.

For the compositions described herein, the compound of Formula I may be represented by Formula Ib:

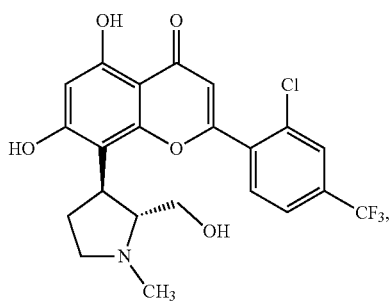

Ib or a pharmaceutically acceptable salt thereof.

For the compositions described herein comprising a BCL-2 inhibitor, the BCL-2 inhibitor may be selected from navitoclax, venetoclax, A-1155463, A-1331852, ABT-737, obatoclax, S44563, TW-37, A-1210477, AT101, HA14-1, BAM7, sabutoclax, UMI-77, gambogic acid, maritoclax, MIM1, methylprednisolone, iMAC2, Bax inhibitor peptide V5, Bax inhibitor peptide P5, Bax channel blocker, ARRY 520 trifluoroacetate and a pharmaceutically acceptable salt of any one thereof. The BCL-2 inhibitor may be selected from navitoclax and venetoclax or a pharmaceutically acceptable salt of either one thereof. In certain embodiments, the BCL-2 inhibitor is venetoclax.

For the compositions described herein comprising a proteasome inhibitor, the proteasome inhibitor may be selected from bortezomib, marizomib, ixazomib, disulfiram, epigallocatechin-3-gallate, salinosporamide A, carfilzomib, ONX 0912, CEP-18770, MLN9708, epoxomicin, MG132 and a pharmaceutically acceptable salt of any one thereof. In certain embodiments, the proteasome inhibitor is selected from bortezomib, marizomib, ixazomib, and a pharmaceutically acceptable salt of any one thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A depicts the structures of voruciclib and flavopiradol.

FIGS. 3A-3D illustrate a synergistic effect of voruciclib in combination with venetoclax (ABT-199). Voruciclib inhibits the induction of induced myeloid leukemia cell differentiation protein (MLC-1) by venetoclax in NU-DHL-1 diffuse large B-cell lymphoma (DLBCL) cells. MCL-1=red; DAPI=blue; fluorescent tracking marker (FTM)=green.

FIGS. 4A-4D illustrate increased apoptosis in NU-DHL-1 diffuse large B-cell lymphoma (DLBCL) cells by combination treatment with voruciclib and venetoclax. Cleaved caspase-3 (CC3)=red; DAPI=blue; fluorescent tracking marker (FTM)=green.

FIGS. 5A-5D illustrate a synergistic effect of voruciclib in combination with navitoclax (ABT-263). Treatment of the Ramos Burkitt's lymphoma cell line with voruciclib and navitoclax induces apoptosis. Cleaved caspase-3 (CC3) =red; DAPI=blue; fluorescent tracking marker (FTM) =green.

FIGS. 6A-6E illustrate a synergistic effect of voruciclib in combination with venetoclax across five models of diffuse large B-cell lymphoma.

FIGS. 8A-8D illustrates that proteasome inhibition induces upregulation of MCL-1 in triple negative breast cancer (TNBC). FIG. 8A illustrates a list of compounds screened in HCC1187 TNBC xenograft model. FIG. 8B illustrates the mean % change in MCL-1 induction by treatment with various compounds. FIGS. 8C-8D illustrate staining of cells for CC3 (shown in red) with vehicle and after treatment with bortezomib.

FIGS. 9A-9D illustrate a synergistic effect of voruciclib in combination with marizomib on NudHL1 DLBCL cells. Cleaved caspase-3 (CC3)=red; DAPI=blue; fluorescent tracking marker (FTM)=green.

FIGS. 12A-12E illustrate a synergistic effect of voruciclib in combination with bortezomib on HCC1187 triple-negative breast cancer cells. FIGS. 12A-12D illustrate decreased tumor volume in an HCC1187 TNBC mouse model treated with voruciclib and bortezomib.

FIG. 12E illustrates a Western blot demonstrating decreased MCL-1 expression in HCC1187 TNBC cells treated with voruciclib and bortezomib or voruciclib and tunicamycin.

FIG. 15A illustrates a proposed model of voruciclib inhibition of CDK9. FIG. 15B illustrates a Western blot demonstrating that voruciclib diminishes bortezomib-induced increase in MCL-1 and E3 ubiquitin-protein ligase XIAP expression.

FIG. 16A illustrates cells resistant to bortezomib treatment in an area otherwise cleared of cells by bortezomib treatment. FIG. 16B illustrates that cells resistant to bortezomib express GRP78, a protein expressed as part of the ER stress response.

FIG. 18A illustrates the IRE1α-dependent ER stress response pathway. FIG. 18B illustrates a Western blot demonstrating that the ER stress inducer tunicamycin dramatically upregulates X-box binding protein 1 (XBP1), a pro-survival (anti-tumor cell death) protein. This effect is dramatically mitigated by voruciclib. At 6 hours, only tunicamycin illustrates this effect, but at 24 hours, both bortezomib and tunicamycin illustrate this effect.

FIGS. 20A-20D illustrate a synergistic effect of voruciclib in combination with ixazomib. Cleaved-caspase 3 (CC3) =red; DAPI=blue; fluorescent tracking marker (FTM) =green.

FIGS. 23A-23C illustrate the synergy from voruciclib and venetoclax in the SU-DHL-4 model, the OCI Ly10 model, and the U2932 model of diffuse large B-cell lymphoma (DLBCL).

DETAILED DESCRIPTION

Figure 1B:
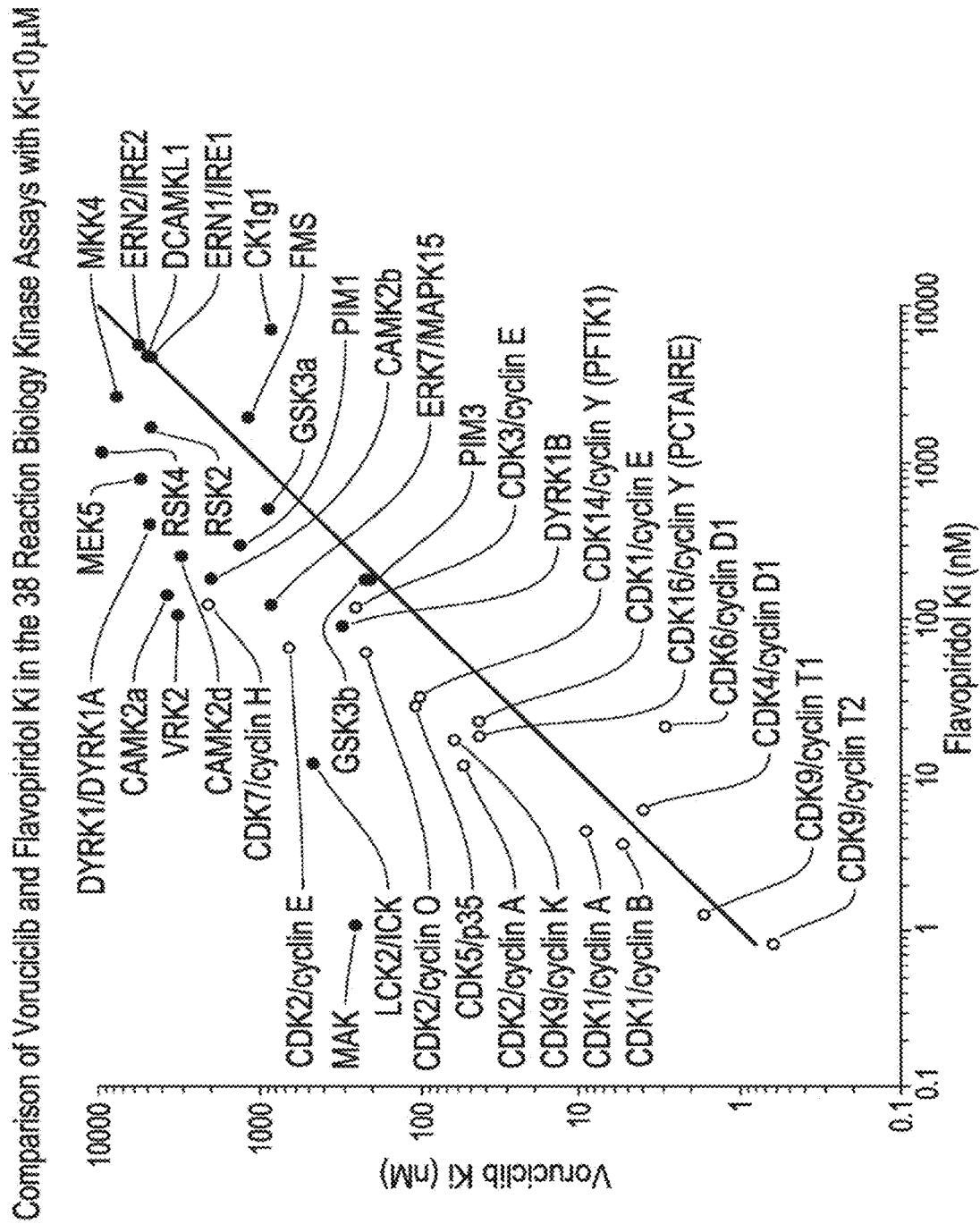
FIG. 1B illustrates a comparison of voruciclib and flavopiradol activity against 38 kinases.

The disclosure provides combination therapies for the treatment of cancer. In particular, the disclosure provides combination therapies of CDK inhibitors with other anticancer agents for treating cancer. In one aspect the disclosure provides compositions and methods for treating cancer with a CDK inhibitor in combination with a BCL-2 inhibitor. Such combination provides synergistic effects in the treatment of cancers and particularly treatment of blood cancers, e.g., leukemia and lymphoma.

In another aspect, the disclosure provides compositions and methods for treating cancer with a CDK inhibitor in combination with a proteasome inhibitor. Such combination provides a synergistic effect in the treatment of cancer and particularly treatment of blood cancers and triple negative breast cancer.

The general terms used hereinbefore and hereinafter preferably have the following meanings within the context of this disclosure, unless otherwise indicated. Thus, the definitions of the general terms as used in the context of the present invention are provided herein below:

The singular forms "a," "an," and "the" include plural reference unless the context clearly dictates otherwise.

The term "about," as used herein, generally refers to an acceptable error range for the particular value as determined by one of ordinary skill in the art, which may depend in part on how the value is measured or determined. For example, "about" can mean within 1 or more than 1 standard deviation. Alternatively, "about" can mean a range of up to 20%, up to 10%, up to 5%, or up to 1% of a given value. Alternatively, particularly with respect to biological systems or processes, the term can mean within an order of magnitude, within 5-fold, and within 2-fold, of a value.

As used herein, the term "at least one" is refers to one or more. For instance, the term "at least one anticancer agent" means that the combination comprises a single anticancer agent or more anticancer agents.

The term "effective amount" or "therapeutically effective amount," as used herein, generally refers to an amount of a compound described herein that is sufficient to affect an intended, predetermined or prescribed application, including but not limited to, disease or condition treatment. The therapeutically effective amount can vary depending upon the application (e.g., in vitro or in vivo), or the subject and disease condition being treated, e.g., the weight and age of the subject, the severity of the disease condition and the manner of administration. The term also may apply to a dose that induces a particular response in target cells, e.g., reduction of proliferation or down regulation of activity of a target protein. The specific dose may vary depending on the particular compounds chosen, the dosing regimen to be followed, whether it is administered in combination with other compounds, timing of administration, the tissue to which it is administered, and the physical delivery system in which it is carried.

As used herein, the term "pharmaceutically acceptable" means that the carrier, diluent, excipients, and/or salt must be compatible with the other ingredients of the formulation, and not deleterious to the recipient thereof "Pharmaceutically acceptable" also means that the compositions or dosage forms are within the scope of sound medical judgment, suitable for use for an animal or human without excessive toxicity, irritation, allergic response, or other problem or complication, commensurate with a reasonable benefit/risk ratio.

As used herein, the term "combination" or "pharmaceutical combination" refers to the combined administration of the anticancer agents. Combinations of the disclosure include a CDK inhibitor, e.g., a compound of Formula I, Ia, or Ib, and at least one anticancer agent selected from a BCL-2 inhibitor and a proteasome inhibitor; which anticancer agents may be administered to a subject in need thereof, e.g., concurrently or sequentially.

The term "synergistic," or "synergistic effect" or "synergism" as used herein, generally refers to an effect such that the one or more effects of the combination of compositions is greater than the one or more effects of each component alone, or they can be greater than the sum of the one or more effects of each component alone. The synergistic effect can be greater than about 10%, 20%, 30%, 50%, 75%, 100%, 110%, 120%, 150%, 200%, 250%, 350%, or 500% or more than the effect on a subject with one of the components alone, or the additive effects of each of the components when administered individually. The effect can be any of the measurable effects described herein. Advantageously, such synergy between the agents when combined, may allow for the use of smaller doses of one or both agents, may provide greater efficacy at the same doses, and may prevent or delay the build-up of multi-drug resistance. The combination index (CI) method of Chou and Talalay may be used to determine the synergy, additive or antagonism effect of the agents used in combination. When the CI value is less than 1, there is synergy between the compounds used in the combination; when the CI value is equal to 1, there is an additive effect between the compounds used in the combination and when CI value is more than 1, there is an antagonistic effect. The synergistic effect may be attained by co-formulating the agents of the pharmaceutical combination. The synergistic effect may be attained by administering two or more agents as separate formulations administered simultaneously or sequentially.

Cyclin-dependent kinases (CDKs) are a family of enzymes which become activated in specific phases of the cell cycle. CDKs consist of a catalytic subunit (the actual cyclin-dependent kinase or CDK) and a regulatory subunit (cyclin). There are at least nine CDKs (CDK1, CDK2, CDK3, CDK4, CDK5, CDK6, CDK7, CDK8, CDK9, etc.) and at least 15 different types of cyclins (cyclin A, B1, B2, D1, D2, D3, E, H etc.). Each step of the cell cycle is regulated by such CDK complexes: G1/S transition (CDK2/cyclin A, CDK4/cyclin D1-D3, CDK6/cyclin D3), S phase (CDK2/cyclin A), G2 phase 30 (CDK1/cyclin A), G2/M transition phase (CDK1/cyclin B).

As used herein, the term "CDK inhibitor" refers to an agent that is capable of inhibiting one or more cyclin dependent kinases (CDK). Aberrant expression and overexpression of these kinases are evidenced in many disease conditions such as cancer. In the context of the present invention, the CDK inhibitor of the pharmaceutical combination described herein may be a compound of Formula I, Ia, or Ib or a pharmaceutically acceptable salt thereof. The compounds of the present disclosure may inhibit one or more of CDK1/cyclin B, CDK2/cyclin E, CDK4/cyclin D, CDK4/cyclin D1 and CDK9/cyclin T1 with specificity. In certain embodiments, a compound of the disclosure inhibits CDK9/cyclin T1 or CDK9 with specificity.

Disclosed herein are combination therapies for the treatment of cancer, e.g., leukemia, lymphoma and breast cancer. The methods and compositions described herein may include a cyclin-dependent kinase (CDK) inhibitor, such as a compound of Formula I, Ia, or Ib or a pharmaceutically acceptable salt thereof. In some cases, a combination therapy may include a CDK inhibitor in combination with a proteasome inhibitor. In other cases, a combination therapy may include a CDK inhibitor in combination with a BCL-2 inhibitor.

In certain embodiments, a CDK inhibitor of the disclosure is represented by a compound disclosed in U.S. Pat. Nos. 7,271,193; 7,915,301; 8,304,449; 7,884,127; 8,563,596, the entire contents of each of which are incorporated herein by reference. In certain embodiments, a CDK inhibitor of the disclosure is represented by Formula I:

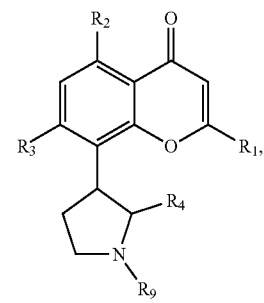

or a pharmaceutically acceptable salt thereof, wherein:
$R_1$ is optionally substituted phenyl;
$R_2$ and $R_3$ are each independently selected from hydroxy and $OR_8$, wherein $R_8$ is optionally substituted $C_1$-$C_{10}$-alkyl;
$R_4$ is optionally substituted $C_1$-$C_4$-alkyl; and
$R_9$ is hydrogen or optionally substituted $C_1$-$C_4$-alkyl.

In certain embodiments, the compound or salt of Formula I is represented by Formula Ia:

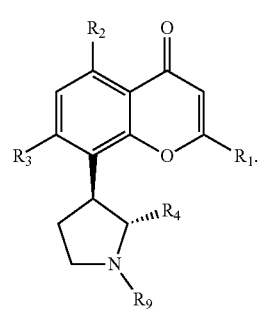

In certain embodiments for a compound or salt of Formula I or Ia, $R_1$ is optionally substituted with one or more substituents independently selected from hydroxy, cyano, halo, amino, $C_1$-$C_4$-alkyl, $C_1$-$C_4$-alkoxy, $C_1$-$C_4$-hydroxyalkyl, $C_1$-$C_4$-haloalkyl, and nitro. In certain embodiments, $R_1$ is substituted with one or more substituents independently selected from hydroxy, cyano, halo, $C_1$-$C_4$-alkyl, and $C_1$-$C_4$-haloalkyl. In certain embodiments, $R_1$ is substituted with one or more substituents independently selected from halo and $C_1$-$C_4$-haloalkyl. In certain embodiments, $R_1$ is 2-chloro-4-trifluoromethylphenyl.

The term "alkyl" refers to a straight or branched hydrocarbon chain radical consisting solely of carbon and hydrogen atoms, and containing no unsaturation. In certain embodiments, an alkyl comprises one to eight carbon atoms (i.e., $C_1$-$C_8$ alkyl). In other embodiments, an alkyl comprises one to five carbon atoms (i.e., $C_1$-$C_5$ alkyl). In other embodiments, an alkyl comprises one to four carbon atoms (i.e., $C_1$-$C_4$ alkyl). In other embodiments, an alkyl comprises one to three carbon atoms (i.e., $C_1$-$C_3$ alkyl). In other embodiments, an alkyl comprises one to two carbon atoms (i.e., $C_1$-$C_2$ alkyl). In other embodiments, an alkyl comprises one carbon atom (i.e., $C_1$ alkyl). In other embodiments, an alkyl comprises five to eight carbon atoms (i.e., $C_5$-$C_8$ alkyl). In other embodiments, an alkyl comprises two to five carbon atoms (i.e., $C_2$-$C_5$ alkyl). In other embodiments, an alkyl comprises three to five carbon atoms (i.e., $C_3$-$C_5$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more substituents such as those substituents described herein.

The term "alkoxy" refers to a radical bonded through an oxygen atom of the formula —O-alkyl, where alkyl is an alkyl chain as defined above.

The term "amino" refers to the group —NR'R", wherein R' and R" are independently selected from hydrogen; and alkyl, hydroxyl, aryl, cycloalkyl, heterocycloalkyl, and heteroaryl, any one of which may be optionally substituted with one or more substituents such as hydroxy, cyano, halo, amino, $C_1$-$C_4$-alkyl, $C_1$-$C_4$-alkoxy, $C_1$-$C_4$-hydroxyalkyl, $C_1$-$C_4$-haloalkyl, and nitro.

The term "$C_{x-y}$" when used in conjunction with a chemical moiety, such as alkyl is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc.

The term "haloalkyl" refers to an alkyl group that is substituted by one or more halo radicals, for example, trifluoromethyl, difluoromethyl, fluoromethyl, 2,2,2-trifluoroethyl, 1-chloromethyl-2-fluoroethyl, and the like. In some embodiments, the alkyl part of the haloalkyl is further optionally substituted as described herein.

The term "hydroxyalkyl" refers to an alkyl group that is substituted by one or more hydroxy radicals, for example, hydroxymethyl, hydroxyethyl, dihydroxymethyl, and the like. In some embodiments, the alkyl part of the hydroxyalkyl is further optionally substituted as described herein.

In certain embodiments for a compound or salt of Formula I or Ia, $R_2$ and $R_3$ are each independently selected from hydroxy and $OR_8$, wherein $R_8$ is $C_1$-$C_{10}$-alkyl optionally substituted with one or more substituents independently selected from hydroxy, cyano, halo, amino, =O, =S, $C_1$-$C_4$-alkoxy, and nitro. In certain embodiments, $R_8$ at each occurrence is selected from optionally substituted $C_1$-$C_6$-alkyl, such as optionally substituted $C_1$-$C_4$-alkyl. In certain embodiments, $R_2$ and $R_3$ are each independently hydroxy.

In certain embodiments for a compound or salt of Formula I or Ia, $R_4$ is optionally substituted $C_1$-$C_4$-alkyl, wherein $R_4$ is optionally substituted with one or more substituents selected from hydroxy, cyano, halo, amino, =O, =S, $C_1$-$C_4$-alkoxy, and nitro. In certain embodiments, $R_4$ is optionally substituted $C_1$-$C_2$-alkyl. In certain embodiments, $R_4$ is hydroxyalkyl, e.g., 2-hydroxymethyl.

In certain embodiments for a compound or salt of Formula I or Ia, $R_9$ is $C_1$-$C_4$-alkyl optionally substituted with hydroxy, cyano, halo, amino, =O, =S, $C_1$-$C_4$-alkoxy, and nitro. In certain embodiments, $R_9$ is optionally substituted $C_1$-$C_2$-alkyl. In certain embodiments, $R_9$ is methyl. In certain embodiments, $R_9$ is hydrogen.

In certain embodiments for a compound or salt of Formula I or Ia, a compound of Formula I is a compound or pharmaceutically acceptable salt selected from: (+)-trans-2-(2-Chloro-4-trifluoromethylphenyl)-8-(2-hydroxymethyl-1-methyl-pyrrolidin-3-yl)-5,7-dimethoxy-chromen-4-one; (+)-trans-2-(2-Chloro-4-trifluoromethylphenyl)-5,7-dihydroxy-8-(2-hydroxymethyl-1-methylpyrrolidin-3-yl)-chromen-4-one; and (+)-trans-2-(2-Chloro-4-trifluoromethylphenyl)-5,7-dihydroxy-8-(2-hydroxymethyl-1-methyl-pyrrolidin-3-yl)-chromen-4-one hydrochloride.

In certain embodiments, the compound of Formula I or Ia is represented by Formula Ib:

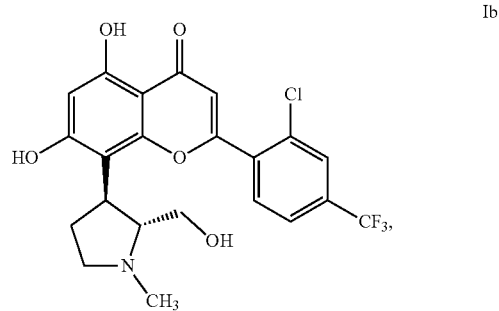 [SMILES: CN1CC[C@@H](c2c(O)cc(O)c3c(=O)cc(-c4ccc(C(F)(F)F)cc4Cl)oc23)[C@@H]1CO]

or a pharmaceutically acceptable salt thereof. In certain embodiments, the compound of Formula I, Ia, or Ib is in the form of an acid addition salt, such as the hydrochloride salt.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, as well as represents a stable compound, which does not readily undergo transformation such as rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

Substituents can include any substituents described herein, for example, a halogen, a hydroxy, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

Procedures for the manufacture of the compounds of Formula I, Ia, and Ib or the pharmaceutically acceptable salts thereof, may be found in PCT Patent Publication No. WO2004004632 (corresponding to U.S. Pat. No. 7,271,193) and PCT Patent Publication No. WO2007148158.

The present disclosure provides pharmaceutically-acceptable salts of any compound described herein, e.g., a compound of Formula I, Ia, Ib, BCL-2 inhibitors and proteasome inhibitors. Pharmaceutically-acceptable salts include, for example, acid-addition salts and base-addition salts. The acid that is added to a compound to form an acid-addition salt can be an organic acid or an inorganic acid. A base that is added to a compound to form a base-addition salt can be an organic base or an inorganic base. In some cases, a pharmaceutically-acceptable salt is a metal salt. In some cases, a pharmaceutically-acceptable salt is an ammonium salt.

Acid addition salts can arise from the addition of an acid to a compound described herein. In some cases, the acid is organic. In some cases, the acid is inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound described herein. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, pipyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts include is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzyl amine salt, a piperazine salt, a pyridine salt, a pyrrazole salt, a pipyrrazole salt, an imidazole salt, a pyrazine salt, a pipyrazine salt, an ethylene diamine salt, an N,N'-dibenzylethylene diamine salt, a procaine salt, a chloroprocaine salt, a choline salt, a dicyclohexyl amine salt, and a N-methylglucamine salt.

Non-limiting examples of suitable acid addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

The compounds described herein, e.g., the compounds and salts of Formulas I, Ia, Ib, BCL-2 inhibitors and proteasome inhibitors, may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The compounds described herein, e.g., the compounds and salts of Formulas I, Ia, Ib, BCL-2 inhibitors and proteasome inhibitors, include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

The compounds described herein, e.g., the compounds and salts of Formulas I, Ia, Ib, BCL-2 inhibitors and proteasome inhibitors, include compounds that exhibit their natural isotopic abundance, and compounds where one or more of the atoms are artificially enriched in a particular isotope having the same atomic number, but an atomic mass or mass number different from the atomic mass or mass number predominantly found in nature. All isotopic variations of the compounds of the present invention, whether radioactive or not, are encompassed within the scope of the present invention. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared.

Compounds described herein, e.g., the compounds and salts of Formulas I, Ia, Ib, BCL-2 inhibitors and proteasome inhibitors, wherein the compound has carbon-carbon double bonds or carbon-nitrogen double bonds may exist, where applicable, in Z- or E-form (or cis- or trans-form). Furthermore, some chemical entities may exist in various tautomeric forms. Unless otherwise specified, chemical entities described herein are intended to include all Z-, E- and tautomeric forms as well.

In certain cases, a compound described herein may be a prodrug, e.g., wherein a carboxylic acid present in the parent compound is presented as an ester. The term "prodrug" is intended to encompass compounds which, under physiologic conditions, are converted into pharmaceutical agents, i.e., parent compound, of the present disclosure. One method for making a prodrug is to include one or more selected moieties which are hydrolyzed under physiologic conditions to reveal the desired molecule. In certain embodiments, the prodrug is converted by an enzymatic activity of the host animal such as enzymatic activity in specific target cells in the host animal. For example, esters or carbonates (e.g., esters or carbonates of alcohols or carboxylic acids) are preferred prodrugs of the present disclosure.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. For example, the prodrug may have improved cell permeability over the parent compound. The prodrug may also have improved solubility in pharmaceutical formulations over the parent drug. In some embodiments, the design of a prodrug increases the lipophilicity of the pharmaceutical agent. In some embodiments, the design of a prodrug increases the effective water solubility.

In certain embodiments, a cyclin-dependent kinase (CDK) inhibitor, e.g., a compound or salt of Formula I, Ia or Ib, may be used in combination with an inhibitor of one or more proteins in the BCL-2 family. Inhibitors of BCL-2 anti-apoptotic family of proteins alter at least a cell survival pathway. Apoptosis activation may occur via an extrinsic pathway triggered by the activation of cell surface death receptors or an intrinsic pathway triggered by developmental cues and diverse intracellular stresses. This intrinsic pathway, also known as the stress pathway or mitochondrial pathway, is primarily regulated by the BCL-2 family, a class of key regulators of caspase activation consisting of anti-apoptotic (pro-survival) proteins having BH1-BH4 domains (BCL-2, i.e., the BCL-2 protein member of the BCL-2 anti-apoptotic protein family), BCL-xL, BCL-w, A1, MCL-1, and BCL-B); pro-apoptotic proteins having BH1, BH2, and BH3 domains (BAX, BAK, and BOK); and pro-apoptotic BH3-only proteins (BIK, BAD, BID, BIM, BMF, HRK, NOXA, and PUMA) (see, e.g., Cory et al., *Nature Reviews Cancer* 2:647-56 (2002); Cory et al., *Cancer Cell* 8:5-6 (2005); Adams et al., *Oncogene* 26:1324-1337 (2007)). BCL-2 anti-apoptotic proteins block activation of pro-apoptotic multi-domain proteins BAX and BAK (see, e.g., Adams et al., *Oncogene* 26:1324-37 (2007)).

As used herein, the term "BCL-2 inhibitor" refers to an agent that is capable of inhibiting one or more proteins in the BCL-2 family of anti-apoptotic proteins, e.g., BCL-2, BCL-xL, and BCL-w. In certain embodiments, a BCL-2 inhibitor of the disclosure inhibits one protein of the BCL-2 family selectively, e.g., a BCL-2 inhibitor may selectively inhibit BCL-2 and not BCL-xl or BCL-w.

The BCL-2 inhibitor described herein may inhibit one or more of BCL-2, BCL-xL, and BCL-w. In certain embodiments, the inhibitor of BCL-2 anti-apoptotic family of proteins inhibits BCL-2. In certain embodiments, the inhibitor of BCL-2 anti-apoptotic family of proteins inhibits BCL-2 and does not inhibit other members of the BCL-2 family of proteins, e.g., does not inhibit BCL-xL or BCL-w. In certain embodiments, the BCL-2 inhibitor is a BH3-mimetic.

In certain embodiments, the BCL-2 inhibitor of the disclosure inhibits BCL-xL function. In addition to inhibition of BCL-xL, the inhibitor may also interact with and/or inhibit one or more functions of BCL-2, e.g., BCL-xL/BCL-2 inhibitors. In certain embodiments, a BCL-2 inhibitor of the disclosure inhibits each of BCL-xL and BCL-w. In certain embodiments, a BCL-2 inhibitor of the disclosure inhibits BCL-xL, BCL-2, and BCL-w.

In certain embodiments, a BCL-2 inhibitor interferes with the interaction between the BCL-2 anti-apoptotic protein family member and one or more ligands or receptors to which the BCL-2 anti-apoptotic protein family member would bind in the absence of the inhibitor. In other embodiments, an inhibitor of one or more BCL-2 anti-apoptotic protein family members, wherein the inhibitor inhibits at least one BCL-2 protein specifically, binds only to one or more of BCL-xL, BCL-2, BCL-w and not to other Bcl-2 anti-apoptotic Bcl-2 family members, such as Mcl-1 and BCL2A1.

Binding affinity of a BCL-2 inhibitor for BCL-2 family proteins may be measured. By way of example, binding affinity of a BCL-xL inhibitor may be determined using a competition fluorescence polarization assay in which a fluorescent BAK BH3 domain peptide is incubated with BCL-xL protein (or other BCL-2 family protein) in the presence or absence of increasing concentrations of the BCL-XL inhibitor as previously described (see, e.g., U.S. Patent Publication 20140005190; Park et al, *Cancer Res.* 73:5485-96 (2013); Wang et al., *Proc. Natl. Acad, Sci USA* 97:7124-9 (2000); Zhang et al., *Anal. Biochem.* 307:70-5 (2002); Bruncko et al., *J. Med. Chem.* 50:641-62 (2007)). Percent inhibition may be determined by the equation: 1−[(mP value of well−negative control)/range)]×100%. Inhibitory constant ($K_i$) value is determined by the formula: $K_i = [I]_{50}/([L]_{50}/K_d + [P]_0/K_d + 1)$ as described in Bruncko et al., *J. Med. Chem.* 50:641-62 (2007) (see, also, Wang, *FEBS Lett.* 360:111-114 (1995)).

Examples of BCL-2 inhibitors include ABT-263 (4-[4-[[2-(4-chlorophenyl)-5,5-dimethylcyclohexen-1-yl]methyl]piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide or IUPAC, (R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3-((trifluoromethyl)sulfonyl)phenyl)sulfonyl)benzamide) (see, e.g., Park et al., 2008, *J. Med. Chem.* 51:6902; Tse et al., *Cancer Res.*, 2008, 68:3421; Int'l Patent Appl. Pub. No. WO 2009/155386; U.S. Pat. Nos. 7,390,799, 7,709,467, 7,906,505, 8,624,027) and ABT-737 (4-[4-[(4'-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]benzamide, Benzamide, 4-[4-[(4'-chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]- or 4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (see, e.g., Oltersdorf et al., *Nature*, 2005, 435:677; U.S. Pat. Nos. 7,973,161; 7,642,260).

In other embodiments, the BCL-2 inhibitor is a quinazoline sulfonamide compound (see, e.g., Sleebs et al., 2011, *J. Med. Chem.* 54:1914). In still another embodiment, the BCL-inhibitor is a small molecule compound as described in Zhou et al., *J. Med. Chem.*, 2012, 55:4664 (see, e.g., Compound 21 (R)-4-(4-chlorophenyl)-3-(3-(4-(4-(4-(4-(dimethylamino)-1-(phenylthio)butan-2-yl)amino)-3-nitrophenylsulfonamido)phenyl)piperazin-1-yl)phenyl)-5-ethyl-1-methyl-1H-pyrrole-2-carboxylic acid) and Zhou et al., *J. Med. Chem.*, 2012, 55:6149 (see, e.g., Compound 14 (R)-5-(4-Chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1-ethyl-2-methyl-1H-pyrrole-3-carboxylic acid; Compound 15 (R)-5-(4-Chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1-isopropyl-2-methyl-1H-pyrrole-3-carboxylic acid). In other embodiments, the BCL-inhibitor is a BCL-2/BCL-xL inhibitor such as BM-1074 (see, e.g., Aguilar et al., 2013, *J. Med. Chem.* 56:3048); BM-957 (see, e.g., Chen et al., 2012, *J. Med. Chem.* 55:8502); BM-1197 (see, e.g., Bai et al., *PLoS One* 2014 Jun. 5; 9(6):e99404. Doi: 10.1371/journal.pone. 009904); U.S. Patent Appl. No. 2014/0199234; N-acylsulfonamide compounds (see, e.g., Int'l Patent Appl. Pub. No. WO 2002/024636, Int'l Patent Appl. Pub. No. WO 2005/049593, Int'l Patent Appl. Pub. No. WO 2005/049594, U.S. Pat. Nos. 7,767,684, 7,906,505). In still another embodiment, the BCL-2 inhibitor is a small molecule macrocyclic compound (see, e.g., Int'l Patent Appl. Pub. No. WO 2006/127364, U.S. Pat. No. 7,777,076). In yet another embodiment, the BCL-2 inhibitor is an isoxazolidine compound (see, e.g., Int'l Patent Appl. Pub. No. WO 2008/060569, U.S. Pat. Nos. 7,851,637, 7,842,815). In yet another embodiment, the BCL-2 inhibitor is 544563 (see, e.g., Loriot et. al., *Cell Death and Disease*, 2014, 5, e1423). In one embodiment, the BCL-2 inhibitor is (R)-3-((4'-chloro-[1,1'-biphenyl]-2-yl)methyl)-N-((4-(((R)-4-(dimethylamino)-1-(phenylthio)butan-2-yl)amino)-3-nitrophenyl)sulfonyl)-2,3,4,4a,5,6-hexahydro-1H-pyrazino[1,2-a]quinoline-8-carboxamide. In another embodiment, the BCL-2 inhibitor is a small molecule heterocyclic compounds (see, e.g., U.S. Pat. No. 9,018,381).

In certain cases, a BCL-2 inhibitor is used in combination with a compound or salt of Formula I, Ia or Ib. Any BCL-2 inhibitor may be used and may exhibit a synergistic effect when used in combination with a compound or salt of Formula I, Ia or Ib. A BCL-2 family inhibitor may inhibit one or more members of the BCL-2 family, including Bcl-2, Bcl-xL, Bcl-w, BAK1, BAX, BCL2, BCL2A1, BCL2L1, BCL2L2, BCL2L10, BCL2L13, BCL2L14, BOK and MCL1. In certain embodiments, a compound or salt of Formula I, Ia or Ib is used in combination with any of the following: navitoclax, venetoclax, A-1155463, A-1331852, ABT-737, obatoclax, TW-37, A-1210477, AT101, HA14-1, BAM7, sabutoclax, UMI-77, gambogic acid, maritoclax, MIM1, methylprednisolone, iMAC2, Bax inhibitor peptide V5, Bax inhibitor peptide P5, Bax channel blocker, and ARRY 520 trifluoroacetate. In some examples, voruciclib is used in combination with navitoclax. In certain embodiments, voruciclib is used in combination with venetoclax.

In some embodiments, a BCL-2 inhibitor is used in combination with a CDK inhibitor of the disclosure, e.g., a compound of Formula I, Ia or Ib, for the treatment of a blood cancer. In certain embodiments, the blood cancer is leukemia, such as acute myeloid leukemia (AML), chronic myeloid leukemia (CML), acute lymphocytic lymphoma (ALL), and chronic lymphocytic leukemia (CLL). In certain embodiments, the blood cancer is a non-Hodgkin lymphoma, such as B-cell or T-cell lymphoma. B-cell lymphomas include diffuse large B-cell lymphoma (DLBCL), primary mediastinal B-cell lymphoma, intravascular large B-cell lymphoma, follicular lymphoma, small lymphocytic lymphomia (SLL), mantle cell lymphoma, marginal zone B-cell lymphomas, extranodal marginal zone B-cell lymphomas, nodal marginal zone B-cell lymphoma, splenic marginal zone B-cell lymphoma, Burkitt lymphoma, lymphoplasmacytic lymphoma, and primary central nervous system lymphoma. T-cell lymphomas include precursor T-lymphoblastic lymphoma, peripheral T-cell lymphomas, cutaneous T-cell lymphomas, adult T-cell lymphoma with subtypes: smoldering chronic, acute, and lymphoma, angio-immunoblastic T-cell lymphoma, extranodal natural killer/T-cell lymphoma, nasal type, enteropathy-associated intestinal T-cell lymphoma (EATL) with subtypes I and II, and anaplastic large cell lymphoma (ALCL). Combinations of the present disclosure, e.g., combinations of CDK inhibitors and BCL-2 inhibitors described herein, may be used to treat a blood cancer described herein.

The terms "treat," "treating" or "treatment," as used herein, may include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The disclosure provides methods of preventing, or reducing, a relapse of a cancer in a subject in need thereof. In certain embodiments, the term "prevent" or "preventing" as related to a disease or disorder may refer to a compound or combination that, in a statistical sample, reduces the occurrence of the disorder or condition in the treated sample relative to an untreated control sample, or delays the onset or reduces the severity of one or more symptoms of the disorder or condition relative to the untreated control sample. The method includes administering a combination therapy described herein to treat minimal residual disease, and/or as maintenance therapy, e.g., as a prolonged or extended therapy after cessation of another cancer treatment. For example, the combination therapy may be administered after cessation of another cancer therapy, such as chemotherapy, radiation therapy and/or surgery.

In certain aspects, a proteasome inhibitor may be combined or used in combination with a CDK inhibitor of the disclosure, e.g., a compound or salt of any one of Formulas I, Ia, or Ib. In eukaryotic cells, the ubiquitin (Ub)-proteasome pathway (UPS) involves Ub modification and subsequent degradation of protein substrates. UPS controls the levels of many cellular regulatory proteins, including transcription factors, cell cycle regulatory proteins and factors participating in a variety of cellular processes. The common feature of UPS pathway is that the highly conserved Ub is covalently attached to the target proteins through a series of enzymes, namely E1 Ub-activating enzyme, E2 Ub-conjugating enzyme and E3 Ub ligase. The E1 first activates Ub and transfers it to E2. From the E2 enzyme, the Ub is transferred directly to the target protein or indirectly through an E3 Ub ligase. The polyubiquitylated protein is recognized and degraded by 26S proteasome, a large complex with multiple proteolytic activities.

As used herein, the term "proteasome inhibitor" refers to an agent that blocks the action of a proteasome. Proteasome inhibition may prevent degradation of pro-apoptotic factors such as the p53 protein, permitting activation of programmed cell death in neoplastic cells dependent upon suppression of pro-apoptotic pathways.

Any proteasome inhibitor may be used and may exhibit a synergistic effect when used in combination with a CDK inhibitor, e.g., a compound or salt of Formula I, Ia, or Ib. Non-limiting examples of proteasome inhibitors may include: bortezomib, marizomib, ixazomib, disulfiram, epigallocatechin-3-gallate, salinosporamide A, carfilzomib, ONX 0912, CEP-18770, MLN9708, epoxomicin, and MG132.

In some embodiments, a proteasome inhibitor is used in combination with a CDK inhibitor of the disclosure, e.g., a compound of Formula I, Ia or Ib, for the treatment of a blood cancer, such as diffuse large B-cell lymphoma or triple negative breast cancer.

In some aspects, combinations described herein, e.g., combinations of CDK inhibitors with BCL-2 inhibitors or proteasome inhibitors, can be utilized for the treatment of cancer. A combination therapy described herein can reduce the likelihood of metastasis in a subject in need thereof. In some embodiments, the metastasis is a solid tumor. In some embodiments, the metastasis is a liquid tumor. Cancers that are liquid tumors can be those that occur, for example, in blood, bone marrow, and lymph nodes, and can include, for example, leukemia, myeloid leukemia, lymphocytic leukemia, lymphoma, Hodgkin's lymphoma, melanoma, and multiple myeloma. Leukemias include, for example, acute lymphoblastic leukemia (ALL), acute myeloid leukemia (AML), chronic lymphocytic leukemia (CLL), chronic myelogenous leukemia (CML), and hairy cell leukemia. Cancers that are solid tumors include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer, squamous cell skin cancer, renal cancer, head and neck cancers, throat cancer, squamous carcinomas that form on the moist mucosal linings of the nose, mouth, throat, bladder cancer, osteosarcoma, cervical cancer, endometrial cancer, esophageal cancer, liver cancer, and kidney cancer. In some embodiments, the condition treated by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

The methods described herein can also be used for inhibiting progression of metastatic cancer tumors. Non-limiting examples of cancers include adrenocortical carcinoma, childhood adrenocortical carcinoma, AIDS-related cancers, anal cancer, appendix cancer, basal cell carcinoma, childhood basal cell carcinoma, bladder cancer, childhood bladder cancer, bone cancer, brain tumor, childhood astrocytomas, childhood brain stem glioma, childhood central nervous system atypical teratoid/rhabdoid tumor, childhood central nervous system embryonal tumors, childhood central nervous system germ cell tumors, childhood craniopharyngioma brain tumor, childhood ependymoma brain tumor, breast cancer, childhood bronchial tumors, carcinoid tumor, childhood carcinoid tumor, gastrointestinal carcinoid tumor, carcinoma of unknown primary, childhood carcinoma of unknown primary, childhood cardiac tumors, cervical cancer, childhood cervical cancer, childhood chordoma, chronic myeloproliferative disorders, colon cancer, colorectal cancer, childhood colorectal cancer, extrahepatic bile duct cancer, ductal carcinoma in situ (DCIS), endometrial cancer, esophageal cancer, childhood esophageal cancer, childhood esthesioneuroblastoma, eye cancer, malignant fibrous histiocytoma of bone, gallbladder cancer, gastric (stomach) cancer, childhood gastric cancer, gastrointestinal stromal tumors (GIST), childhood gastrointestinal stromal tumors (GIST), childhood extracranial germ cell tumor, extragonadal germ cell tumor, gestational trophoblastic tumor, glioma, head and neck cancer, childhood head and neck cancer, hepatocellular cancer, hypopharyngeal cancer, kidney cancer, renal cell kidney cancer, Wilms tumor, childhood kidney tumors, Langerhans cell histiocytosis, laryngeal cancer, childhood laryngeal cancer, leukemia, acute lymphoblastic leukemia (ALL), acute myeloid leukemia (AML), chronic lymphocytic leukemia (CLL), chronic myelogenous leukemia (cml), hairy cell leukemia, lip cancer, liver cancer (primary), childhood liver cancer (primary), lobular carcinoma in situ (LCIS), lung cancer, non-small cell lung cancer, small cell lung cancer, lymphoma, AIDS-related lymphoma, burkitt lymphoma, cutaneous t-cell lymphoma, Hodgkin lymphoma, non-Hodgkin lymphoma, primary central nervous system lymphoma (CNS), melanoma, childhood melanoma, intraocular melanoma, Merkel cell carcinoma, malignant mesothelioma, childhood malignant mesothelioma, metastatic squamous neck cancer with occult primary, midline tract carcinoma involving NUT gene, mouth cancer, childhood multiple endocrine neoplasia syndromes, mycosis fungoides, myelodysplastic syndromes, myelodysplastic neoplasms, myeloproliferative neoplasms, multiple myeloma, nasal cavity cancer, nasopharyngeal cancer, childhood nasopharyngeal cancer, neuroblastoma, oral cancer, childhood oral cancer, oropharyngeal cancer, ovarian cancer, childhood ovarian cancer, epithelial ovarian cancer, low malignant potential tumor ovarian cancer, pancreatic cancer, childhood pancreatic cancer, pancreatic neuroendocrine tumors (islet cell tumors), childhood papillomatosis, paraganglioma, paranasal sinus cancer, parathyroid cancer, penile cancer, pharyngeal cancer, pheochromocytoma, pituitary tumor, plasma cell neoplasm, childhood pleuropulmonary blastoma, prostate cancer, rectal cancer, renal pelvis transitional cell cancer, retinoblastoma, salivary gland cancer, childhood salivary gland cancer, Ewing sarcoma family of tumors, Kaposi Sarcoma, osteosarcoma, rhabdomyosarcoma, childhood rhabdomyosarcoma, soft tissue sarcoma, uterine sarcoma, Sézary syndrome, childhood skin cancer, nonmelanoma skin cancer, small intestine cancer, squamous cell carcinoma, childhood squamous cell carcinoma, testicular cancer, childhood testicular cancer, throat cancer, thymoma and thymic carcinoma, childhood thymoma and thymic carcinoma, thyroid cancer, childhood thyroid cancer, ureter transitional cell cancer, urethral cancer, endometrial uterine cancer, vaginal cancer, vulvar cancer, and Waldenström macroglobulinemia.

The combination therapies described herein may be used together with other therapies such as radiation therapy. Chemotherapy and radiotherapy treatment regimens can comprise a finite number of cycles of on-drug therapy followed by off-drug therapy, or comprise a finite timeframe in which the chemotherapy or radiotherapy is administered. The protocols can be determined by clinical trials, drug labels, and clinical staff in conjunction with the subject to be treated. The number of cycles of a chemotherapy or radiotherapy or the total length of time of a chemotherapy or radiotherapy regimen can vary depending on the subject's response to the cancer therapy. A pharmaceutical agent described herein can be administered after the treatment regimen of chemotherapy or radiotherapy has been completed.

In some aspects, the combinations described herein can be utilized to treat a subject in need thereof. In some cases, the subject to be treated by methods and compositions disclosed herein can be a human subject. A subject to be treated by methods and compositions disclosed herein can be a non-human animal. Non-limiting examples of non-human animals can include a non-human primate, a livestock animal, a domestic pet, and a laboratory animal.

In certain embodiments, the combination therapies described herein may be administered as separate agents or may be combined into a single pharmaceutical composition. For example, a combination of a CDK inhibitor, e.g., a compound or salt of Formula I, Ia, or Ib, and a BCL-2 inhibitor, e.g., venetoclax or navitoclax, may be formulated as two separate pharmaceutical compositions or the two agents may be co-formulated as a single pharmaceutical composition.

In certain embodiments, a CDK inhibitor, e.g., a compound or salt of Formula I, Ia, or Ib, is co-formulated with a BCL-2 inhibitor or proteasome inhibitor. In some cases, a compound of Formula I, Ia, or Ib is co-formulated with any one of navitoclax, venetoclax, bortezomib, marizomib or ixazomib or a combination thereof.

In certain embodiments, the disclosure provides a pharmaceutical composition, e.g., for oral or parenteral administration, comprising a compound or salt of Formula I, Ia, or Ib. In some aspects, the pharmaceutical composition comprises a compound or salt of Formula I, Ia, or Ib in an amount of at least about 1 mg to about 1000 mg, from about 100 mg to about 400 mg, from about 100 mg to about 200 mg, from about 200 mg to about 400 mg, or from about 250 mg to about 350 mg. For example, a pharmaceutical composition of the disclosure may comprise about 100 mg, about 120 mg, about 140 mg, about 160 mg, about 180 mg, about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg of a compound of Formula I, Ia, or Ib. For a compound described herein, e.g., a compound of Formula Ib, formulated into a pharmaceutical composition in the form of a salt, the amount of the compound may reflect the free base weight and not the weight of the salt form. In certain embodiments, the pharmaceutical composition of the compound or salt of Formula I, Ia, or Ib does not include an additional anticancer agent, e.g., a BCL-2 inhibitor or proteasome inhibitor. In certain embodiments, the pharmaceutical composition includes an additional anticancer agent, e.g., a BCL-2 inhibitor or proteasome inhibitor.

A therapeutically effective amount of a compound of the disclosure, e.g., a compound or salt of Formula I, Ia, or Ib, can be expressed as mg of the compound per kg of subject body mass. In some instances, a dose of a therapeutically effective amount may be at least about 0.1 mg/kg to about 20 mg/kg, for example, about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, or about 20 mg/kg. For a compound described herein, e.g., a compound of Formula Ib, formulated into a pharmaceutical composition in the form of a salt, the therapeutically effective amount of the compound may reflect the free base weight and not the weight of the salt form.

In certain embodiments, the disclosure provides a pharmaceutical composition, e.g., for oral or parenteral administration, comprising a BCL-2 inhibitor, e.g., venetoclax or navitoclax. The pharmaceutical composition may comprise a BCL-2 inhibitor in an amount of at least about 1 mg to about 1000 mg, from about 100 mg to about 1000 mg, from about 100 mg to about 800 mg, from about 200 mg to about 800 mg, or from about 300 mg to about 8000 mg. For example, a pharmaceutical composition of the disclosure may comprise about 100 mg, about 120 mg, about 140 mg, about 160 mg, about 180 mg, about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, about 500 mg, about 520 mg, about 540 mg, about 560 mg, about 580 mg, about 600 mg, about 620 mg, about 640 mg, about 660 mg, about 680 mg, about 700 mg, about 720 mg, about 740 mg, about 760 mg, about 780 mg, about 800 mg, about 820 mg, about 840 mg, about 860 mg, about 880 mg, about 900 mg, about 920 mg, about 940 mg, about 960 mg, about 980 mg, or about 1000 mg of a BCL-2 inhibitor, e.g., venetoclax or navitoclax.

In certain embodiments, the disclosure provides a pharmaceutical composition, e.g., for oral or parenteral administration, comprising a proteasome inhibitor, e.g., bortezomib, marizomib, or ixazomib. The pharmaceutical composition may comprise a proteasome inhibitor in an amount of at least about 0.5 mg to about 50 mg, from about 1 mg to about 30 mg, from about 1 mg to about 20 mg, from about 1 mg to about 10 mg, or from about 1 mg to about 5 mg. For example, a pharmaceutical composition of the disclosure may comprise about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg of a proteasome inhibitor, e.g., bortezomib, marizomib, or ixazomib.

In certain embodiments, formulations of the disclosure comprise a compound or salt of Formula I, Ia, or Ib, a BCL-2 inhibitor or a proteasome inhibitor, wherein the compound or salt is about 70% to about 99.99%, about 80% to about 99.9%, about 85% to about 99%, about 90% to about 99%, about 95% to about 99%, about 97% to about 99%, about 98% to about 99%, about 98% to about 99.9%, about 99% to about 99.99%, about 99.5% to about 99.99%, about 99.6% to about 99.99%, about 99.8 to about 99.99%, or about 99.9% to about 99.99% free of impurities.

In certain embodiments, a pharmaceutical composition of the disclosure comprises both a compound or salt of Formula I, Ia, or Ib and a BCL-2 inhibitor in amounts such as the ones described herein, e.g., a pharmaceutical composition with 100 to 400 mg of a compound or salt of Formula Ib and 200 to 800 mg of a BCL-2 inhibitor, e.g., venetoclax.

In certain embodiments, a pharmaceutical composition of the disclosure comprises both a compound or salt of Formula I, Ia, or Ib and a proteasome inhibitor in amounts such as the ones described herein, e.g., a pharmaceutical composition with 100 to 400 mg of a compound or salt of Formula Ib and 1 to 10 mg of a proteasome inhibitor, e.g., ixazomib.

Pharmaceutical compositions disclosed herein may be in the form of a liquid formulation, a solid formulation or a combination thereof. Non-limiting examples of formulations may include a tablet, a capsule, a pill, a gel, a paste, a liquid solution and a cream. In some instances, the therapeutic agent, e.g., compound or salt of Formula I, Ia, or Ib, BCL-2 inhibitor or proteasome inhibitor, may be in a crystallized form. In pharmaceutical compositions comprising two or more therapeutic agents, each agent may be crystallized separately and then combined or they may be crystallized together. Compositions may comprise two or more therapeutic agents in one or more physical state. For example, a composition may be a tablet comprising one therapeutic agent in a solid formulation and another therapeutic agent or drug in a gel formulation. In certain embodiments, the composition is a single pharmaceutical composition comprising a compound or salt of Formula I, Ia, or Ib in a first physical state and a BCL-2 family inhibitor or a proteasome inhibitor in a second physical state.

The compositions of the present disclosure may further comprise an excipient or an additive. Excipients may include any and all solvents, coatings, chelating agents, flavorings, colorings, lubricants, disintegrants, preservatives, sweeteners, anti-foaming agents, buffering agents, polymers, antioxidants, binders, diluents, and vehicles (or carriers). Generally, the excipient is compatible with the therapeutic compositions of the present disclosure.

Liquid preparations for oral administration can take the form of, for example, solutions, syrups or suspensions, or they can be presented as a dry product for reconstitution with water or other suitable vehicles before use. Such liquid preparations can be prepared by conventional approaches with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

This disclosure further encompasses anhydrous compositions and dosage forms comprising an active ingredient, since water can facilitate the degradation of some compounds. Anhydrous compositions and dosage forms of the present disclosure can be prepared using anhydrous or low moisture containing ingredients and low moisture or low humidity conditions. Compositions and dosage forms of the present disclosure which contain lactose can be made anhydrous if substantial contact with moisture and/or humidity during manufacturing, packaging, and/or storage is expected. An anhydrous composition can be prepared and stored such that its anhydrous nature is maintained. Accordingly, anhydrous compositions can be packaged using materials that prevent exposure to water such that they can be included in suitable formulary kits. Examples of suitable packaging include, but are not limited to, hermetically sealed foils, plastic, unit dose containers, blister packs, and strip packs.

An ingredient described herein can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Binders suitable for use in dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

When aqueous suspensions and/or elixirs are desired for oral administration, the active ingredient therein can be combined with various sweetening or flavoring agents, coloring matter or dyes and, if so desired, emulsifying and/or suspending agents, together with such diluents as water, ethanol, propylene glycol, glycerin and various combinations thereof.

In one embodiment, the composition can include a solubilizer to ensure good solubilization and/or dissolution of the compound of the present disclosure and to minimize precipitation of the compound of the present disclosure. This can be especially important for compositions for non-oral use, e.g., compositions for injection. A solubilizer can also be added to increase the solubility of the hydrophilic drug and/or other components, such as surfactants, or to maintain the composition as a stable or homogeneous solution or dispersion.

Pharmaceutical compositions described herein may be suitable for oral administration to a subject in need thereof. In some cases, slow release formulations for oral administration may be prepared in order to achieve a controlled release of the active agent in contact with the body fluids in the gastrointestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

In some embodiments, the compositions can be formulated in a food composition. For example, the compositions can be a beverage or other liquids, solid food, semi-solid food, with or without a food carrier. For example, the compositions can include a black tea supplemented with any of the compositions described herein. The composition can be a dairy product supplemented any of the compositions described herein. In some embodiments, the compositions can be formulated in a food composition. For example, the compositions can comprise a beverage, solid food, semi-solid food, or a food carrier.

In certain embodiments, the pharmaceutical formulations can be in a form suitable for parenteral injection as a sterile suspension, solution, or emulsion in oily or aqueous vehicles, and can contain formulation agents such as suspending, stabilizing, and/or dispersing agents. Pharmaceutical formulations for parenteral administration include, for example, aqueous solutions of the active compounds in water-soluble form. Suspensions of the active compounds can be prepared, for example, as oily injection suspensions. Suitable lipophilic solvents or vehicles include fatty oils such as sesame oil, or synthetic fatty acid esters, such as ethyl oleate, isopropyl palmitate, or medium chain triglycerides, or liposomes. In preferred embodiments, a formulation for parenteral administration is an aqueous suspension.

The compound described herein may be present in a composition within a range of concentrations, the range being defined by an upper and lower value selected from any of the preceding concentrations. For example, the compound or salt of the disclosure may be present in the formulation at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

Methods for the preparation of compositions comprising the compounds described herein can include formulating the compounds with one or more inert, pharmaceutically-acceptable excipients. Liquid compositions include, for example, solutions in which a compound is dissolved, emulsions comprising a compound, or a solution containing liposomes, micelles, or nanoparticles comprising a compound as disclosed herein. These compositions can also contain minor amounts of nontoxic, auxiliary substances, such as wetting or emulsifying agents, pH buffering agents, and other pharmaceutically-acceptable additives.

Formulations for injection can be presented in unit dosage form, for example, in ampoules or in multi-dose containers, with an added preservative. The compositions can take such forms as suspensions, solutions or emulsions in oily or aqueous vehicles, and can contain formulatory agents such as suspending, stabilizing and/or dispersing agents. The compositions can be presented in unit-dose or multi-dose containers, for example sealed ampoules and vials, and can be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Pharmaceutical formulations for parenteral administration include aqueous and non-aqueous (oily) sterile injection solutions of the active compounds which can contain antioxidants, buffers, bacteriostats and solutes which render the formulation isotonic with the blood of the intended recipient; and aqueous and non-aqueous sterile suspensions which can include suspending agents and thickening agents. Suitable lipophilic solvents or vehicles include fatty oils such as sesame oil, or synthetic fatty acid esters, such as ethyl oleate or triglycerides, or liposomes.

A composition described herein, e.g., a pharmaceutical composition of a compound or salt of Formula I, Ia, or Ib, or a BCL-2 inhibitor or a proteasome inhibitor or a co-formulation of a compound of Formula I, Ia, or Ib with a BCL-2 inhibitor or proteasome inhibitor, can be administered once or more than once each day. The composition may be administered serially (e.g., taken every day without a break for the duration of the treatment regimen). In some cases, the treatment regime can be less than a week, a week, two weeks, three weeks, a month, or greater than a month. In some cases, a composition of the disclosure is administered over a period of at least 12 weeks. In other cases, the composition is administered for a day, at least two consecutive days, at least three consecutive days, at least four consecutive days, at least five consecutive days, at least six consecutive days, at least seven consecutive days, at least eight consecutive days, at least nine consecutive days, at least ten consecutive days, or at least greater than ten consecutive days. In some cases, a therapeutically effective amount can be administered one time per week, two times per week, three times per week, four times per week, five times per week, six times per week, seven times per week, eight times per week, nine times per week, 10 times per week, 11 times per week, 12 times per week, 13 times per week, 14 times per week, 15 times per week, 16 times per week, 17 times per week, 18 times per week, 19 times per week, 20 times per week, 25 times per week, 30 times per week, 35 times per week, 40 times per week, or greater than 40 times per week. In some cases, a therapeutically effective amount can be administered one time per day, two times per day, three times per day, four times per day, five times per day, six times per day, seven times per day, eight times per day, nine times per day, 10 times per day, or greater than 10 times per day. In some cases, the composition is administered at least twice a day. In further cases, the composition is administered at least every hour, at least every two hours, at least every three hours, at least every four hours, at least every five hours, at least every six hours, at least every seven hours, at least every eight hours, at least every nine hours, at least every 10 hours, at least every 11 hours, at least every 12 hours, at least every 13 hours, at least every 14 hours, at least every 15 hours, at least every 16 hours, at least every 17 hours, at least every 18 hours, at least every 19 hours, at least every 20 hours, at least every 21 hours, at least every 22 hours, at least every 23 hours, or at least every day.

Pharmaceutical compositions of the disclosure can be administered either acutely or chronically. Pharmaceutical compositions of the invention can be administered as a single treatment or as a course of treatment. Treatments can be administered once per day, twice per day, three times per day, in the morning, in the evening, before sleeping, or continuously throughout the day. Treatments can be applied every day, every other day, every three days, twice weekly, once weekly, every other week, monthly, every six weeks, every other month, every three months, every six months, annually, every other year, every 5 years, or as required.

In certain embodiments, the dose of drug being administered may be temporarily reduced or temporarily suspended for a certain length of time. In certain embodiments, the patient will have a drug holiday wherein the patient does not receive the drug or receives a reduced amount of the drug for a period of time. A drug holiday can be, for example, between 2 days and 1 year, including by way of example only, 2 days, 3 days, 4 days, 5 days, 6 days, 7 days, 10 days, 12 days, 15 days, 20 days, 28 days, or more than 28 days. A drug holiday may be for about 1 month, about 2 months, about 3 months, about 4 months, about 5 months, about 6 months, about 7 months, about 8 months, about 9 months, about 10 months, about 11 months or about 12 months. The dose reduction during a drug holiday can be, for example, by 10%-100% of the original administered dose, including by way of example only 10%, 15%, 20%, 25%, 30%, 35%, 40%, 45%, 50%, 55%, 60%, 65%, 70%, 75%, 80%, 85%, 90%, 95%, and 100%. For further examples the dose reduction can be between 10% and 100%, between 20% and 80%, between 30% and 70%, between 50% and 90%, between 80% and 100% or between 90% and 100%.

Once improvement of the patient's conditions has occurred, a maintenance dose can be administered if necessary. Subsequently, the dosage or the frequency of administration, or both, can be reduced, as a function of the symptoms, to a level at which the improved disease, disorder or condition can be retained.

Additional methods for administering the formulations described herein include, for example, limited to delivery via enteral routes including oral, gastric or duodenal feeding tube, rectal suppository, rectal enema, parenteral routes, injection, infusion, intraarterial, intracardiac, intradermal, intraduodenal, intramedullary, intramuscular, intraosseous, intraperitoneal, intrathecal, intravascular, intravenous, intravitreal, intracameral, epidural, subcutaneous, inhalational, transdermal, transmucosal, sublingual, buccal, topical, epicutaneous, dermal, enemaear drops, intranasal, and vaginal administration. The compounds described herein can be administered locally to the area in need of treatment, by for example, local infusion during surgery, topical application such as creams or ointments, injection, catheter, or implant. The administration can also be by direct injection at the site of a diseased tissue or organ.

The length of the period of administration and/or the dosing amounts can be determined by a physician or any other type of clinician. The physician or clinician can observe the subject's response to the administered compositions and adjust the dosing based on the subject's performance. For example, dosing for subjects that show reduced effects in energy regulation can be increased to achieve desired results.

In some embodiments, the combination therapies described herein can be administered together at the same time in the same route, or administered separately. In some embodiments, the components in the compositions can be administered using the same or different administration routes.

In some embodiment, the disclosure also provides for methods of manufacturing the compositions described herein. In some embodiments, the manufacture of a composition described herein comprises mixing or combining two or more components.

In some embodiments, the compositions can be combined or mixed with a pharmaceutically active or therapeutic agent, a carrier, and/or an excipient. Examples of such components are described herein. The combined compositions can be formed into a unit dosage as tablets, capsules, gel capsules, slow-release tablets, or the like.

In some embodiments, the composition is prepared such that a solid composition containing a substantially homogeneous mixture of the one or more components is achieved, such that the one or more components are dispersed evenly throughout the composition so that the composition can be readily subdivided into equally effective unit dosage forms such as tablets, pills and capsules.

A unit dose may be packaged into a container to be transferred to the user. A unit dose may be packaged in a tube, a jar, a box, a vial, a bag, a tray, a drum, a bottle, a syringe, or a can.

Another aspect of the disclosure provides for achieving desired effects in one or more subjects after administration of a combination composition described herein for a specified time period. For example, the beneficial effects of the compositions described herein can be observed after administration of the compositions to the subject for 1, 2, 3, 4, 6, 8, 10, 12, 24, or 52 weeks.

In certain embodiments, the combination therapies described herein may be administered by a combination treatment regimen. A combination treatment regimen can encompass treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. The disclosure also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

In certain embodiments, the combination therapy can provide a therapeutic advantage in view of the differential toxicity associated with the two treatment modalities. For example, treatment with CDK inhibitors such as those described herein can lead to a particular toxicity that is not seen with the anticancer agent, e.g., BCL-2 inhibitor or proteasome inhibitor, and vice versa. As such, this differential toxicity can permit each treatment to be administered at a dose at which said toxicities do not exist or are minimal, such that together the combination therapy provides a therapeutic dose while avoiding the toxicities of each of the constituents of the combination agents. Furthermore, when the therapeutic effects achieved as a result of the combination treatment are synergistic, the doses of each of the agents can be reduced even further, thus lowering the associated toxicities to an even greater extent.

The compounds described herein or the pharmaceutically acceptable salts thereof, as well as combination therapies, may be administered before, during or after the occurrence of a disease or condition, and the timing of administering the composition containing a compound varies. The compounds described herein can be used as a prophylactic and may be administered continuously to subjects with a propensity to develop conditions or diseases in order to prevent the occurrence of the disease or condition. The compounds described herein and compositions thereof may be administered to a subject during or as soon as possible after the onset of the symptoms. A compound described herein may be administered as soon as is practicable after the onset of a disease or condition is detected or suspected, and for a length of time necessary for the treatment of the disease.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

For all in vitro drug mechanism-of-action studies, the materials and methods outlined below were used.

Cell lines shown in Table 1, adherent or suspension, were treated in 6-well dishes or T10 flasks respectively, seeded at one million per ml density prior to treatment in total volumes of 3-10 ml. All agents used for in vitro cell treatments were formulated in water/DMSO to achieve required concentrations (as stated in respective figure labels/legends) with DMSO concentrations not exceeding 0.01%. Drug sources are indicated in table under 'CIVO microinjection studies'. Cells were harvested at experimental time points: 2, 6, or 24 hours post treatment as indicated in respective figures, first by washing cells twice in ice-cold PBS in 15 ml falcon tubes, centrifugation at 1000 rpm for 5 mins followed by lysis of the respective cell pellets as described in section below. Note: Drug resistant NUDHL1 Dox 1000 nM and Toledo Dox 1000 nM cell lines were generated at Presage by culturing parental lines in media with stepwise increments in Doxorubicin concentration over several passages. These cells were used to generate xenografts when resistance to 1 uM Dox was achieved.

TABLE 1

| DLBCL cell lines | | Culture conditions in 5% |
|---|---|---|
| Cell line Name | Vendor | CO2/37 deg C. |
| RIVA (or RI-1) | DSMZ, Germany | RPMI 1640 (Thermofisher) + 10% FBS |
| SU-DHL-4 | ATCC, USA | RPMI 1640 (Thermofisher) + 10% FBS |
| U2932 | DSMZ | RPMI 1640 (Thermofisher) + 10% FBS |
| NUDHL1 | DSMZ | RPMI 1640 (Thermofisher) + 10% FBS |
| TOLEDO | DSMZ | RPMI 1640 (Thermofisher) + 10% FBS |
| OCI Ly 10 | UHN, Princess Margaret Hospital, Canada | IMDM (Thermofisher) + 20% human serum (Valley biomedical)- fresh media every passage |
| TNBC cell line | | |
| HCC1187 | ATCC | RPMI 1640 (Thermofisher) + 10% FBS |
| AML cell lines | | |
| SKM1 | DSMZ | RPMI 1640 (Thermofisher) + 10% FBS |
| MV-4-11 | ATCC | IMDM (Thermofisher) + 20% human serum (Valley biomedical) |
| OCI AML3 | DSMZ | RPMI 1640 (Thermofisher) + 10% FBS |

For all Western Blot Analysis studies, the materials and methods outlined below were used.

Protein lysates were prepared by adding ice-cold 1×RIPA Buffer (from 10×, Millipore) with 1×-3× Halt protease and phosphatase inhibitor cocktail (100×, Pierce) to cell pellets, followed by pulse sonication (~3-5 secs) three times. Lysates were cleared by centrifugation at 14K rpm for 15-20 mins and the supernatant (lysate) was collected for further analysis. To prepare lysates from cryopreserved xenograft tumor tissue, tissue was first homogenized using a hand-held tissue homogenizer (Cole Palmer) in above lysis buffer followed by pulse sonication and centrifugation as described above. Above steps were carried out under ice cold conditions. Protein samples were quantified using Bradford assay (Biorad) at 1:10 or higher dilutions using appropriate blank controls with 1×RIPA. 20-25 micrograms of protein from each sample were subject to SDS-PAGE using BOLT 4-12% Bis-Tris gels (Thermofisher) and transferred to either 0.45 or 0.2 micron pore size membranes (as applicable based on protein molecular size), and either nitrocellulose (NC) or pvdf (Thermofisher) using manufacturer's protocol, blocked for one hour in 5% milk at room temperature, probed with primary antibodies (Table 2) at 4 deg C. overnight and corresponding HRP-conjugated secondary antibodies (Jackson Immunoresearch, 1:10,000-1:20,000 dilutions) for 1 hour at room temperature. Three PBS/0.01% Tween-20 washes (5-10 mins each) were carried out after each antibody incubation. ECL chemiluminescent substrate (Pierce or GE) and autoradiographic film (Thermofisher) was used for detection of protein signals.

TABLE 3

| Cell line | Source | Inoculation cell # per mouse | Mouse strain |
|---|---|---|---|
| DLBCL and AML xenografts | | | |
| RIVA (or RI-1) | DSMZ | $5 \times 10^6$ million | NOD SCID (Envigo) |
| SU-DHL-4 | ATCC | $5 \times 10^6$ million | SCID Beige (Charles River/Envigo) |
| U2932 | DSMZ | $5 \times 10^6$ million | NOD SCID (Envigo) |
| SKM1 (AML) | DSMZ | $5 \times 10^6$ million | NOD SCID (Envigo) |
| NUDHL1 | DSMZ | $5 \times 10^6$ million | NOD SCID (Envigo) |
| TOLEDO | DSMZ | $5 \times 10^6$ million | NOD SCID (Envigo) |
| TNBC xenografts | | | |
| HCC1187 | ATCC | $5 \times 10^6$ million | Athymic nude (Envigo) |

TABLE 2

| Primary antibody | Species | Vendor/Cat No. | Dilution/diluent |
|---|---|---|---|
| DLBCL and AML experiments | | | |
| cPARP | Rabbit | CST 5625 | 1:1000 for NC (or 1:4000 for pvdf membranes) in 5% milk |
| MCL1 | Rabbit | CST 39224; CST 5453 | 1:1000 for NC (or 1:4000 for pvdf membranes) in 5% milk |
| cMYC | Rabbit | Ab32072 | 1:10,000 (pvdf) in 5% milk |
| P53 | Rabbit | CST 2527 and CST 9282 | 1:4000 (pvdf) in 5% milk |
| phospho RNA pol II (Ser 2) | Rat | Active Motif 61083 | 1:1000 (pvdf) in 5% BSA/PBS |
| beta actin (loading control) | Mouse | CST 12262 | 1:40,000 (pvdf) in 5% milk |
| BCL2 | Mouse | Dako M0887 | 1:5000 (pvdf) in 5% milk |
| TNBC experiments Primary antibody | Species | Vendor | Dilution |
| XBP1s | Rabbit | CST 12782 | 1:1000 (NC) in 5% milk |
| XIAP | Rabbit | CST 2042 | 1:1000 (NC) in 5% milk |
| MCL1 | Rabbit | CST 94296 | 1:1000 (NC) in 5% milk |
| beta actin (loading control) | Mouse | Sigma A5441 | 1:10,000 (NC) in 5% milk |
| phospho P38MAPK | Rabbit | CST 4631 | 1:1000 (NC) in 5% BSA |
| phospho JNK | Rabbit | CST 9251 | 1:1000 (NC) in 5% BSA |
| Total p38 | Rabbit | CST 9212 | 1:1000 (NC) in 5% BSA |
| Total JNK | Rabbit | CST 9225 | 1:1000 (NC) in 5% BSA |
| NOXA | Mouse | Millipore OP180 clone | 1:500 (NC) in 5% milk |
| BAK | Rabbit | Ab32371 | 1:1000 (NC) in 5% BSA |
| pIRE1a | Rabbit | Novus NB100 2323 | 1:1000 (NC) in 5% BSA |
| GADD34 | Rabbit | Protein Tech | 1:1000 (NC) in 5% BSA |

For all in vivo studies, the materials and methods outlined below were used.

All work in mice was approved by IACUC Board of Presage Biosciences, Seattle, WA. All relevant procedures were performed under anesthesia and all efforts were made to minimize pain and suffering. None of the mice contributing to this study became ill or died prior to experimental endpoints and all mice receiving drug treatment as described below, underwent routine health monitoring and were humanely euthanized at the end of the experiments. Subcutaneous flank xenografts were generated using the following cell lines/mouse strains tabulated below (Table 3). 200 ul cell suspension in a 1:1 ratio with matrigel (Corning) was injected into the right flank using 1 ml syringes (BD 309659) and 27 G needles (BD 305109).

For all CIVO microinjection studies, the materials and methods outlined below were used.

Mice were enrolled into CIVO drug studies when the tumor volume reached approximately 1000 mm$^3$. Microinjection studies were performed using the CIVO device as previously described (Klinghoffer et al, Science Translational Medicine 2015) The device was configured with 6 injection needles set for a 6 mm injection length and a total volume delivery of A fluorescent tracking marker (FTM) was added to each drug reservoir in vehicle for delivery along with each drug or drug combination. All micro-doses were equivalent to or lower than what would be allowed under FDA guidelines for Exploratory IND (Investigational New Drug) studies and by solubility of drug into vehicle. Total amounts of agents injected are tabulated below in Table 4.

TABLE 4

| Drug | Amount | Source | Formulation |
| --- | --- | --- | --- |
| DLBCL CIVO Microinjections | | | |
| Voruciclib | 15.2 ug | Presage | 5% DMSO/water |
| Venetoclax (ABT-199) | 26 ng | Chemietek | 5% DMSO/water |
| Navitoclax (ABT-263) | 29.2 ng | Chemietek | 5% DMSO/water |
| TNBC CIVO microinjections | | | |
| Ixazomib (screen) | 15 ug | Selleck | 20% HPbCD |
| Doxorubicin (screen) | 5.1 ug | Pfizer | 0.9% saline |
| Carboplatin (screen) | 15 ug | Selleck | water |
| 5-FU (screen) | 2 ug | Selleck | 5% DMSO/water |
| Abraxane (screen) | 14.25 | Celgene | 0.9% saline |
| Olaparib (screen) | 13.05 ug | Selleck | 5% DMSO/water |
| Trametinib (screen) | 18.5 ug | Selleck | 5% DMSO/water |
| Everolimus (screen) | 7.2 ug | Selleck | 5% DMSO/water |
| BEZ 235 (screen) | 14.1 ug | Selleck | 5% DMSO/water |
| PU H71 (screen) | 15.4 ug | Selleck | water |
| Erlotinib (screen) | 2.95 ug | Selleck | 5% DMSO/water |
| Sunitinib (screen) | 3 ug | Selleck | 5% DMSO/water |
| Sorafenib (screen) | 13.95 ug | Selleck | 5% DMSO/water |
| Dasatinib (screen) | 14.6 ug | Selleck | 5% DMSO/water |
| Bortezomib (screen) | 1.2 ug | Chemietek | 5% DMSO/water |
| Dinaciclib (screen) | 11.88 ug | Selleck | 5% DMSO/water |
| Flavopiridol (screen) | 12.1 ug | Sigma | 5% DMSO/water |
| Palbociclib (screen) | 13.44 ug | Chemietek | 5% DMSO/water |
| Marizomib | 94 ng | Triphase | 5% DMSO/0.9% saline |

For all systemic drug efficacy studies, the materials and methods outlined below were used.

Mice were enrolled for study when tumors reached an average volume of 150-200 mm$^3$. Tumor volume was calculated as V=length×width×height, all three dimensions measured using digital calipers along with body weight. Animals were removed from the study when—any one of the three measured dimensions of the tumor exceeding 2 cm, volume exceeding 2500 mm$^3$, ulceration or body weight loss greater than 20%.

Tumor Growth Inhibition % (TGI) is defined as:

$$\frac{(V_{final}(\text{vehicle}) - V_{initial}(\text{vehicle})) - (V_{final}(\text{treatment}) - V_{initial}(\text{treatment}))}{(V_{final}(\text{vehicle}) - V_{initial}(\text{vehicle}))} \times 100$$

where measurements are averaged across tumors in respective arms. Wilcoxon Rank Sum or Mann-Whitney test was used as the statistical test to determine differences between treatment arms.

Drug doses, routes of administration, schedules and formulation protocols are detailed below. For oral gavage, Instech, Ref: FTP-20—38 feeding tubes and for IV, BD insulin syringes were used.

DLBCL Studies
  RIVA: Voruciclib 200 mpk (PO) 6 on/1 off and ABT 199 (PO) 1 mpk 2×/week for 4 weeks
  SUDHL4: Voruciclib 200 mpk (PO) 6 on/1 off and ABT 199 (PO) 25 mpk 6 on/1 off for 4 weeks
  U2932: Voruciclib 200 mpk (PO) 6 on/1 off and ABT 199 (PO) 10 mpk 2×/week for 4 weeks
AML Studies
  SKM1: Voruciclib 200 mpk (PO) 6 on/1 off+ABT 199 (PO) 10 mpk 6 on/1 off for 3 weeks
TNBC Studies
  HCC1187: Voruciclib 200 mpk (PO) 5 on/2 off+Ixazomib/MLN2238 (PO) 3 mpk Days 3, 6, 10, 13 for 2 weeks
  HCC1187: Palbociclib 120 mpk (PO) QD×14+Bortezomib 0.42 mpk (IV), Days 1, 4, 8, 11 for 2 weeks
  HCC1187: Voruciclib 200 mpk (PO)+Bortezomib 0.42 mpk (IV), Days 1, 4, 8 11 for 2 weeks Example 1. Voruciclib is a Potent Inhibitor of Cyclin-Dependent Kinase-9 (CDK9)

Voruciclib is thought to be a potent CDK4/6 inhibitor. The activity of voruciclib on 38 different kinases was tested in comparison to flavopiradol, a known CDK9 inhibitor. FIG. 1A depicts the structures of voruciclib and flavopiridol and FIG. 1B depicts a comparison of the inhibition profiles of voruciclib and flavopiradol. FIG. 1B demonstrates that, similar to flavopiradol, voruciclib is a potent inhibitor of CDK9 ($K_i$<10 nM). However, voruciclib is more specific for CDKs than flavopiradol. FIG. 1B shows that flavopiradol is a potent inhibitor of the serine/threonine protein kinases MAK and ICK, whereas voruciclib does not show potent inhibition of either MAK or ICK. MAK and ICK are associated with gut epithelial cells and may account for the severe diarrhea associated with flavopiradol treatment. Voruciclib, on the other hand, may exhibit fewer gastrointestinal side effects. DiscoveRx and ThermoFisher screens: Percent Inhibition of kinase activity for 468 kinase assays of the DiscoveRx ScanMax kinase panel and 414 kinase assays of the ThermoFisher SelectScreen kinase panel at 10 uM and 50 nM. Test Article is pre-weighted at Presage into silanized amber screw cap vials and shipped to DiscoveRx and Reaction Biology. For ThermoFisher, the compound is weighed in and dissolved at 10 mM DMSO prior to shipment at ambient conditions. On receipt, vials are stored at −20 C until used. Powder is dissolved in DMSO at 10 mM.

Figure 2:
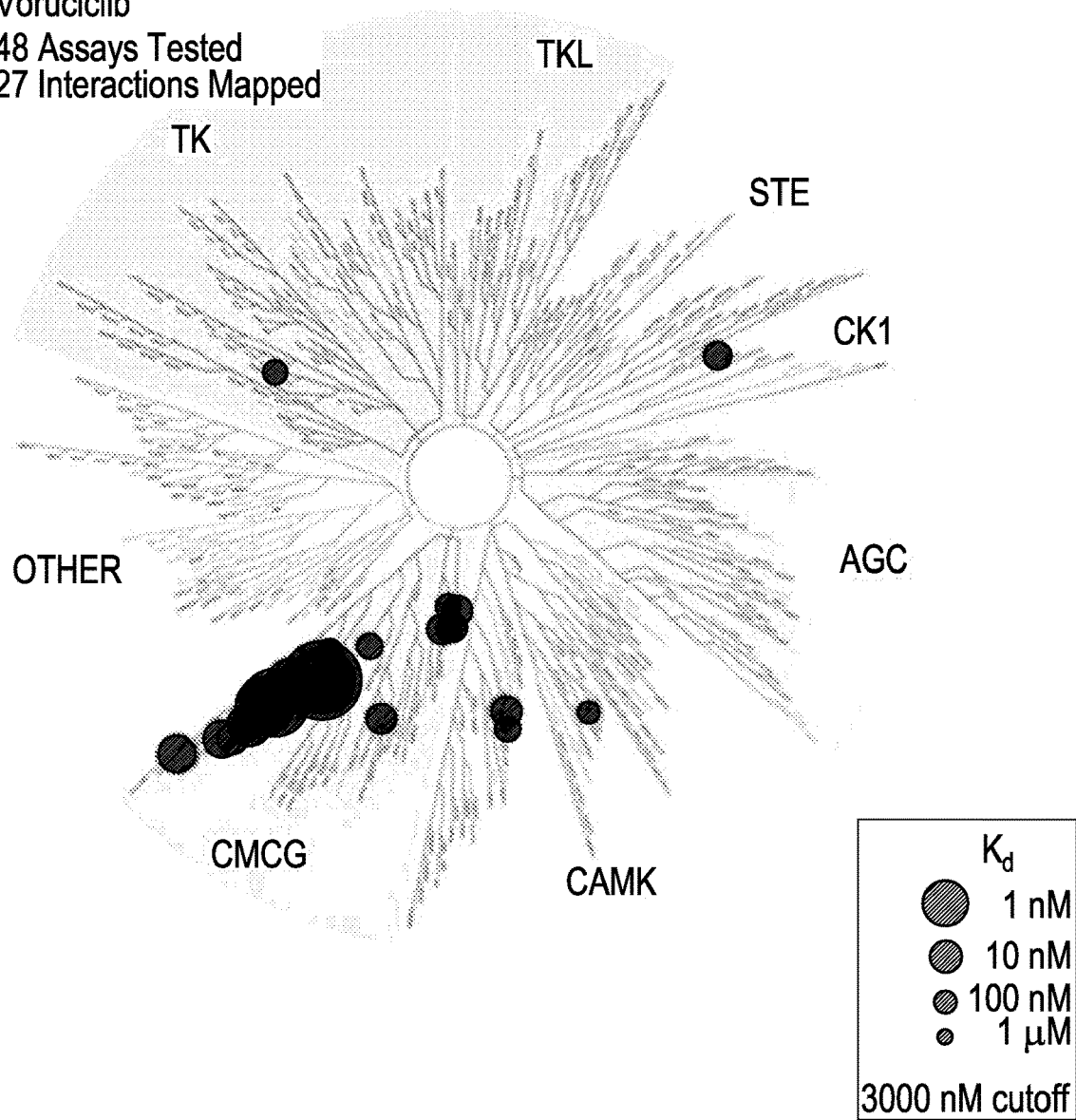
FIG. 2 illustrates single-digit nM potency of voruciclib against cyclin-dependent kinases.
Figures 6A, 6B:
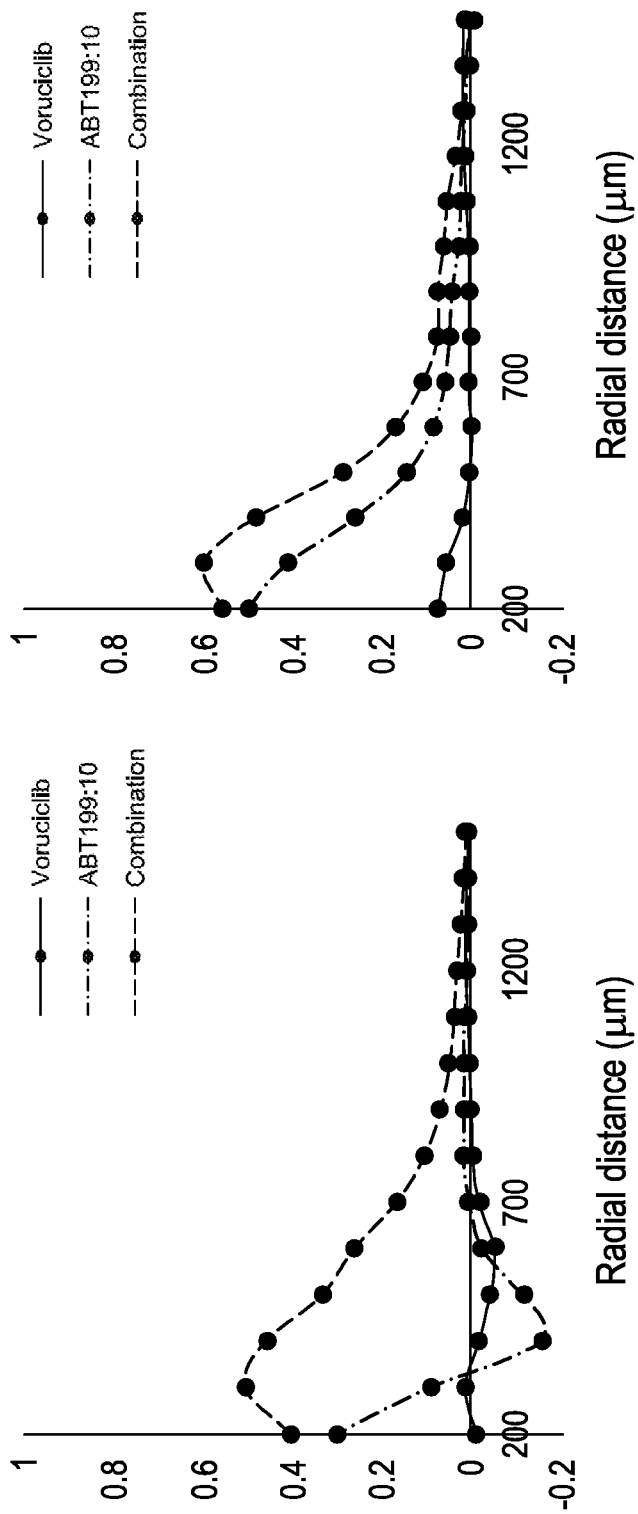
Figure 6E:
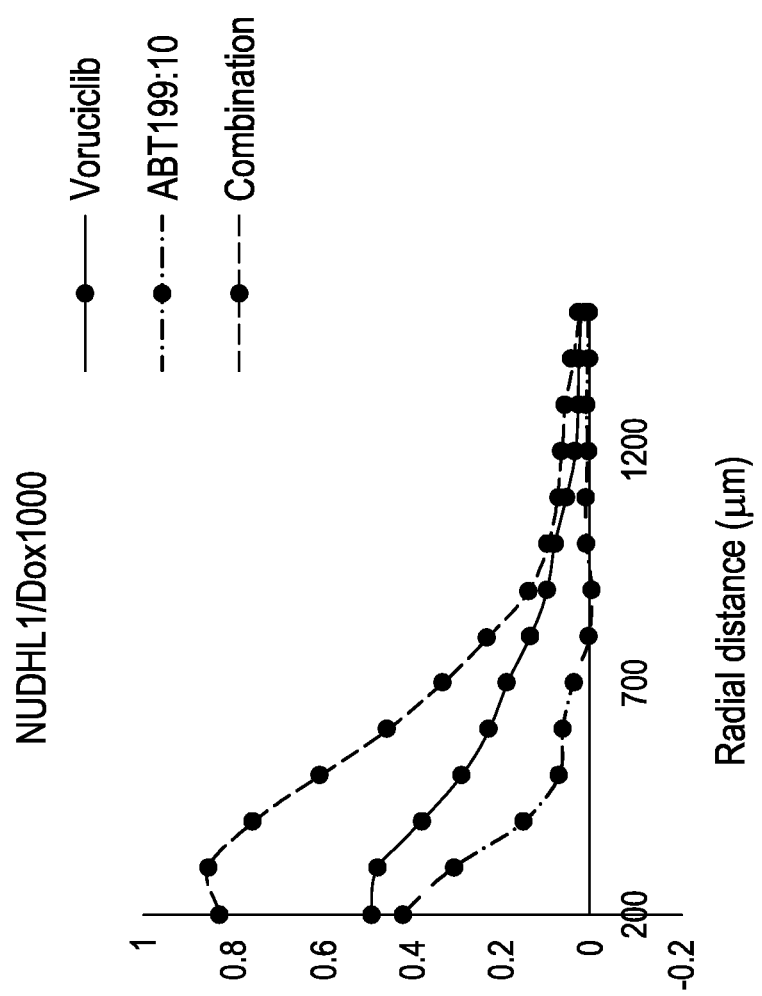

FIG. 2 shows single digit nM potency of voruciclib for CDKs 1, 4, 6, and 9 with strongest inhibition of CDK9. Reaction Biology profiling: Objective of the study was to determine the rank order of sensitivity of 48 kinases to voruciclib hydrochloride. The testing facility was Reaction Biology Corp. Kinase activity was measured using a filter binding assay with radioactive γ-33P-ATP as phosphate donor. The ATP concentration was near the Km for respective kinase. For each kinase, an IC50 value were calculated from a 10-point concentration curve of the test article and converted to Ki values. The 48 kinases studied here had been identified in previous screening experiments as the most promising target candidates.

Example 2. Voruciclib Exhibits a Synergistic Effect in Combination with the Bcl-2 Family Inhibitor, Venetoclax (ABT-199)

NU-DHL-1 diffuse large B-cell lymphoma (DLBCL) cells were treated with vehicle, voruciclib alone, venetoclax (ABT-199) alone, or a combination of voruciclib and venetoclax. FIGS. 3A-3D show NU-DHL-1 cells stained for the anti-apoptotic protein, induced myeloid leukemia cell differentiation protein Mcl-1 (MCL-1) (shown in red). FIG. 3A shows cells that were treated with vehicle only. In FIG. 3B, Voruciclib alone decreased the expression of MCL-1, shown by the increase in darker areas outlines in outline 301. Venetoclax alone increased the expression of MCL-1, as shown in the light colored areas within outline 302 of FIG. 3C. The combination of voruciclib and venetoclax led to a marked decrease in MCL-1 expression, shown in FIG. 3D, shown in the dark areas of outline 303.

FIGS. 4A-4D demonstrates a correlation between MCL-1 suppression with a synergistic induction of apoptosis. NU- DHL-1 diffuse large B-cell lymphoma (DLBCL) cells were treated with vehicle, voruciclib alone, venetoclax (ABT-199) alone, or a combination of voruciclib and venetoclax. The cells were stained for cleaved caspase-3 (CC3) (shown in red) as a marker of apoptosis. FIG. 4A shows cells that were treated with vehicle only. Voruciclib alone, shown in FIG. 4B, showed a slight increased the expression of CC3, as shown by the light colored areas within outline 401. Similarly, venetoclax alone, shown in FIG. 4C, showed a slight increased the expression of CC3, as shown by the light colored areas within outline 402. The combination of voruciclib and venetoclax in FIG. 4D showed synergistically increased expression of CC3, as shown in the large amount of light colored area within outline 403, suggesting an increased induction of apoptosis in the treated cells.

FIGS. 6A-6E demonstrate that the synergistic effect of voruciclib and venetoclax on apoptosis is reproducible across multiple DLBCL models. Briefly, RIVA, Toledo, Toledo/Dox1000, NUDHL, and NUDHL/Dox1000 cells were treated with voruciclib alone, venetoclax alone or voruciclib and venetoclax in combination, as shown in FIG. 6A, FIG. 6B, FIG. 6C, FIG. 6D, and FIG. 6E, respectively. Voruciclib alone and venetoclax alone had a slight effect on CC3 expression, however, the combination of voruciclib and venetoclax demonstrated a synergistic induction of CC3 expression across all five DLBCL models.

Figure 7:
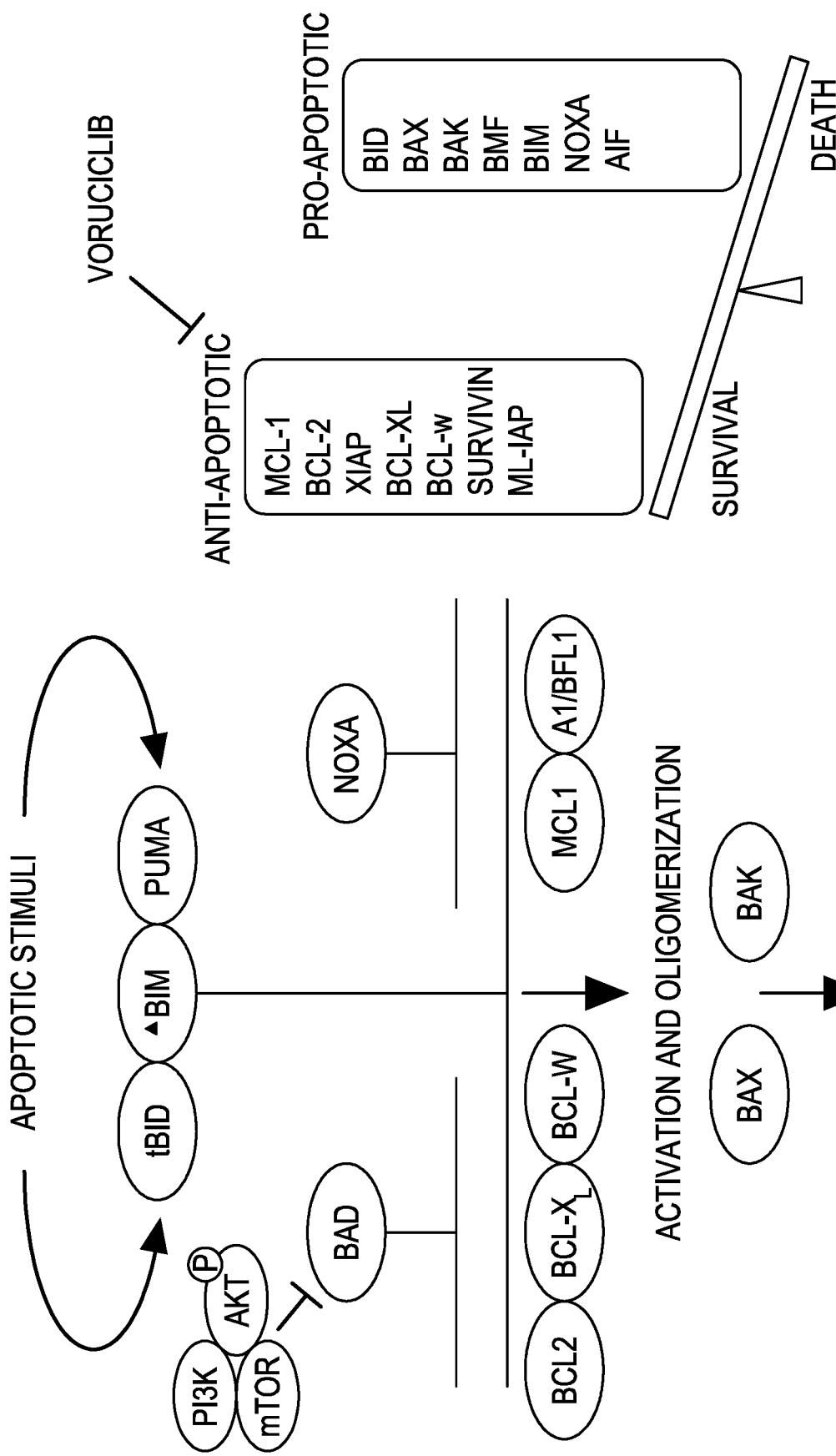
FIG. 7 illustrates that inhibition of MCL-1 through CDK9 helps shift cells to apoptosis.

FIG. 7 depicts a proposed model of this synergistic effect. Voruciclib, through inhibition of MCL-1 via CDK9, may shift cells to apoptosis when combined with Bcl-2 inhibition.

Example 3. Voruciclib Exhibits a Synergistic Effect in Combination with the Bcl-2 Family Inhibitor, Navitoclax Ramos Burkitt's lymphoma cells were treated with vehicle, voruciclib alone, navitoclax (ABT-263) alone, or a combination of voruciclib and navitoclax. FIGS. 5A-5D show Ramos Burkitt's lymphoma cells stained for cleaved caspase-3 (CC3) (shown in red) as a marker of apoptosis. FIG. 5A shows cells that were treated with vehicle only. Voruciclib alone, as shown in FIG. 5B, showed slight increase in the expression of CC3, as shown within the light areas of outline 501. Similarly, Venetoclax alone, as shown in FIG. 5C, showed slight increase in the expression of CC3, as shown within the light areas of outline 502. The combination of voruciclib and navitoclax showed a marked increase in the expression of CC3, as shown in the large amount of light colored area within outline 503 of FIG. 5D, suggesting an increased induction of apoptosis in the treated cells.

Figure 8C:
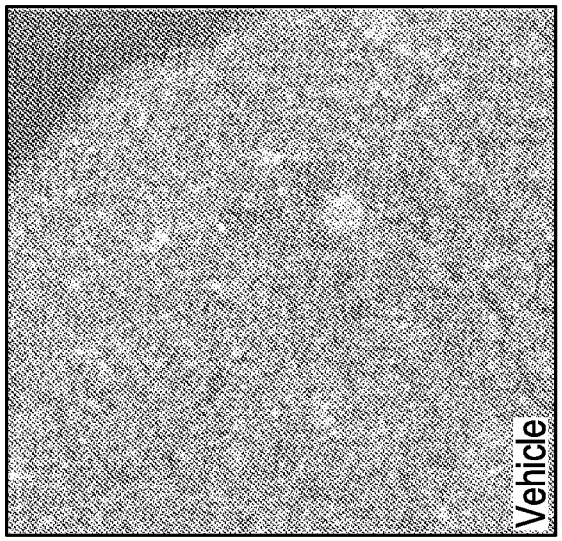
Figure 8D:
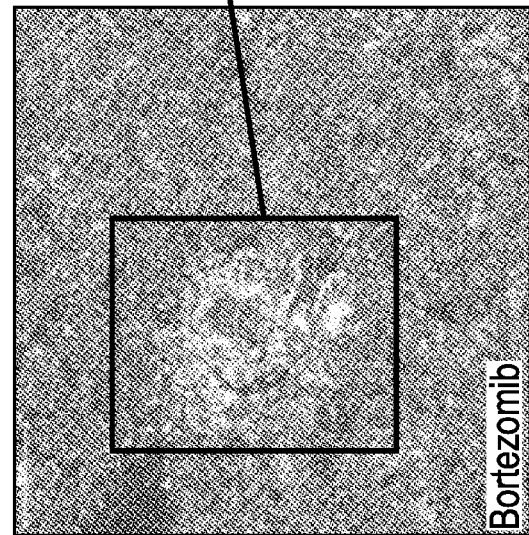
Figure 8B:
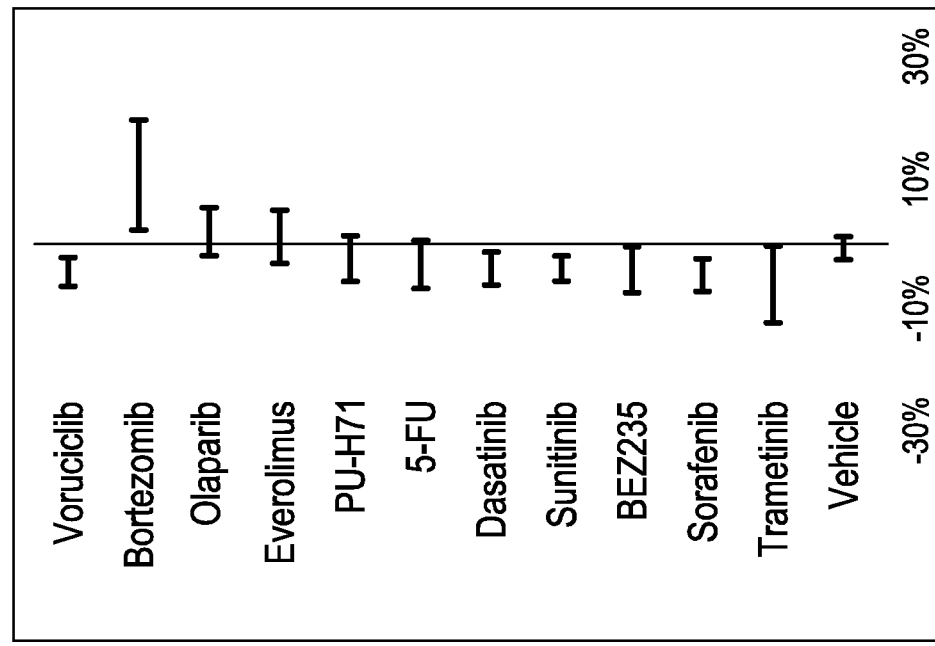

Example 4. Voruciclib Exhibits a Synergistic Effect in Combination with Proteasome Inhibitors A drug screen was performed to test multiple drugs simultaneously. FIG. 8A shows a list of various compounds that were injected into the HCC1187 triple negative breast cancer (TNBC) xenograft model. FIG. 8B shows the mean % change in MCL-1 induction in xenografts. The proteasome inhibitor, bortezomib showed an increase in the expression of MCL-1. FIG. 8C demonstrates xenografts that were treated with vehicle. FIG. 8D shows xenografts that were treated with bortezomib and stained for MCL-1 expression (shown in red). Bortezomib markedly increased the expression of MCL-1 in these cells, as shown by the increase of light colored areas within outline 801.

Example 5. Voruciclib Exhibits a Synergistic Effect in Combination with the Proteasome Inhibitor, Marizomib NudHL1 DLBCL xenografts were treated for 6 hours with vehicle, voruciclib alone, marizomib alone, or voruciclib and marizomib in combination. FIGS. 9A-9D depict cells that were treated as above and stained for cleaved caspase-3 (CC3) as a marker of apoptosis (shown in red). FIG. 9A shows cells that were treated with vehicle only. Cells treated with voruciclib alone, as shown in FIG. 9B, had little to no increase in CC3 expression, as shown by the small amount of light colored area within outline 901. Similarly, cells treated with marizomib alone, as shown in FIG. 9C, had little to no increase in CC3 expression, as shown by the small amount of light colored area within outline 902. Cells treated with combination voruciclib and marizomib showed a marked increase in CC3 expression, as shown by the large amount of light colored area within outline 903 of FIG. 9D, suggesting a synergistic effect on induction of apoptosis in these cells.

Example 6. Voruciclib Exhibits a Synergistic Effect in Combination with the Proteasome Inhibitor, Bortezomib Briefly, NudHL1 DLBCL xenografts were treated for 6 hours with vehicle, voruciclib alone, bortezomib alone, or voruciclib and bortezomib in combination. FIGS. 10A-10D depict cells that were treated as above and stained for cleaved caspase-3 (CC3) as a marker of apoptosis (shown in red).

Figures 10A, 10B, 10C, 10D:
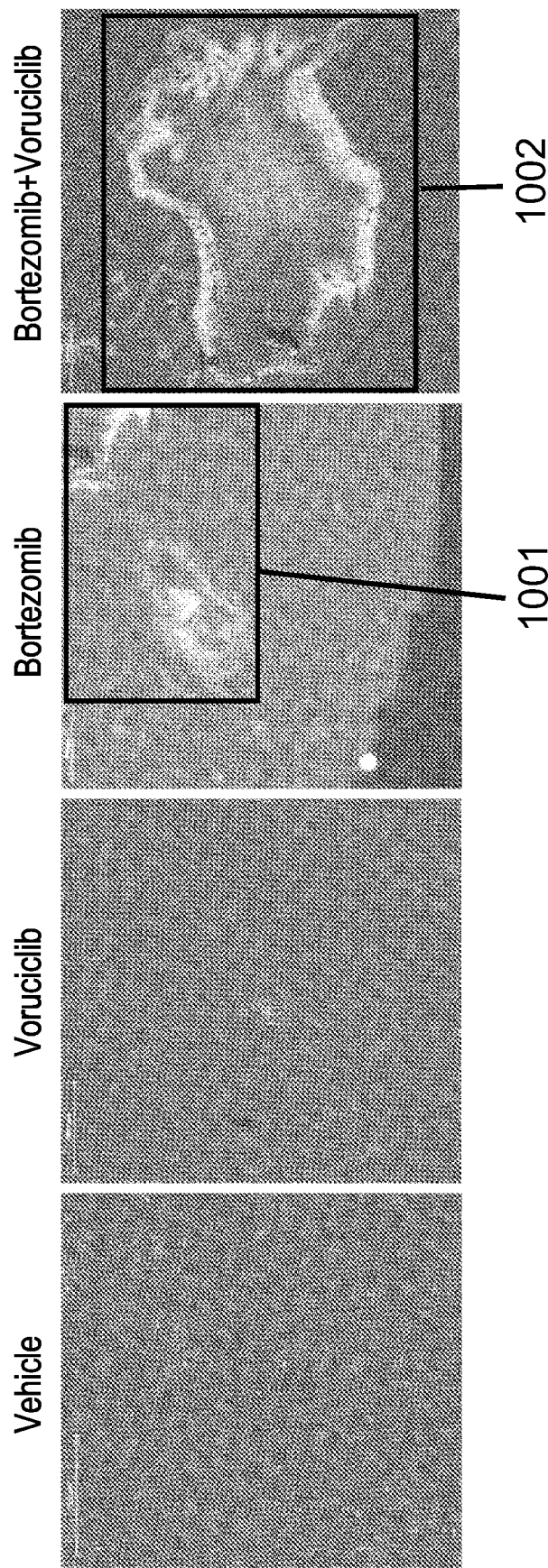
FIGS. 10A-10D illustrate a synergistic effect of voruciclib in combination with bortezomib on NudHL1 DLBCL cells. Cleaved caspase-3 (CC3)=red; DAPI=blue; fluorescent tracking marker (FTM)=green.

FIG. 10A shows cells that were treated with vehicle only. Cells treated with voruciclib alone, as shown in FIG. 10B, had little to no increase in CC3 expression. Similarly, cells treated with bortezomib alone, as shown in FIG. 10C, had little to no increase in CC3 expression, as shown by the small amount of light colored area within outline 1001. Cells treated with combination voruciclib and bortezomib showed a marked increase in CC3 expression, as shown by the large amount of light colored area within outline 1002 of FIG. 10D, suggesting a synergistic effect on induction of apoptosis in these cells.

Figures 11A, 11B, 11C, 11D:
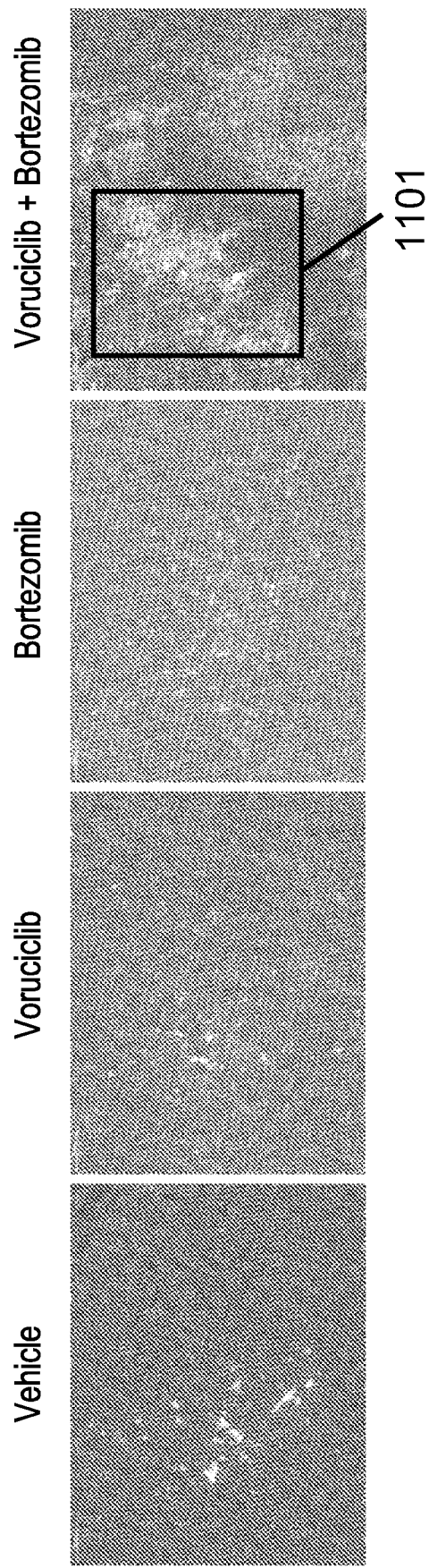
FIGS. 11A-11D illustrate a synergistic effect of voruciclib in combination with bortezomib on triple-negative breast cancer cells. Cleaved caspase-3 (CC3)=red; DAPI=blue; fluorescent tracking marker (FTM)=green.

FIG. 11 depicts a similar experiment performed on the HCC1187 triple negative breast cancer (TNBC) xenograft model. Briefly, cells were treated with vehicle, voruciclib alone, bortezomib alone, or voruciclib and bortezomib in combination. Cells were then stained for CC3 expression (shown in red) as a marker of apoptosis. FIG. 11A shows cells that were treated with vehicle only. Cells treated with voruciclib alone, as shown in FIG. 11B, had little to no increase in CC3 expression. Similarly, cells treated with bortezomib alone, as shown in FIG. 11C, had little to no increase in CC3 expression. Cells treated with combination voruciclib and bortezomib showed a marked increase in CC3 expression, as shown by the large amount of light colored area within outline 1101 of FIG. 11D, suggesting a synergistic effect on induction of apoptosis in these cells.

Figure 12A:
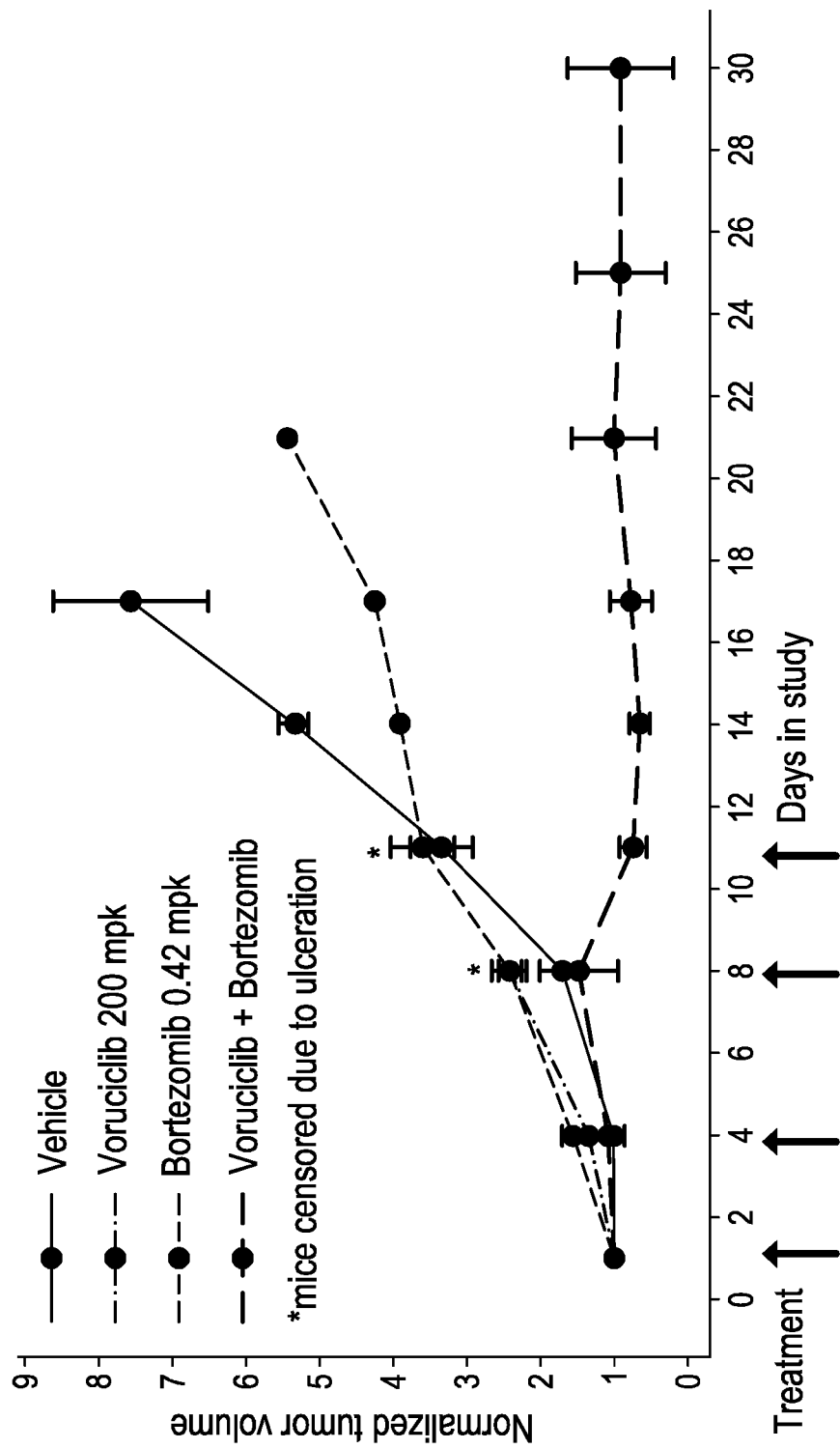

HCC1187 triple negative breast cancer (TNBC) xenograft mouse models were treated with vehicle, voruciclib (200 mg/kg), bortezomib (0.42 mg/kg), or voruciclib (200 mg/kg) and bortezomib (0.42 mg/kg) in combination. Tumor volume was measured in each mouse over time and the results are shown in FIGS. 12A-12D. Mice treated with a combination of voruciclib and bortezomib (FIG. 12D) showed a marked reduction in normalized tumor volume over time as compared to mice treated with voruciclib alone (FIG. 12B) or bortezomib alone (FIG. 12C). FIG. 12E shows a Western blot for MLC-1 protein expression. Cells treated with voruciclib reduced MCL-1 protein expression as compared to an untreated sample whereas cells treated with bortezomib increased MCL-1 protein expression as compared to the untreated sample. Further, voruciclib decreased the bortezomib-induced increase in MCL-1 expression.

Figure 13:
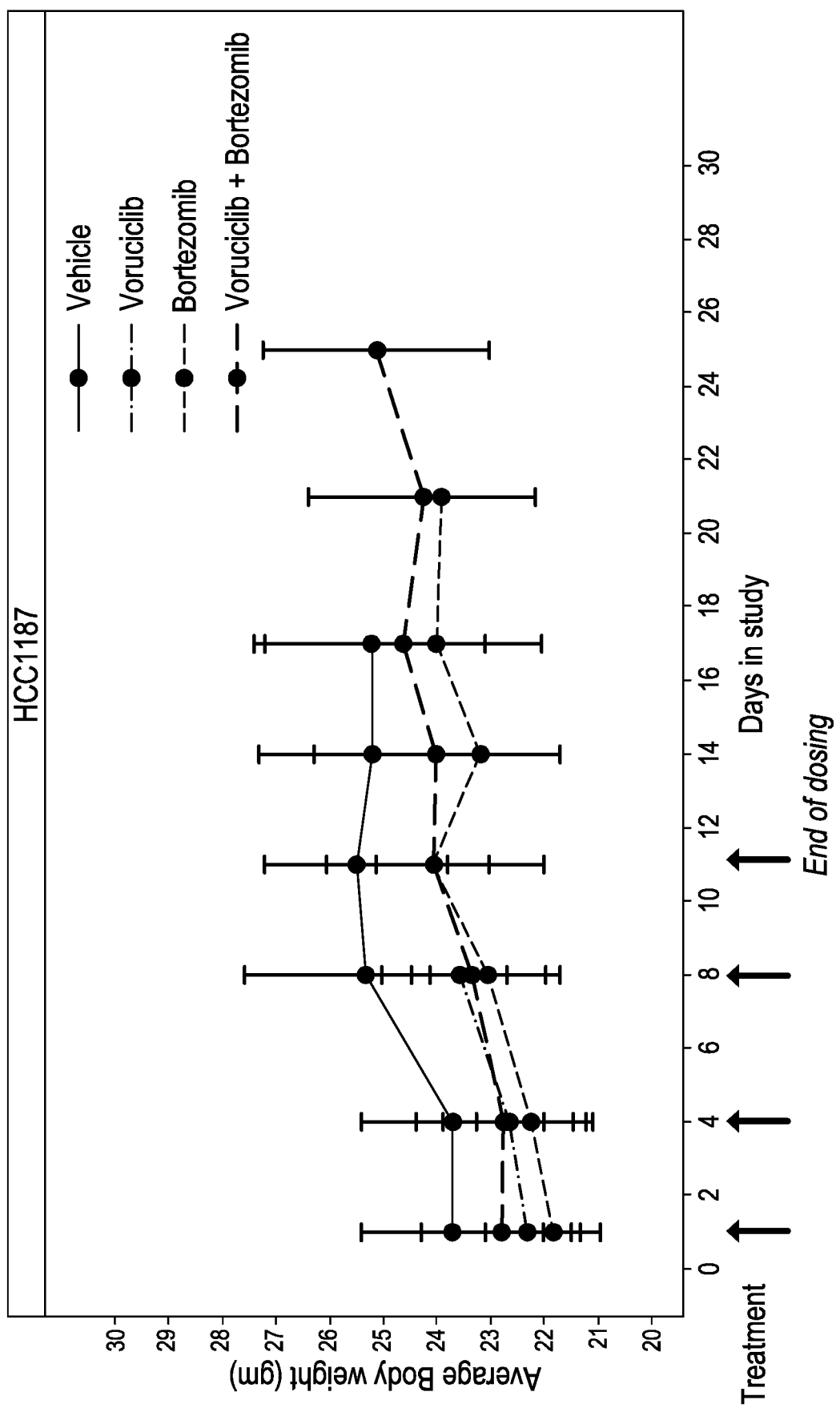
FIG. 13 illustrates that effect of voruciclid and bortezomib and the combination of voruciclib and bortezomib on body weight in an HCC1187 TNBC mouse model.

FIG. 13 demonstrates that body weight of mice was unaffected by treatment with voruciclib alone, bortezomib alone or voruciclib and bortezomib in combination. This data may suggest that combination therapy of voruciclib and bortezomib may exhibit little to no toxicity.

Figure 15A:
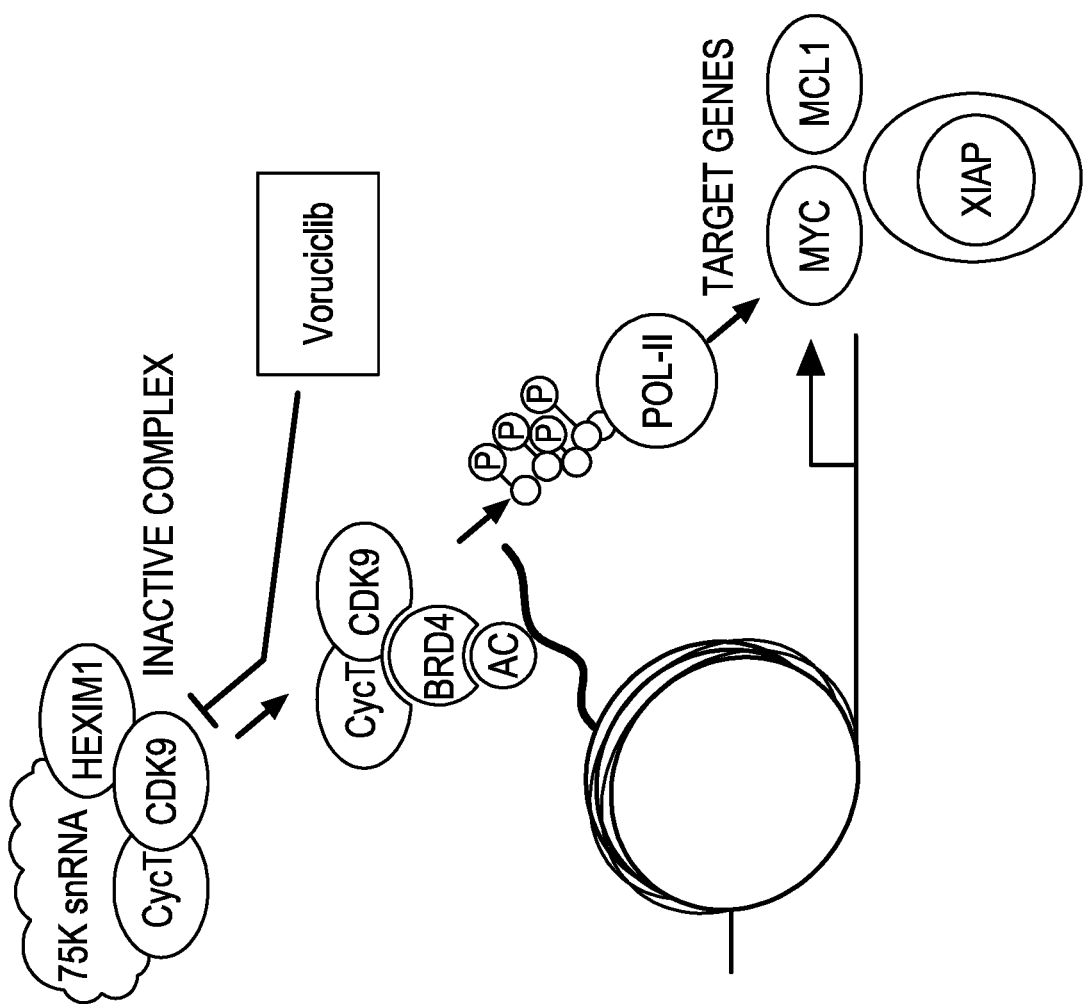
FIGS. 15A-15B illustrate that voruciclib diminishes bortezomib-induced MCL-1 and E3 ubiquitin-protein ligase XIAP expression.
Figure 15B:
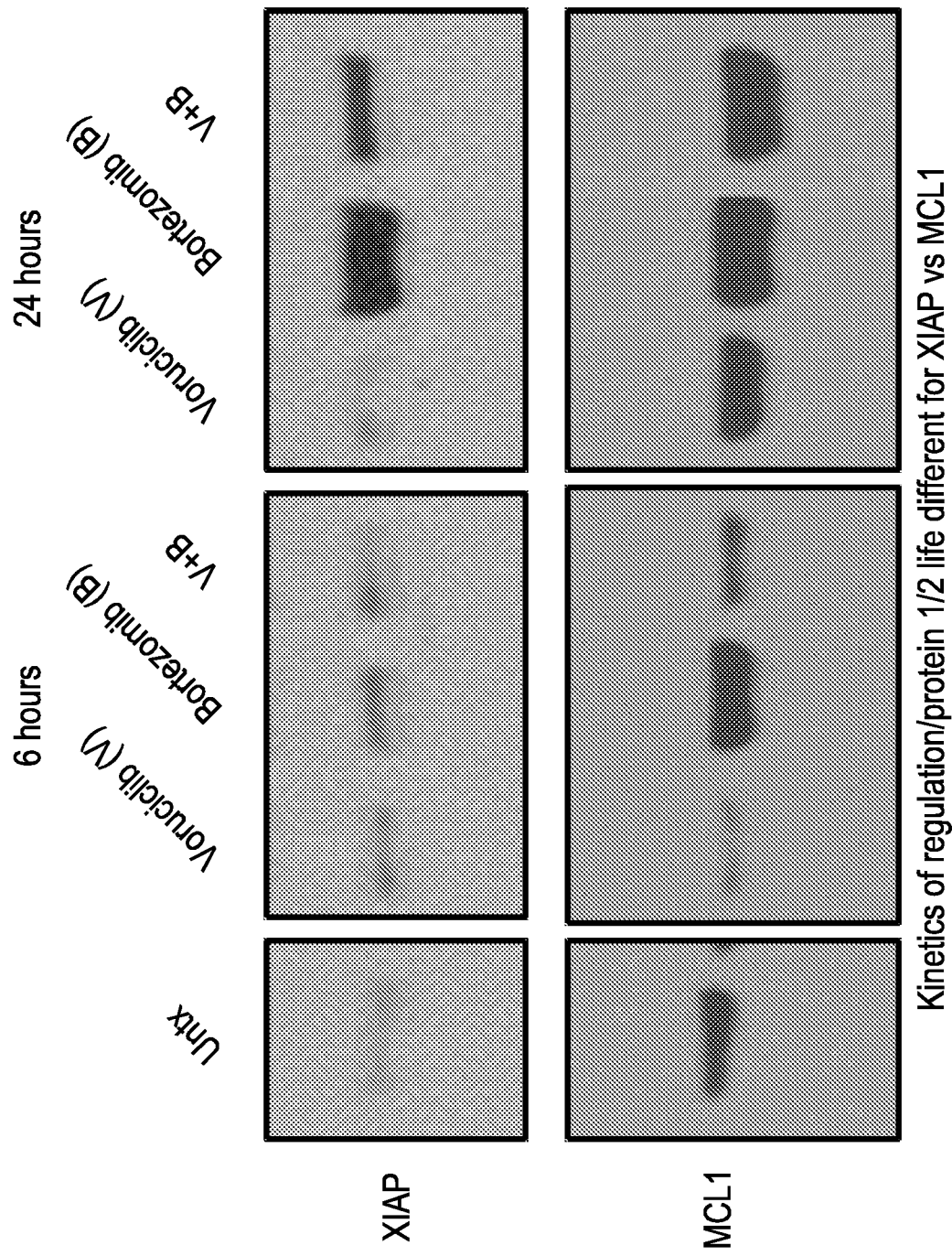

Further, voruciclib abrogates bortezomib-induced upregulation of pro-survival proteins, MCL-1 and E3 ubiquitin-protein ligase XIAP. FIG. 15A depicts a proposed model of voruciclib inhibition of CDK9. FIG. 15B shows MCL-1 and XIAP protein levels in cells treated with voruciclib alone, bortezomib alone, or voruciclib and bortezomib in combination. The Western blot demonstrates that voruciclib diminishes the bortezomib-induced upregulation of both MCL-1 and XIAP proteins in these cells.

Figure 14:
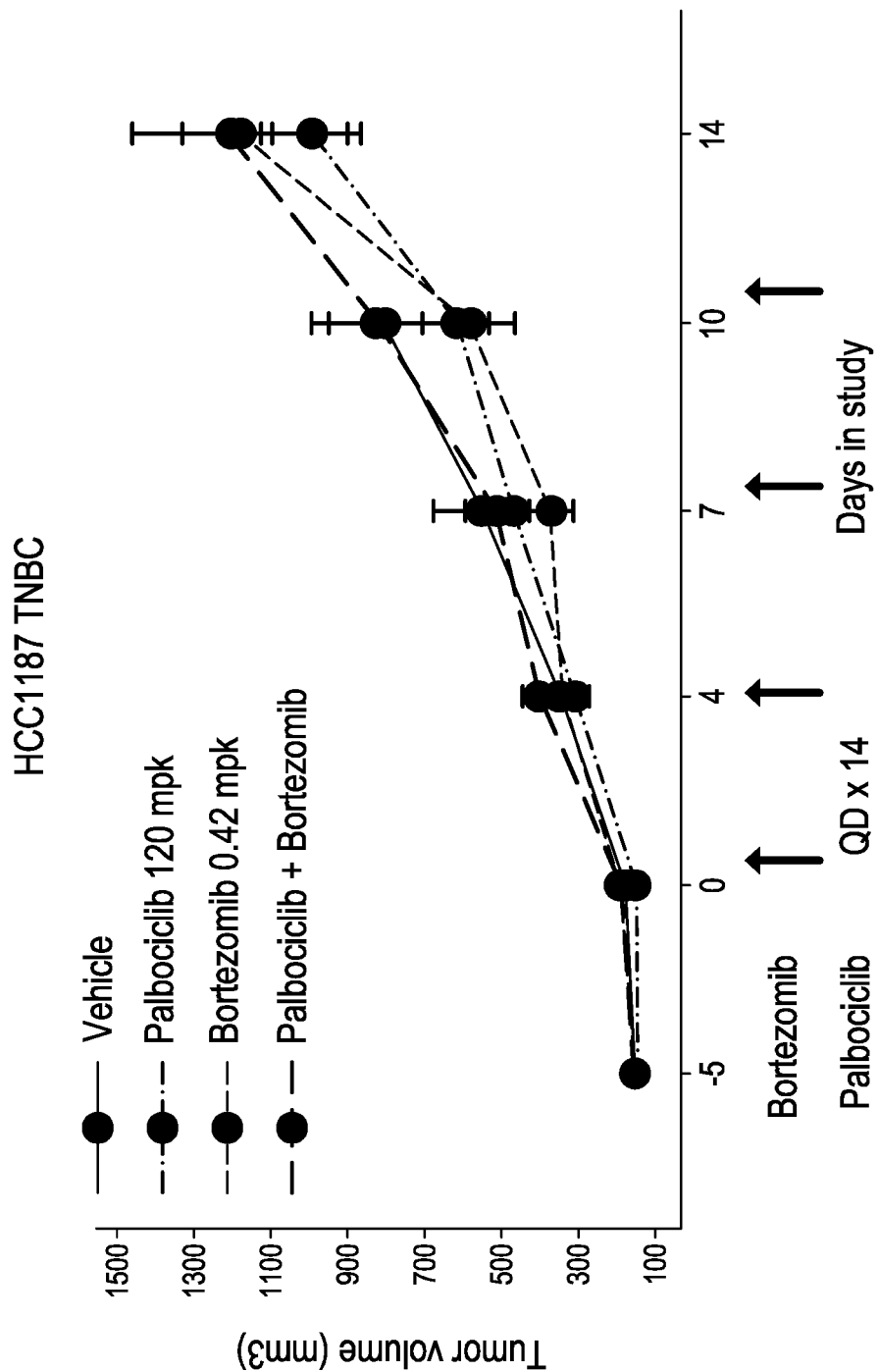
FIG. 14 illustrates the effect of bortezomib in combination with palbociclib, a CDK4/6 inhibitor, in an HCC1187 TNBC mouse model.

Example 7. Palbociclib, a CDK 4/6 Inhibitor, does not Exhibit a Synergistic Effect in Combination with Bortezomib HCC1187 triple negative breast cancer (TNBC) xenograft mouse models were treated with vehicle, palbociclib (120 mg/kg), bortezomib (0.42 mg/kg), or palbociclib (120 mg/kg) and bortezomib (0.42 mg/kg) in combination. Tumor volume was measured in each mouse over time and the results are shown in FIG. 14. Unlike voruciclib, palbociclib did not exhibit a synergistic effect on tumor volume in combination with bortezomib. Palbociclib is a specific CDK4/6 inhibitor whereas voruciclib targets CDK9. Thus, this difference may be CDK9-specific.

Figure 16B:
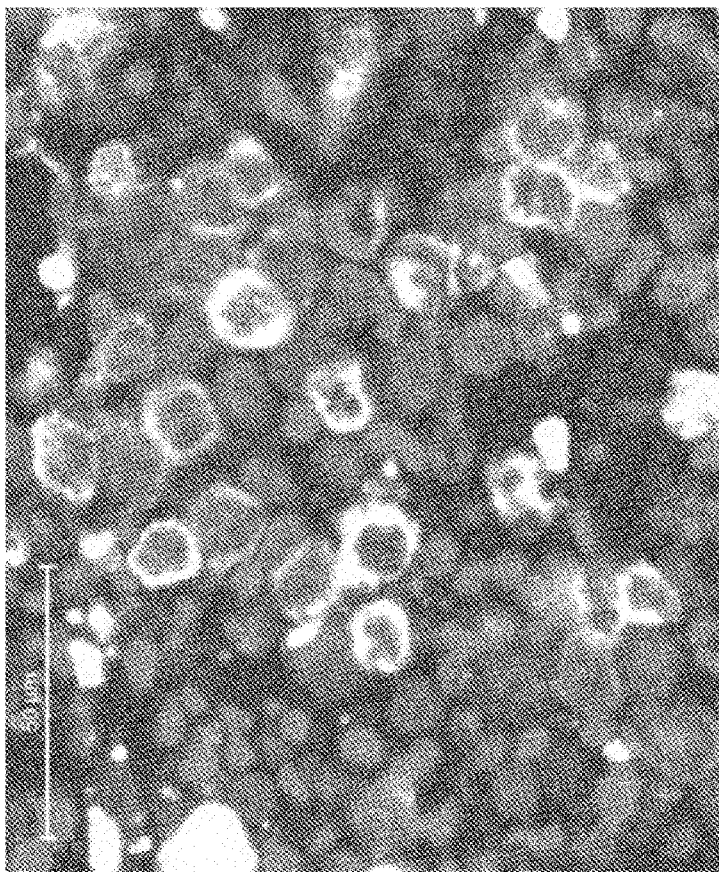
FIGS. 16A-16B illustrates cells resistant to bortezomib treatment.
Figure 16A:
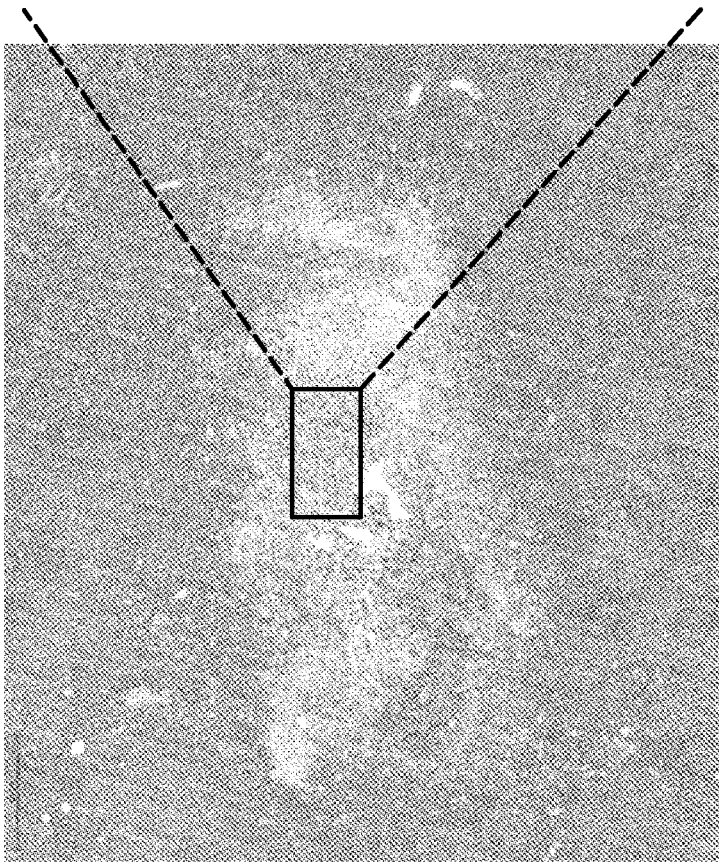
Figure 17:
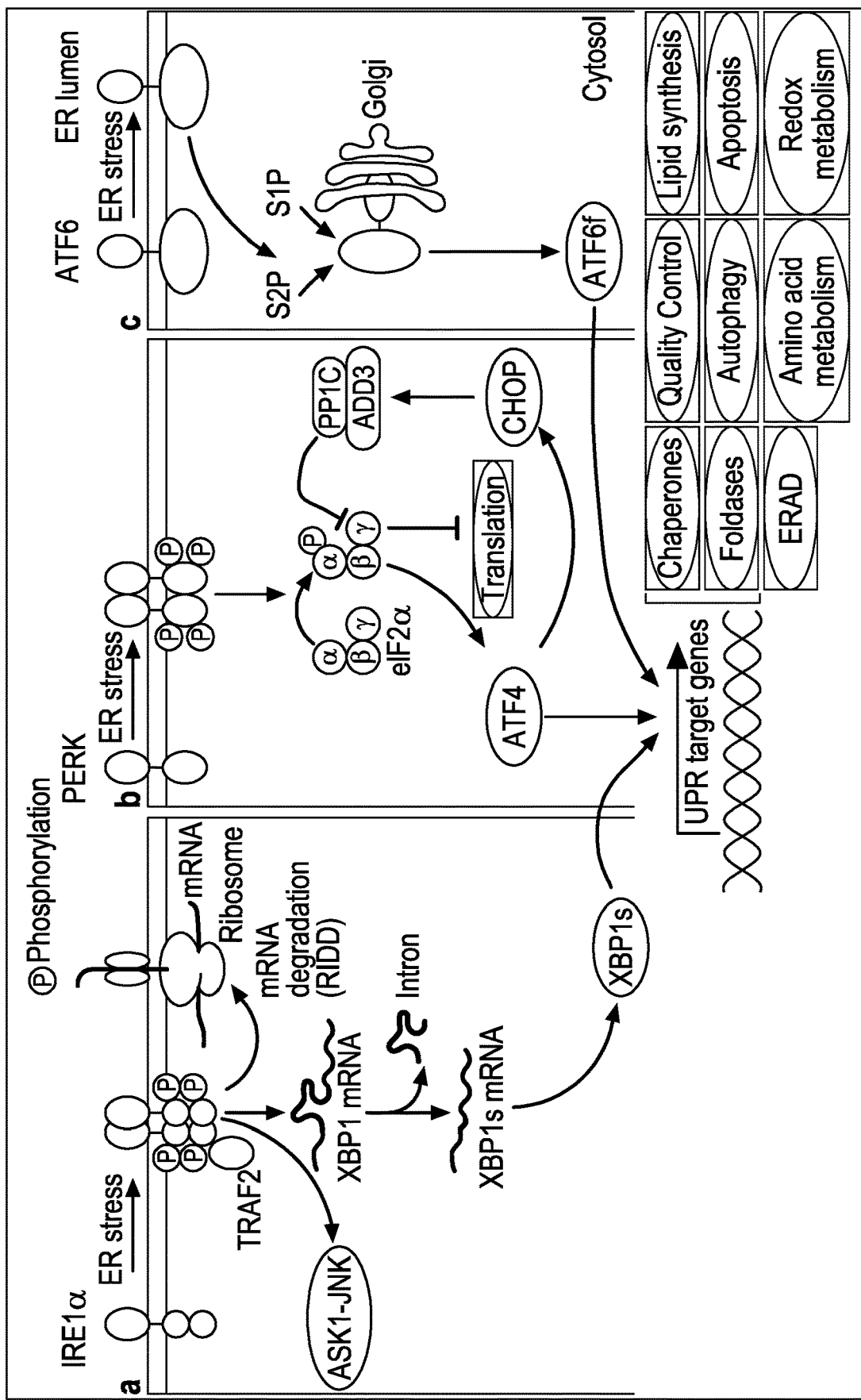
FIG. 17 illustrates three different ER stress response pathways.

Example 8. The Endoplasmic Reticulum (ER) Stress Response Pathway May Play a Role in the Synergistic Effects of Voruciclib in Combination with Bortezomib FIG. 16A shows a tissue section that was treated with bortezomib. Bortezomib induces apoptosis in some cells, while some cells appear to be resistant to bortezomib treatment. The cells were stained for the ER chaperone protein, GRP178/BiP. FIG. 16B demonstrates that the cells resistant to apoptosis by bortezomib express GRP178/BiP.

Figure 18A:
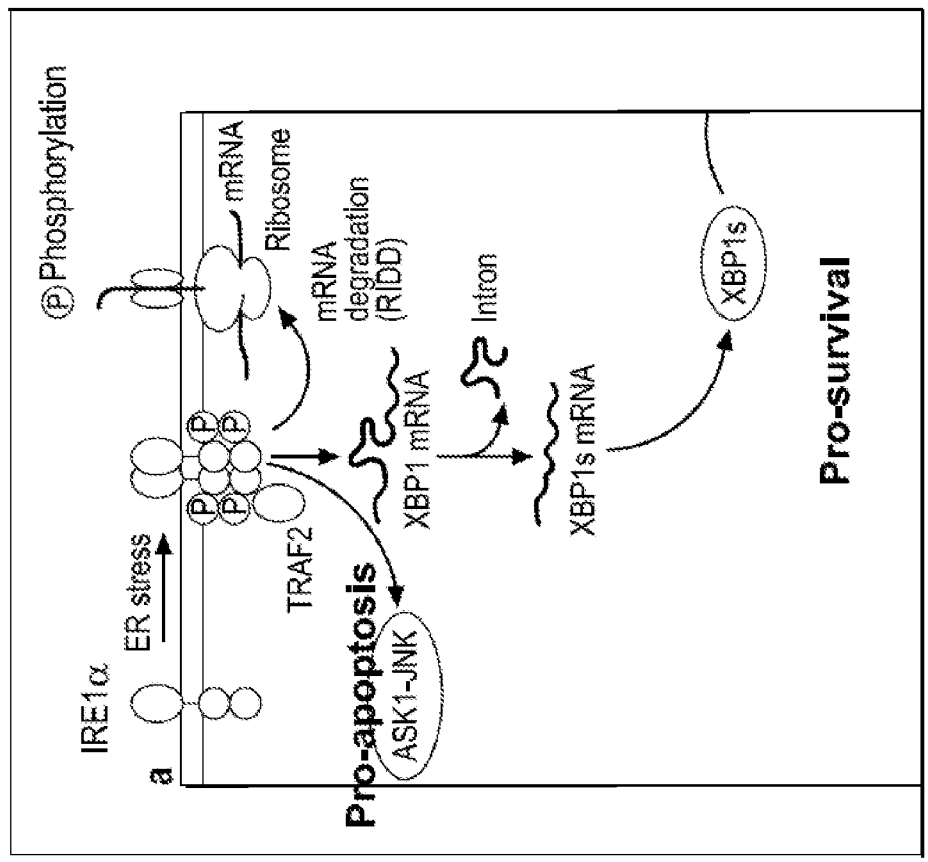
FIGS. 18A-18B illustrate that voruciclib may affect the IRE1α-dependent ER stress response pathway.
Figure 18B:
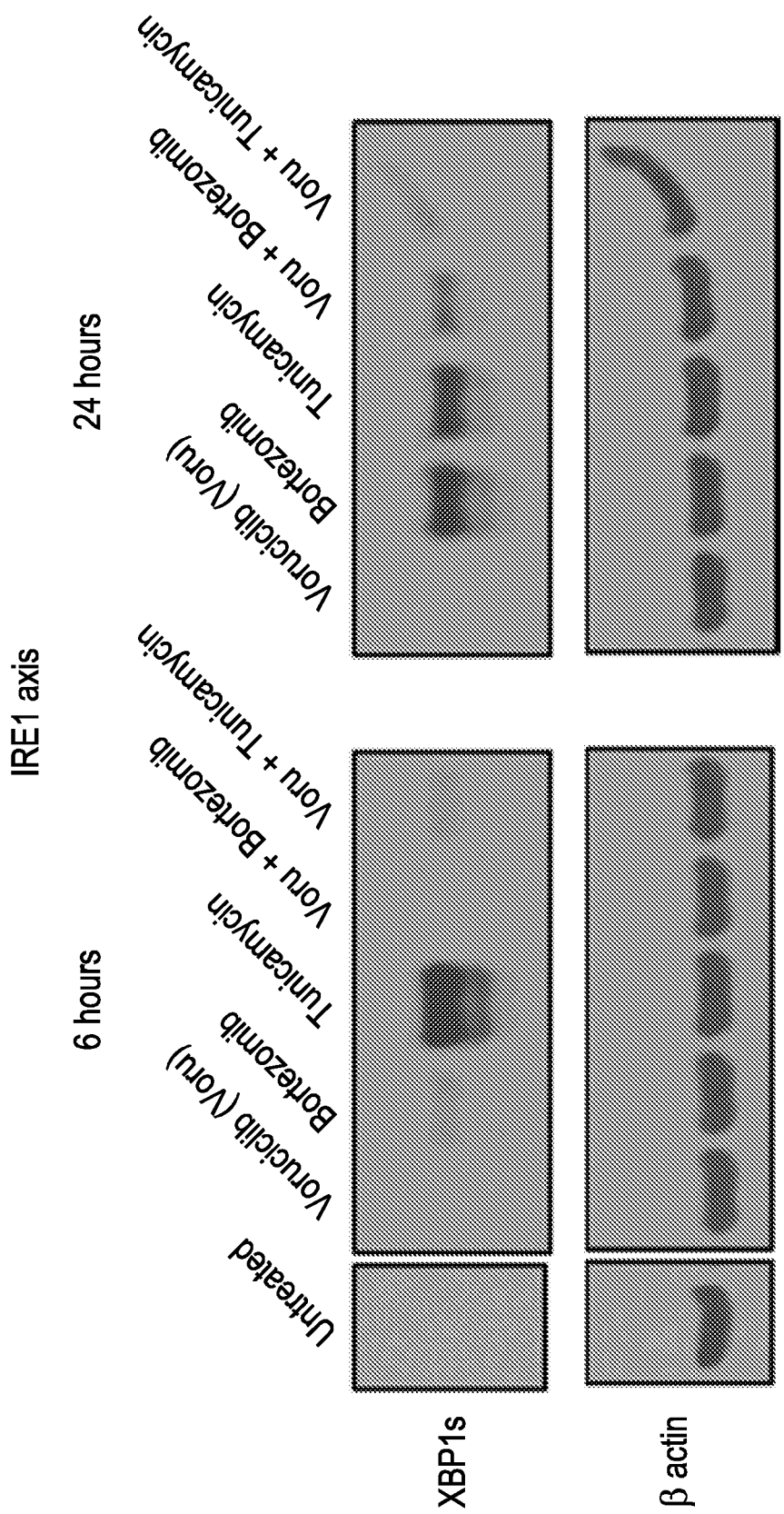
Figure 19A:
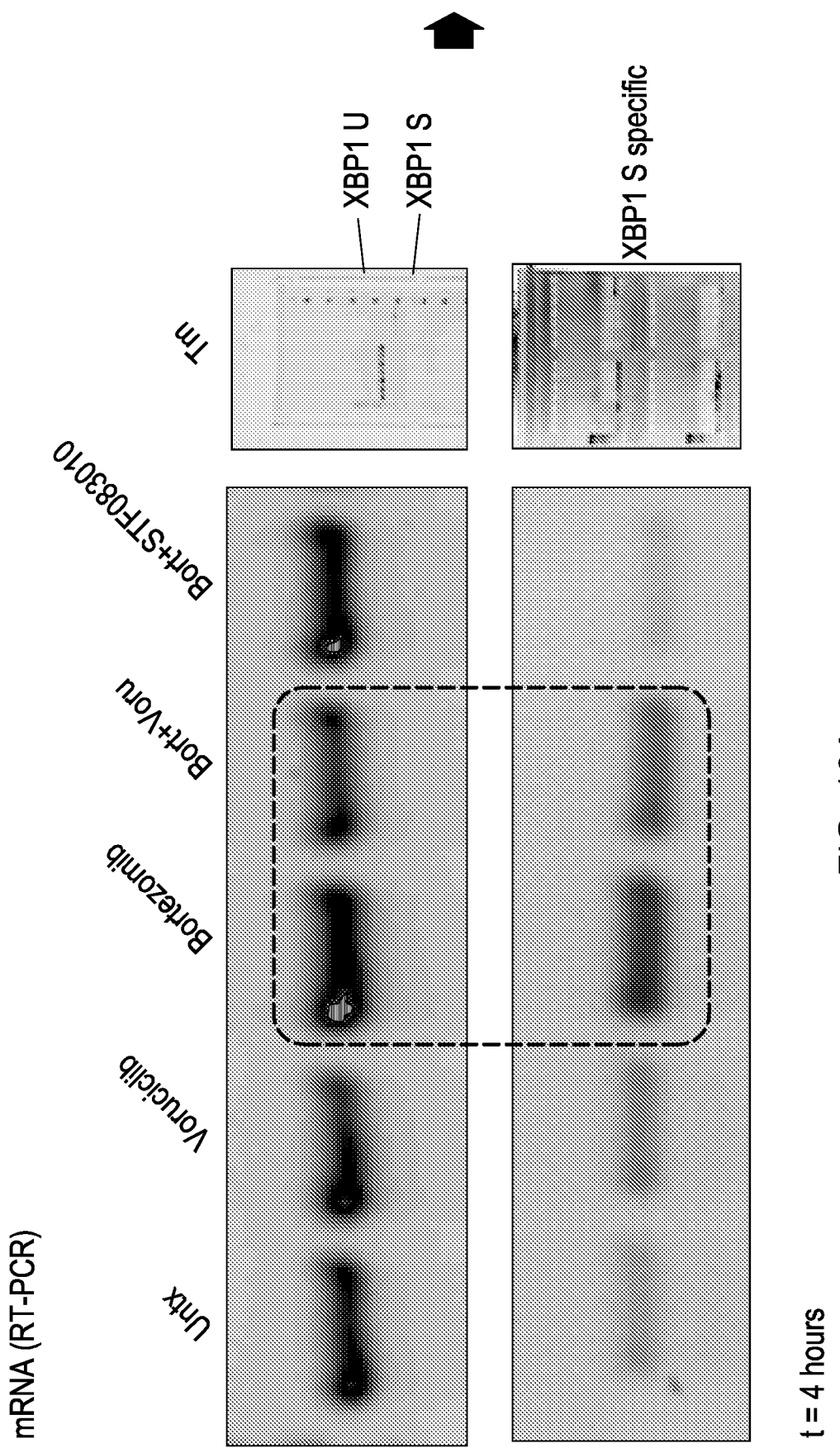
FIGS. 19A-19B illustrate repression of bortezomib-induced XBP1 transcription by voruciclib. STF083010=IRE1α endoribonuclease activity inhibitor; Tm=Tunicamycin
Figure 19B:
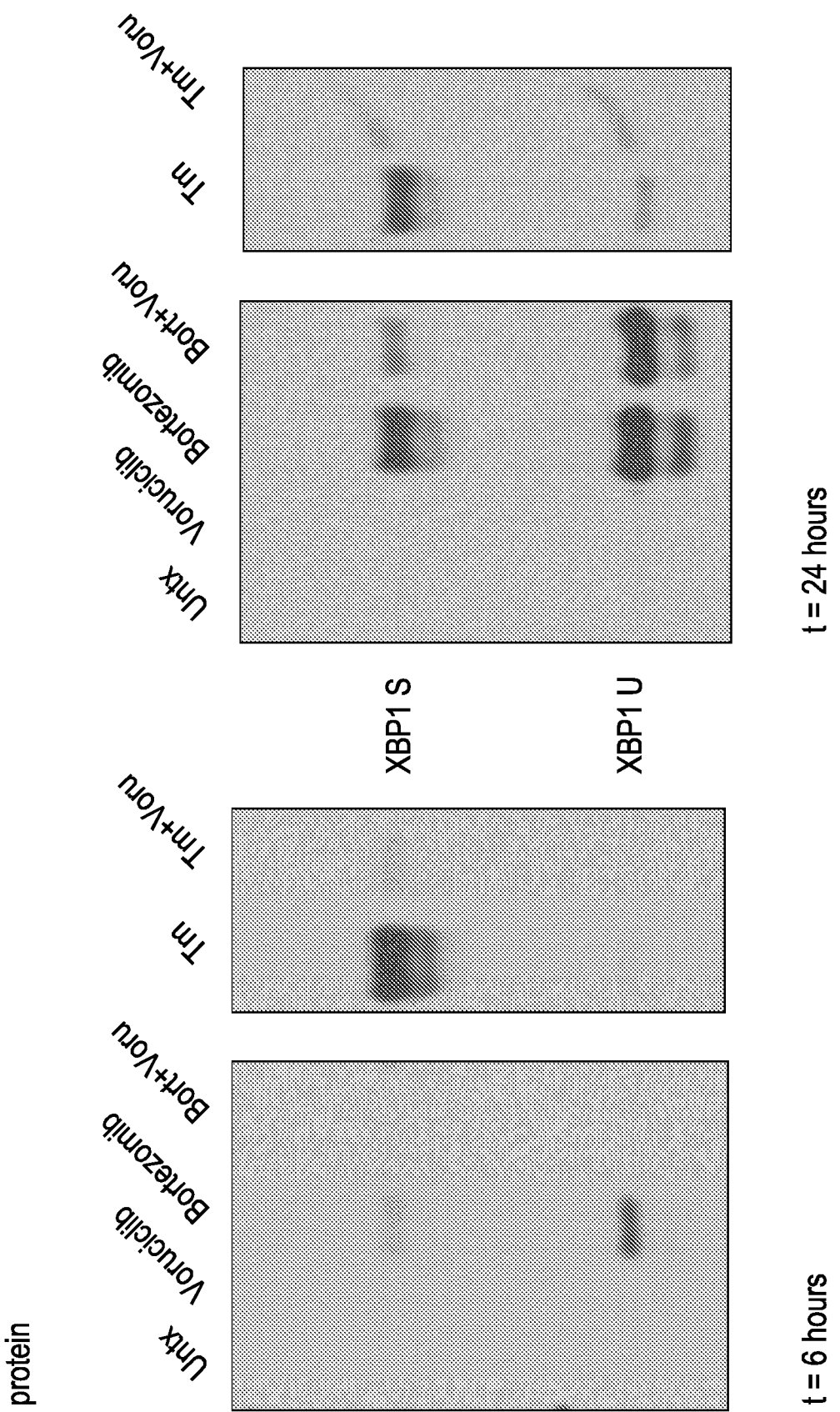

Next, HCC1187 triple negative breast cancer cells were treated with voruciclib alone, bortezomib alone, tunicamycin alone (an ER stress inducer), or in combination. Tunicamycin alone strongly induced X-box binding protein 1 (XBP1), an ER stress protein of the IRE1a arm of the ER stress pathway, at 6 hours. Further, tunicamycin and bortezomib strongly induced XBP1 expression at 24 hours (FIG. 18B). Combination of voruciclib with either bortezomib or tunicamycin diminished XBP1 upregulation. These results suggest that voruciclib may inhibit the IRE1α arm of the ER stress pathway (FIG. 18B). Voruciclib also decreased bortezomib-induced transcriptional induction of XBP1 (FIGS. 19A-19B). HCC1187 cells were treated with Voruciclib (1.5 uM), Bortezomib (10 nM), STF083010 IRE1α endoribonuclease activity inhibitor (Millipore) (60 uM) or Tunicamycin (Sigma)(100 nM) for 4 hours. mRNA was harvested using Qiagen RNAeasy Kit, quantified using a Nanodrop spectrophotometer. 1 ug of mRNA from each condition was used to generate cDNA using the High Capacity cDNA Reverse Transcription Kit (Applied Biosystems) and manufacturer's protocol. 100 ng cDNA was used to conduct a PCR assay to amplify XBP1 u or splice forms (Thermofisher PCR Supermix)—94 deg C. for 2 mins, (94 deg C. for 15 secs, 55 deg C. for 30 secs, 72 deg C. for 1 min)×30 cycles, 72 deg C. for 7 mins, hold at 4 deg C. XBP1 spiced and unspliced variants were detected.

Example 9. Voruciclib Exhibits a Synergistic Effect in Combination with the Proteasome Inhibitor, Ixazomib FIGS. 20A-20D depicts the HCC1187 triple negative breast cancer (TNBC) xenograft model. Briefly, cells were treated with vehicle, voruciclib alone, ixazomib alone, or voruciclib and ixazomib in combination. Cells were then stained for CC3 expression (shown in red) as a marker of apoptosis.

FIG. 20A shows cells that were treated with vehicle only. Cells treated with voruciclib alone, as shown in FIG. 20B, had little to no increase in CC3 expression, as shown by the small amount of light colored area within outline 2001. Similarly, cells treated with ixazomib alone, as shown in FIG. 20C, had little to no increase in CC3 expression, as shown by the small amount of light colored area within outline 2002. Cells treated with combination voruciclib and ixazomib showed a marked increase in CC3 expression, as shown by the large amount of light colored area within outline 2003 of FIG. 20D, suggesting a synergistic effect on induction of apoptosis in these cells.

Figures 21A, 21B:
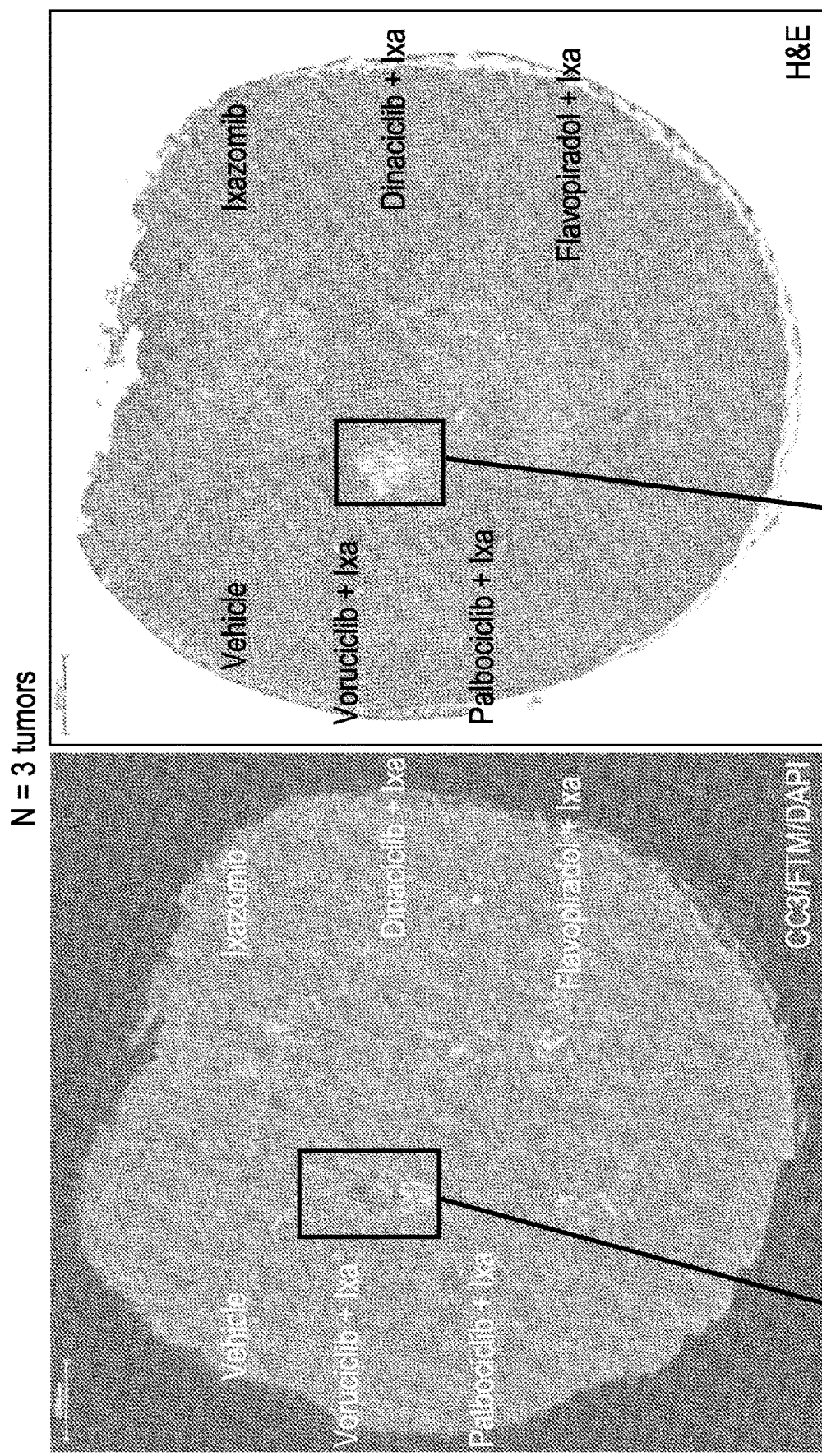
FIGS. 21A-21B illustrate a solid tumor section treated with CDK inhibitors, voruciclib, palbociclib, dinaciclib and flavopiradol in combination with ixazomib. Only Voruciclib+Ixazomib reproducibly lead to overt tumor cell clearing within 24 hr.

Various CDK inhibitors were tested in combination with ixazomib, as shown in FIGS. 21A and 21B. Only voruciclib demonstrated a synergistic effect on apoptosis of tumor cells in combination with ixazomib, as shown by the light colored areas within outlines 2101 and 2102. Vehicle only, ixazomib only, palbociclib and ixazomib, dinaciclib and ixazomib, and flavopiradol and ixazomib all did not exhibit the synergistic effect on apoptosis of tumor cells as the combination of voruciclib and ixazomib did.

Figures 22A, 22B:
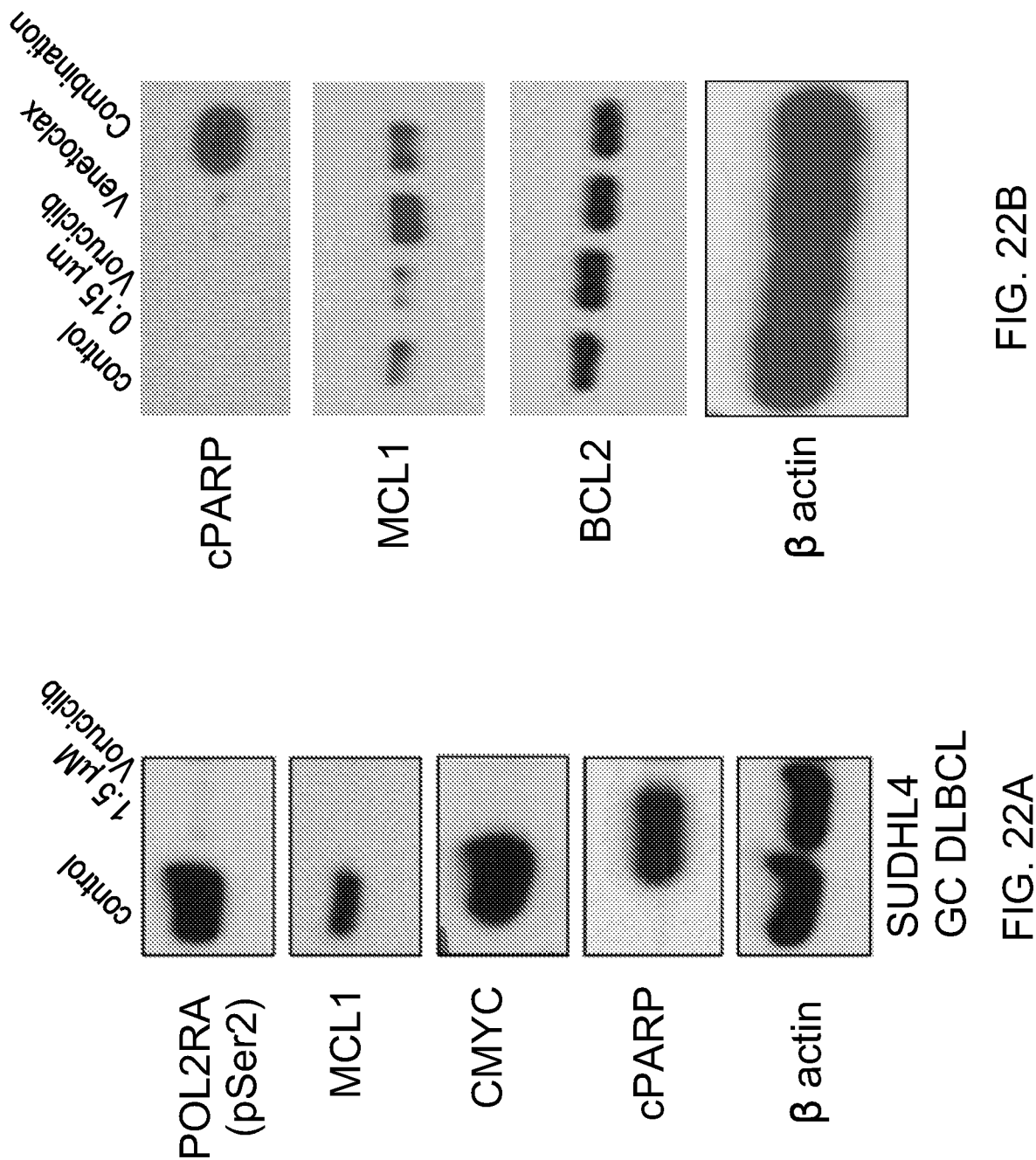
FIGS. 22A-B illustrates the synergy from voruciclib and venetoclax in the SU-DHL-4 model of diffuse large B-cell lymphoma (DLBCL).

Example 10. Voruciclib Exhibits a Synergistic Effect in Combination with the Venetoclax FIGS. 22A-B illustrate the synergy from voruciclib and venetoclax in the SU-DHL-4 model of DLBCL. Cleaved PARP (cPARP) may be used as a biomarker of apoptosis. To assess combination efficacy of the two agents of voruciclib and venetoclax together, low doses of each (150 nM voruciclib and 20 nM for venetoclax) were examined as single agents or as a combination in the SUDHL4 model of DLBCL. Cells were exposed to drug for 24 h prior to cell lysis and examination by Western Blot using antibodies specific for the cleaved form of PARP, MCL-1, C-MYC, and Beta actin (as a protein loading control) of FIG. 22A and BCL2 as an additional protein loading control in FIG. 22B. FIG. 22A illustrates that voruciclib suppresses MCL1 at 1.5 uM in DLBCL model.

FIG. 22B utilizes a 0.15 uM concentration of voruciclib, which is ⅒ that is shown to effectively induce apoptosis as a single agent. This level of voruciclib maintains some efficacy for repressing MCL-1 expression (compare lanes 1 & 2 of FIG. 22B) while cell exposure to venetoclax induces MCL-1 expression (compare lanes 1 & 3 of FIG. 22B). Low vorucicilib exposure also represses venetoclax-induced MCL-1 (compare lanes 3 & 4 of FIG. 22B).

FIGS. 23A-C illustrates the synergy from voruciclib and venetoclax in the SU-DHL-4 model, the OCI Ly10 model, and the U2932 model of DLBCL. Cleaved PARP (cPARP) may be used as a biomarker of apoptosis. To assess combination efficacy of the two agents of voruciclib and venetoclax, low doses of each were examined as single agents or as a combination in the three models of DLBCL. Cells were exposed to drug for 24 h prior to cell lysis and examination by Western Blot using antibodies specific for the cleaved form of PARP and Beta actin (as a protein loading control).

FIG. 23A illustrates that the combination of 0.15 uM voruciclib and 20 nM of venetoclax exhibits synergy to induce apoptosis in the SUDHL4 model of DLBCL that neither compound induces apoptosis as a single agent. FIG. 23B illustrates that the combination of 5 uM voruciclib and 50 nM of venetoclax exhibits synergy to induce apoptosis in the OCI Ly10 model of DLBCL where neither compound significantly induces apoptosis as a single agent. FIG. 23C illustrates that the combination of 5 uM voruciclib and 50 nM of venetoclax exhibits synergy to induce apoptosis in the U2932 model of DLBCL where the combination of the two compounds is clearly greater than just the addition of each compound as a single agent.

Figure 24:
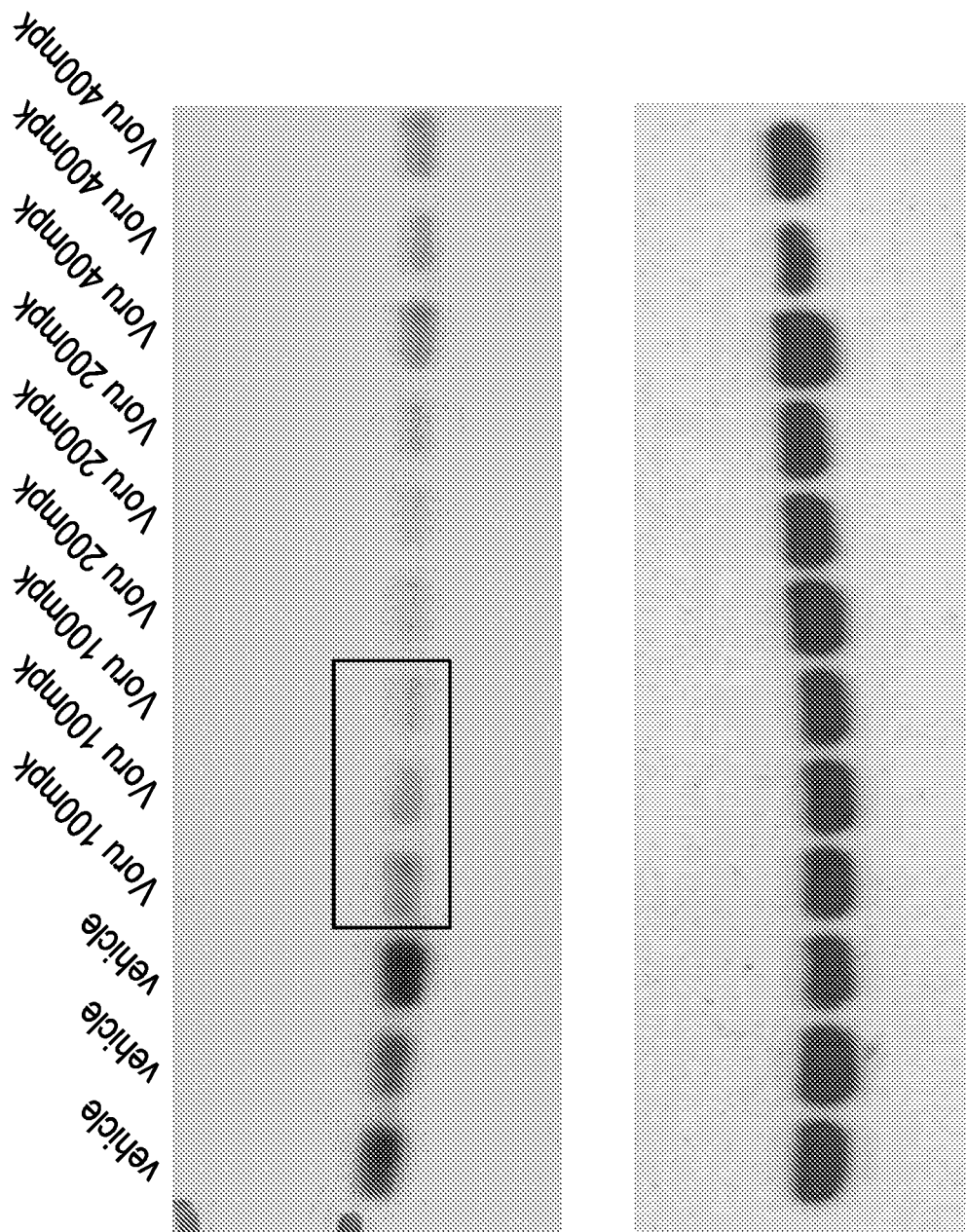
FIG. 24 illustrates that voruciclib suppresses MCL1 expression in DLBCL xenograft tumors.

Example 11. Voruciclib Suppresses MCL1 Expression in DLBCL Xenograft Tumors in Mice FIG. 24 illustrates that voruciclib suppresses MCL1 expression in DLBCL xenograft tumors in mice. Mice harboring DLBCL xenograft tumors (OCILY10) were dosed with voruciclib or vehicle control by oral gavage daily for 5 days and tumors were harvested for analysis of MCL-1 expression 4 h post the final dose. Tumor samples were cut in half, with one half solubilized in lysis buffer for western blot analysis and the other half fixed in formalin and prepared for immunohistochemistry. Western blots of tumor lysates from 3 individual mice per treatment group with antibodies specific for MCL-1 or Beta actin (protein loading control). The graph illustrates that voruciclib as a single agent suppressed MCL1 expression in DLBCL xenograft tumors at 100 mpk.

Figure 25A:
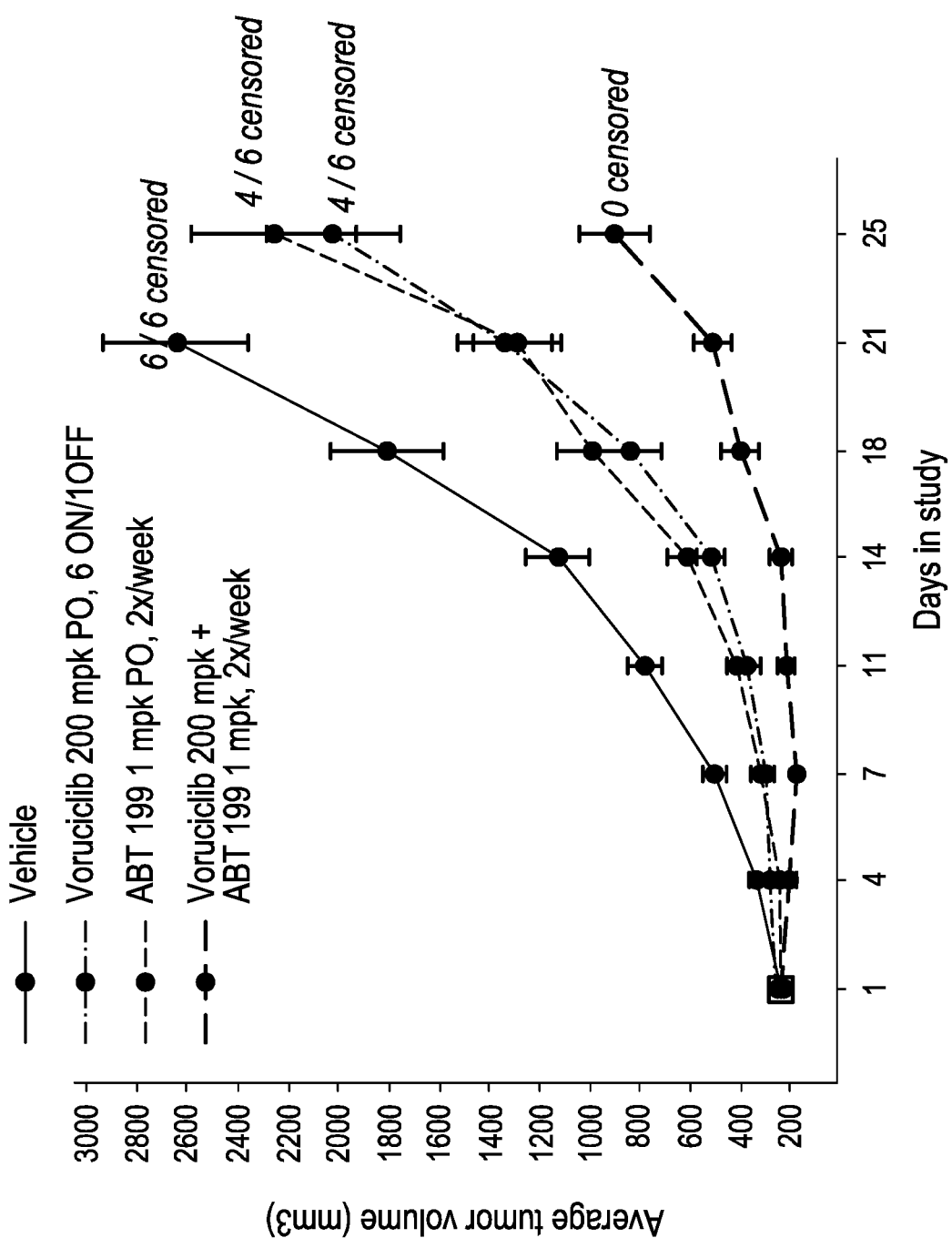
FIGS. 25A-25B illustrate the synergistic effect of voruciclib and venetoclax in ABC-type (RIVA) DLBCL in mice.
Figure 25B:
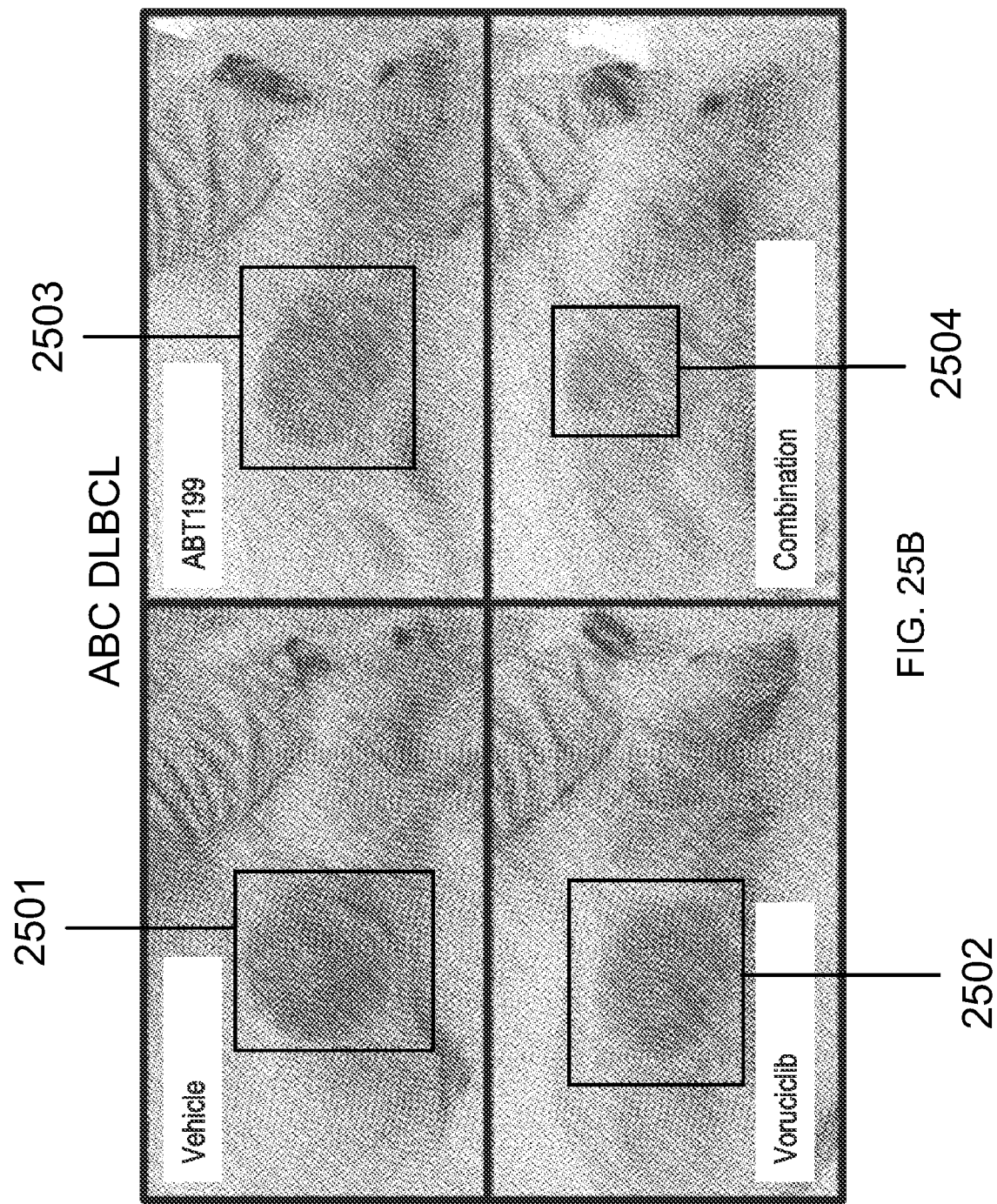

Example 12. Voruciclib and Venetoclax Impede Growth of DLBCL Xenograft Tumors in Mice FIGS. 25A-B illustrate the combination of voruciclib and venetoclax to impede growth of DLBCL xenograft tumors. Immune deficient NOD SCID mice were implanted with the RIVA (activated B-cell, or ABC) model of DLBCL. The xenografted tumors were allowed to grow in the NOD SCID host until they reached 200 mm$^3$, at which point the xenografted animals were randomized into 4 study groups: 1. Vehicle control; 2. Voruciclib at 200 mpk; 3. Venetoclax at 1 mpk; and 4. Combination of Voruciclib at 200 mpk and Venetoclax at 1 mpk. Voruciclib was dosed by oral gavage daily for 6 days of the week with a rest day in between cycles. Venetoclax was dosed by oral gavage on days 1 and 4 of each weekly cycle. Drug effects were assessed via tumor volume measurements twice weekly by a technician blinded to the treatment of each subject in the study. N=5-6 animals per treatment arm.

FIG. 25A graphs the average tumor volume (mm$^3$) for each of the 4 study groups: vehicle, single agent voruciclib, single agent venetoclax, and the combination of voruciclib and venetoclax. The single agent treatments saw a decrease in tumor volume over a longer period of study days. The combination treatment saw a much higher decrease in tumor volume size, more than 2-fold decrease of average tumor volume by 3 weeks into the study.

FIG. 25B illustrates images of the tumors of animals from each of the 4 study groups: vehicle, single agent voruciclib, single agent venetoclax, and the combination of voruciclib and venetoclax. The vehicle tumor size was the largest, as outlined by outline 2501. The tumor of single agent voruciclib is smaller, outlined by outline 2502. The tumor of single agent venetoclax is smaller than vehicle as well, outlined by outline 2503. The combination therapy tumor is outlined by outline 2504, which is significantly smaller than that of vehicle or either of the single agent therapies, suggesting a synergistic effect.

Figure 26A:
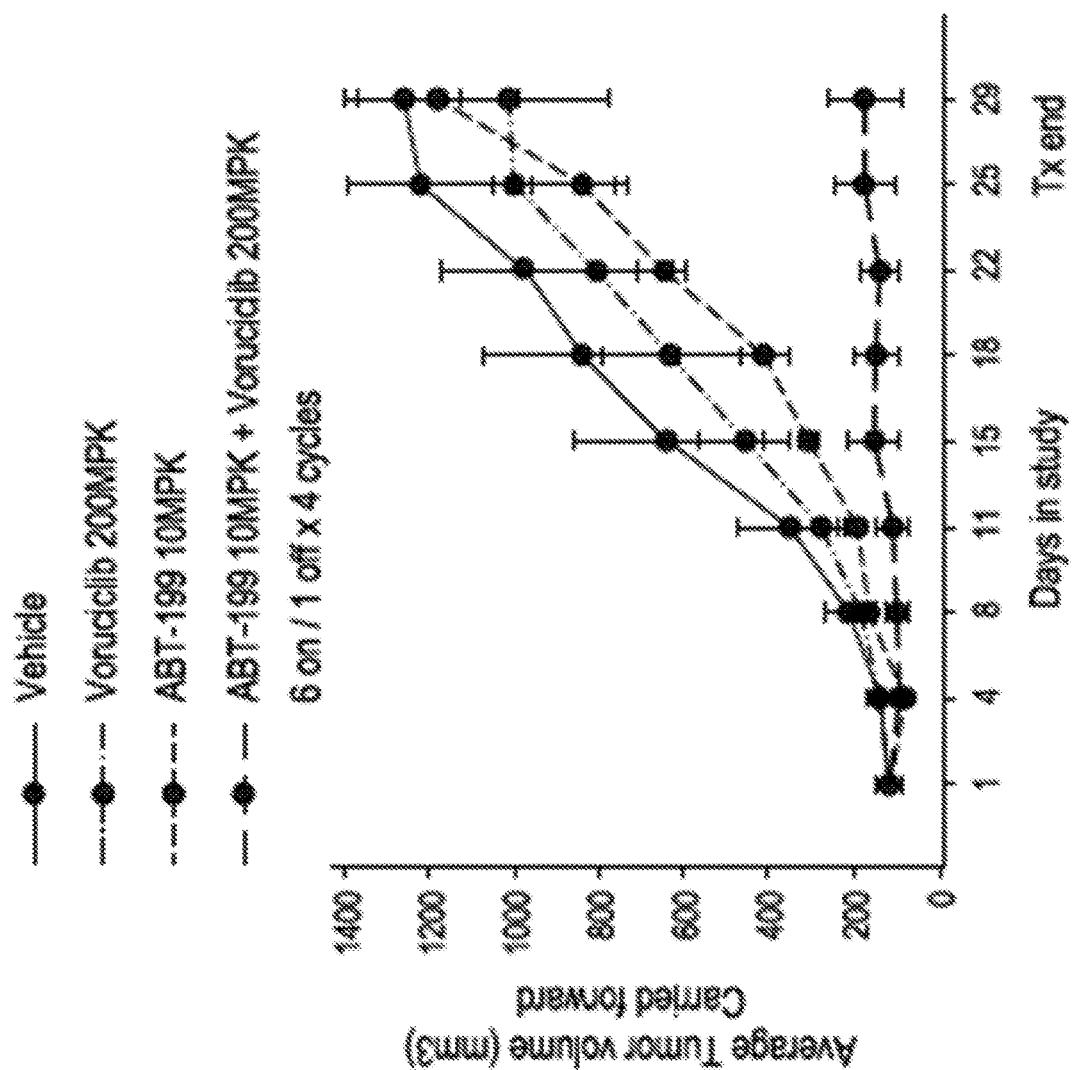
FIGS. 26A-26B illustrate the synergistic effect of voruciclib and venetoclax and the effect on body weight in U2932 model if DLBCL in mice.
Figure 26B:
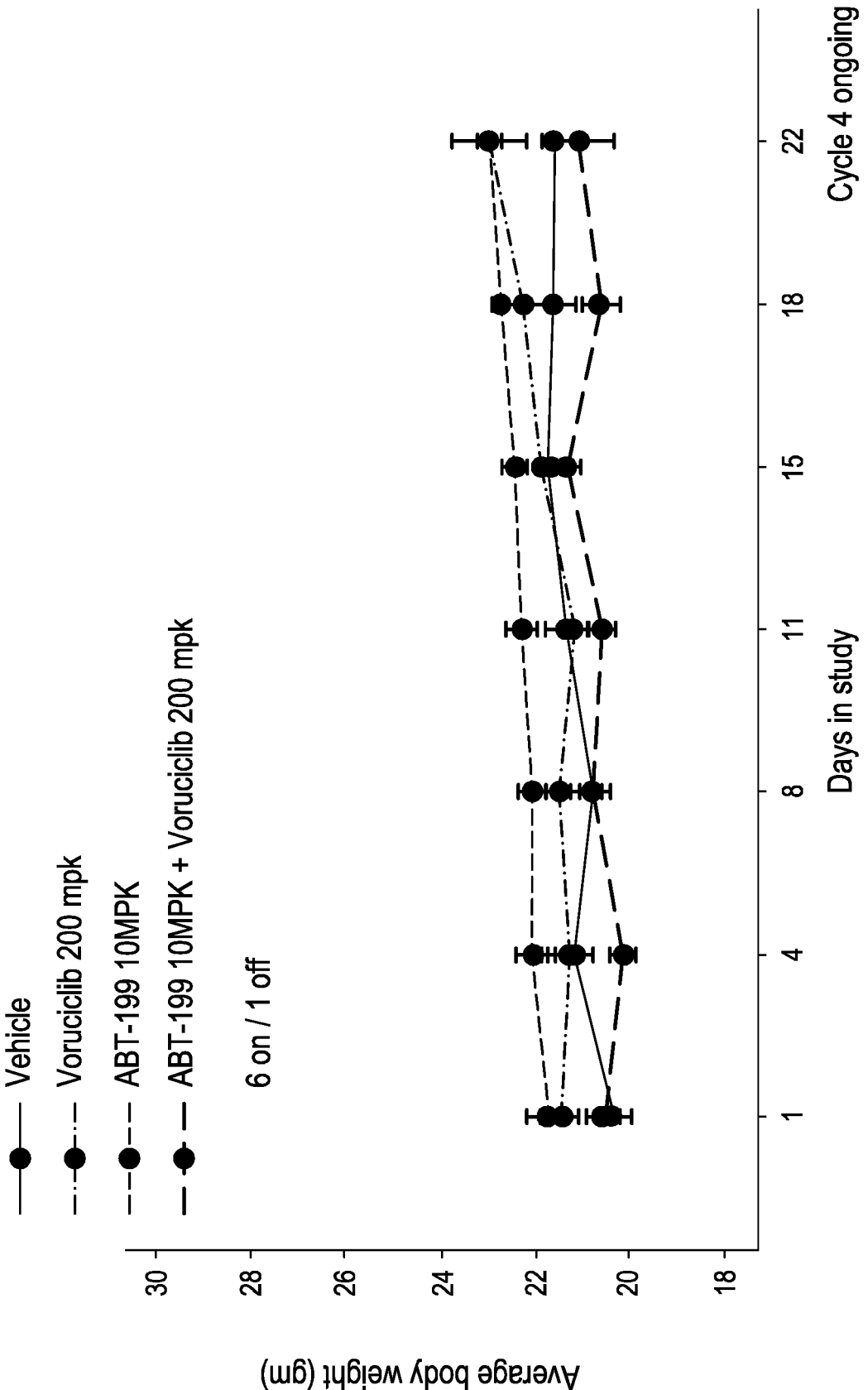

FIGS. 26A-B illustrate the combination of voruciclib and venetoclax to impede growth of DLBCL xenograft tumors. Immune deficient NOD SCID mice were implanted with the U2932 model of DLBCL. The xenografted tumors were allowed to grow in the NOD SCID host until they reached 200 mm$^3$, at which point the xenografted animals were randomized into 4 study groups: 1. Vehicle control; 2. Voruciclib at 200 mpk; 3. Venetoclax at 10 mpk; and 4. Combination of Voruciclib at 200 mpk and Venetoclax at 10 mpk. Voruciclib was dosed by oral gavage daily for 6 days of the week with a rest day in between cycles. Venetoclax was dosed by oral gavage on days 1 and 4 of each weekly cycle. Drug effects were assessed via tumor volume measurements twice weekly by a technician blinded to the treatment of each subject in the study. N=5-6 animals per treatment arm.

FIG. 26A graphs the average tumor volume (mm$^3$) for each of the 4 study groups. The single agent treatments saw a decrease in tumor volume over a longer period of study days. The combination treatment saw almost no tumor growth, with the average tumor volume staying consistent throughout the 29 day study period.

FIG. 26B graphs the average body weight in grams (g) for a subject in each of the 4 study groups. All 4 study groups showed a stable and consistent body weight, a general indication of health and safety.

Figure 27A:
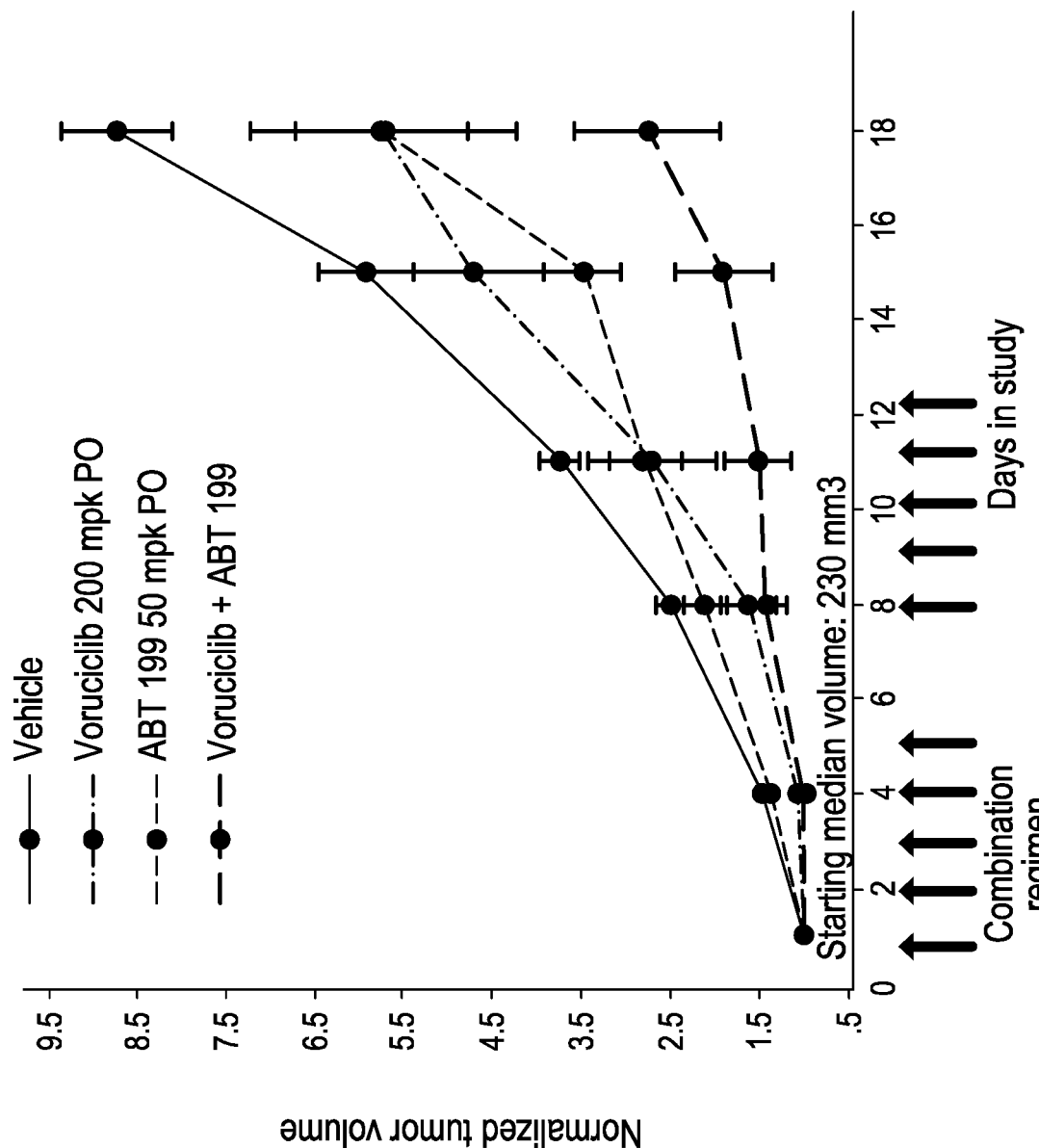
FIGS. 27A-27B illustrate the synergistic effect of voruciclib and venetoclax in NUDHL1 model of DLBCL in mice.
Figure 27B:
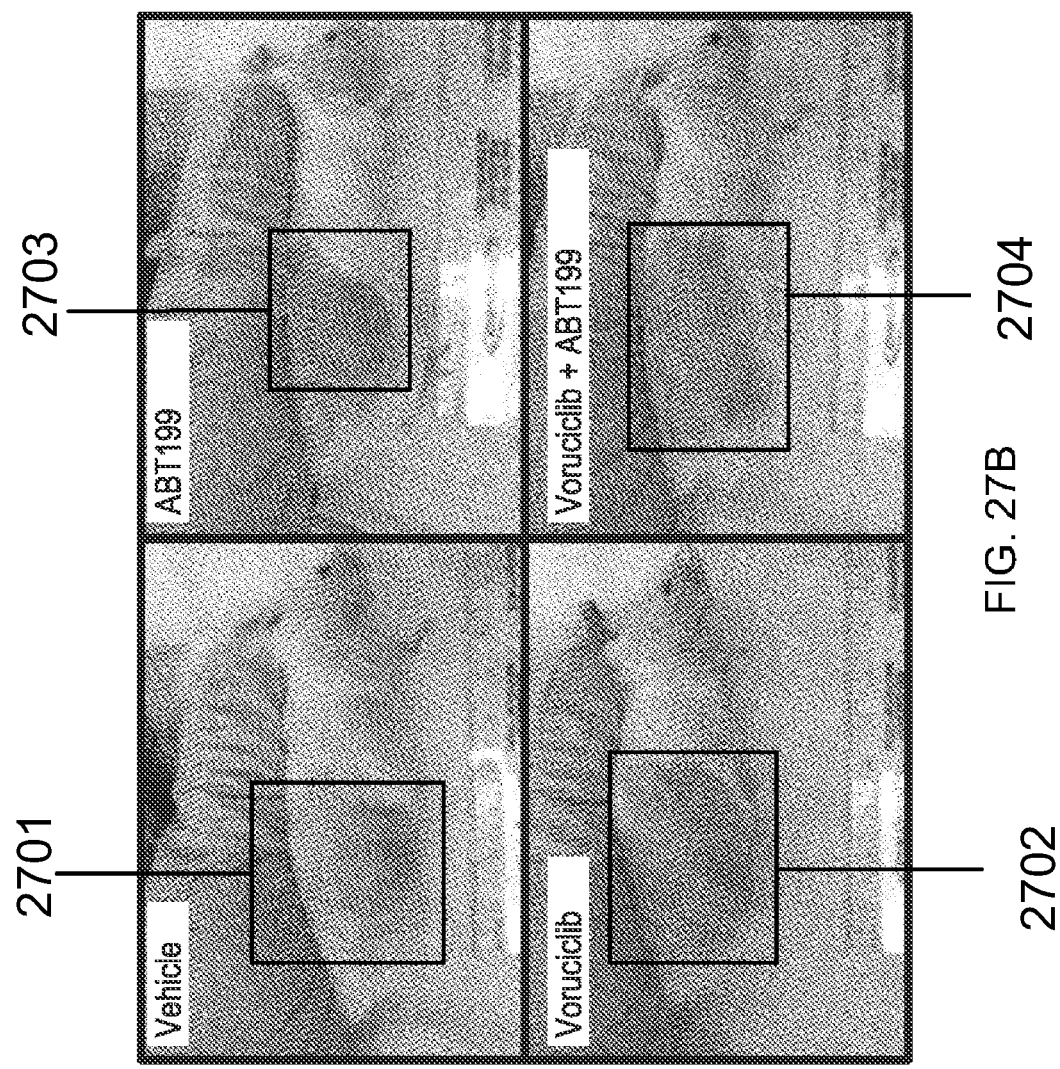

FIGS. 27A-B illustrate the combination of voruciclib and venetoclax to impede growth of DLBCL xenograft tumors. Immune deficient NOD SCID mice were implanted with the NUDHL1 model of DLBCL. The xenografted tumors were allowed to grow in the NOD SCID host until they reached 200 mm$^3$, at which point the xenografted animals were randomized into 4 study groups: 1. Vehicle control; 2. Voruciclib at 200 mpk; 3. Venetoclax at 50 mpk; and 4. Combination of Voruciclib at 200 mpk and Venetoclax at 50 mpk. Voruciclib was dosed by oral gavage daily for 6 days of the week with a rest day in between cycles. Venetoclax was dosed by oral gavage on days 1 and 4 of each weekly cycle. Drug effects were assessed via tumor volume measurements twice weekly by a technician blinded to the treatment of each subject in the study. N=5-6 animals per treatment arm.

FIG. 27A graphs the normalized tumor volume (mm$^3$) for each of the 4 study groups. The single agent treatments saw a decrease in tumor volume over a longer period of study days. The combination treatment saw a much higher decrease in tumor volume size, more than 2-fold decrease of average tumor volume by 3 weeks into the study.

FIG. 27B illustrates images of the tumors of animals from each of the 4 study groups: vehicle, single agent voruciclib, single agent venetoclax, and the combination of voruciclib and venetoclax. The vehicle tumor size was the largest, as outlined by outline 2701. The tumor of single agent voruciclib is smaller, outlined by outline 2702. The tumor of single agent venetoclax is smaller than vehicle as well, outlined by outline 2703. The combination therapy tumor is outlined by outline 2704, which is significantly smaller than that of vehicle or either of the single agent therapies, suggesting a synergistic effect.

Figure 28:
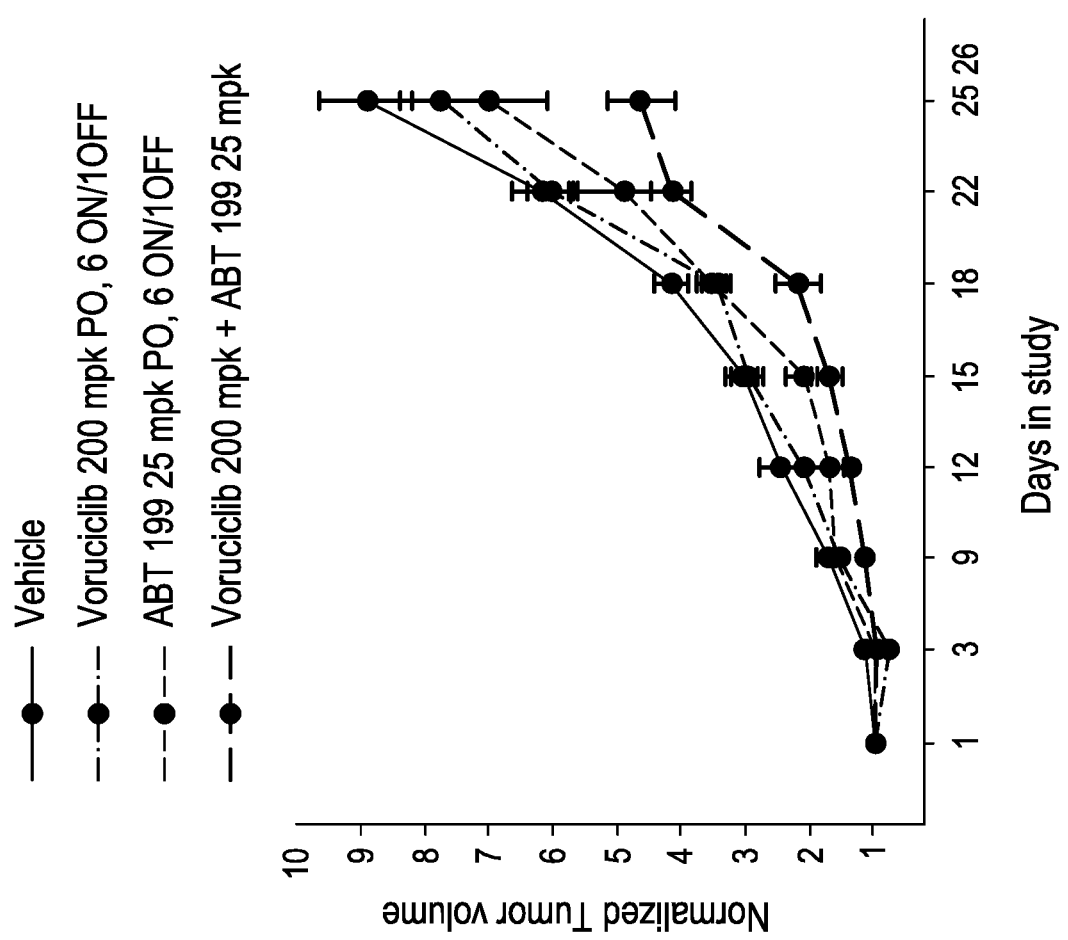
FIG. 28 illustrates the synergistic effect of voruciclib and venetoclax in SUDHL4 model of GC DLBCL.

FIG. 28 illustrates the combination of voruciclib and venetoclax to impede growth of DLBCL xenograft tumors. Immune deficient NOD SCID mice were implanted with the SUDHL4 model of DLBCL. The xenografted tumors were allowed to grow in the NOD SCID host until they reached 200 mm$^3$, at which point the xenografted animals were randomized into 4 study groups: 1. Vehicle control; 2. Voruciclib at 200 mpk; 3. Venetoclax at 25 mpk; and 4. Combination of Voruciclib at 200 mpk and Venetoclax at 25 mpk. Voruciclib was dosed by oral gavage daily for 6 days of the week with a rest day in between cycles. Venetoclax was dosed by oral gavage daily for 6 days of the week with a rest day in between cycles. Drug effects were assessed via tumor volume measurements twice weekly by a technician blinded to the treatment of each subject in the study. N=5-6 animals per treatment arm. FIG. 28 graphs the normalized tumor volume (mm$^3$) for each of the 4 study groups. The single agent treatments saw an increase in tumor volume over the study days. The combination treatment saw less tumor growth than the single agent treatments and vehicle treatment.

Figure 29:
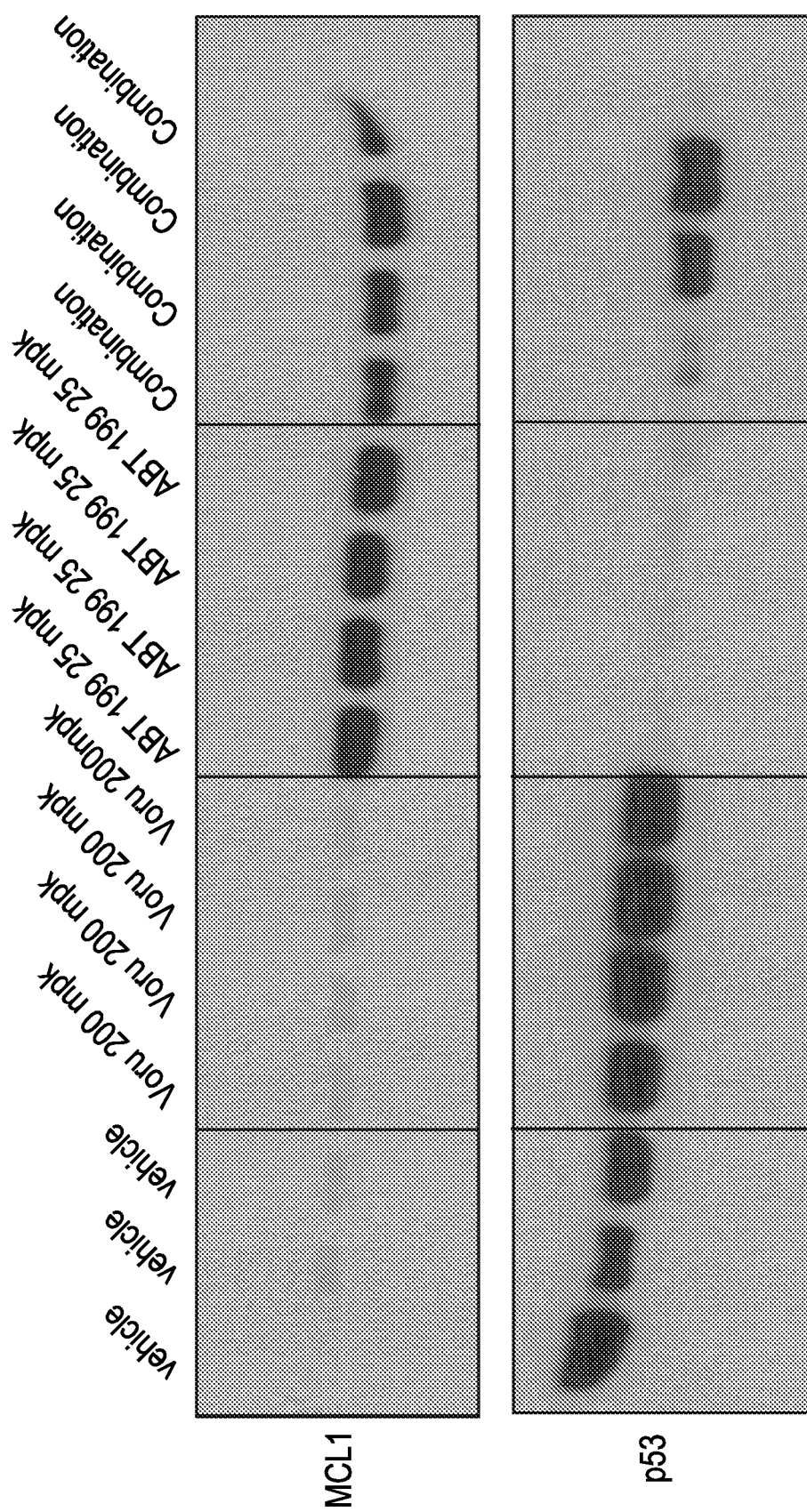
FIG. 29 illustrates that voruciclib restores p53 abrogated by venetoclax.

Each lane of FIG. 29 represents an individual SUDHL4 xenograft. Together, the Western blot illustrates that voruciclib restores p53 abrogated by venetoclax. Tumors were harvested on Day 26, 4 hours post treatment. Each tumor was fragmented into 2. One half was used for FFPE based IHC analysis, and the other half was used for Western blot analysis.

Example 13. Voruciclib Suppresses MCL1 Expression in AML Cell Lines

Figures 30A, 30B, 30C:
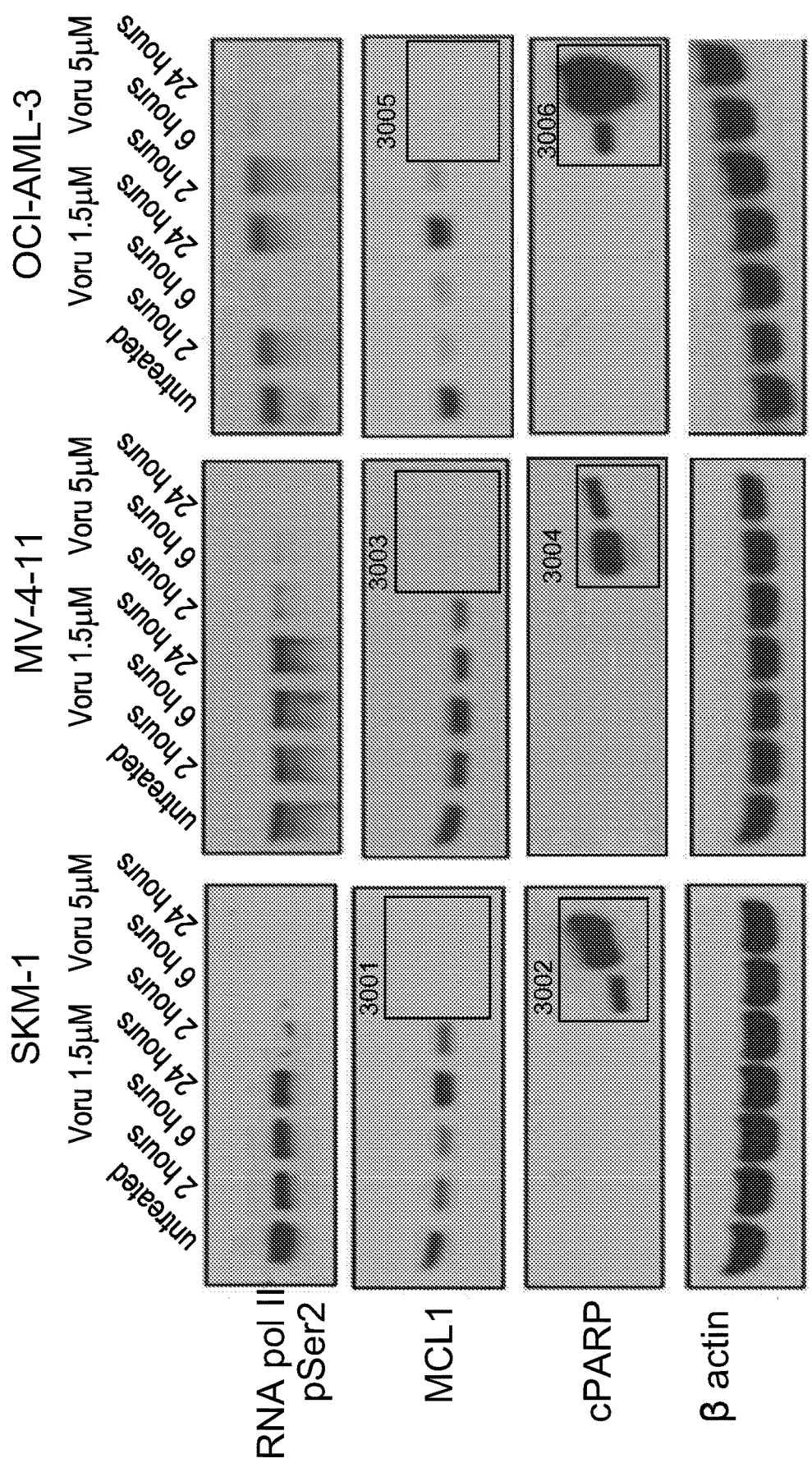
FIGS. 30A-30C illustrate that voruciclib has single agent activity in AML cell lines.

FIGS. 30A-30C illustrate that voruciclib has single agent activity in AML cell lines. AML cell lines (SKM-1, MV-4-11, and OCI-AML-3) were either left untreated of were exposed to clinically achievable levels of voruciclib (1.5 and 5.0 micromolar) for 2, 6, or 24 h. At the given time points, cells were lysed and subjected to western blot analysis with antibodies that specifically recognize phosphorylated RNA pol II (pSer2), MCL-1, cleaved PARP, and Beta-actin. In all three AML cell lines (SKM-1, MV-4-11, and OCI-AML-3), Voruciclib suppresses MCL-1 and induces apoptosis, as shown within outlines 3001, 3003, and 3005. Cleaved PARP (cPARP) may be used as a biomarker of apoptosis. In all three AML cell lines (SKM-1, MV-4-11, and OCI-AML-3), Voruciclib induces apoptosis, as shown within outlines 3002, 3004, and 3006.

Figure 31:
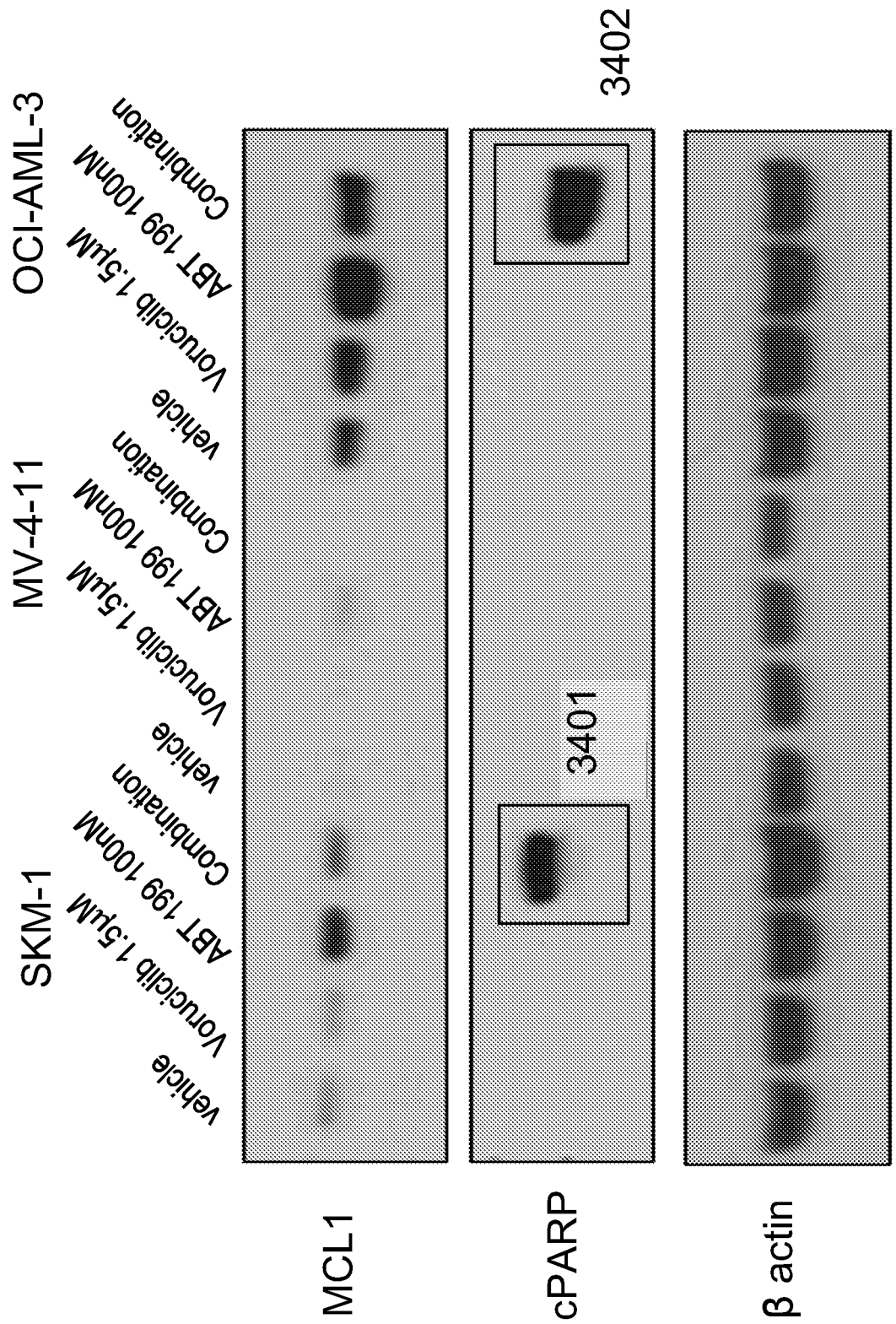
FIG. 31 illustrates that the combination of voruciclib and venetoclax induce synergistic cell death in AML cell lines.

Example 14. Voruciclib and Venetoclax Combination Induces Cell Death in AML Cell Lines FIG. 31 illustrates that the combination of voruciclib and venetoclax induce synergistic cell death in AML cell lines. AML cell lines (SKM-1, MV-4-11, and OCI-AML-3) were either left untreated of were exposed to levels of voruciclib (1.5 micromolar), venetoclax (100 nM) that were previously shown to be under the levels required to induce single agent apoptosis or the two drugs in combination at these sub-effective concentrations for 24 h. At the given time points, cells were lysed and subjected to western blot analysis with antibodies that specifically recognize phosphorylated RNA pol II (pSer2), MCL-1, cleaved PARP, and Beta-actin. As shown within the outlines 3101 and 3102, the combination of voruciclib and venetoclax induces apoptosis (PARP), when neither agent alone induces apoptosis. Venetoclax is observed to induce MCL-1 upregulation in all three cell lines. Voruciclib dampens MCL-1 driven resistance mechanism in all three cell lines.

Figure 32:
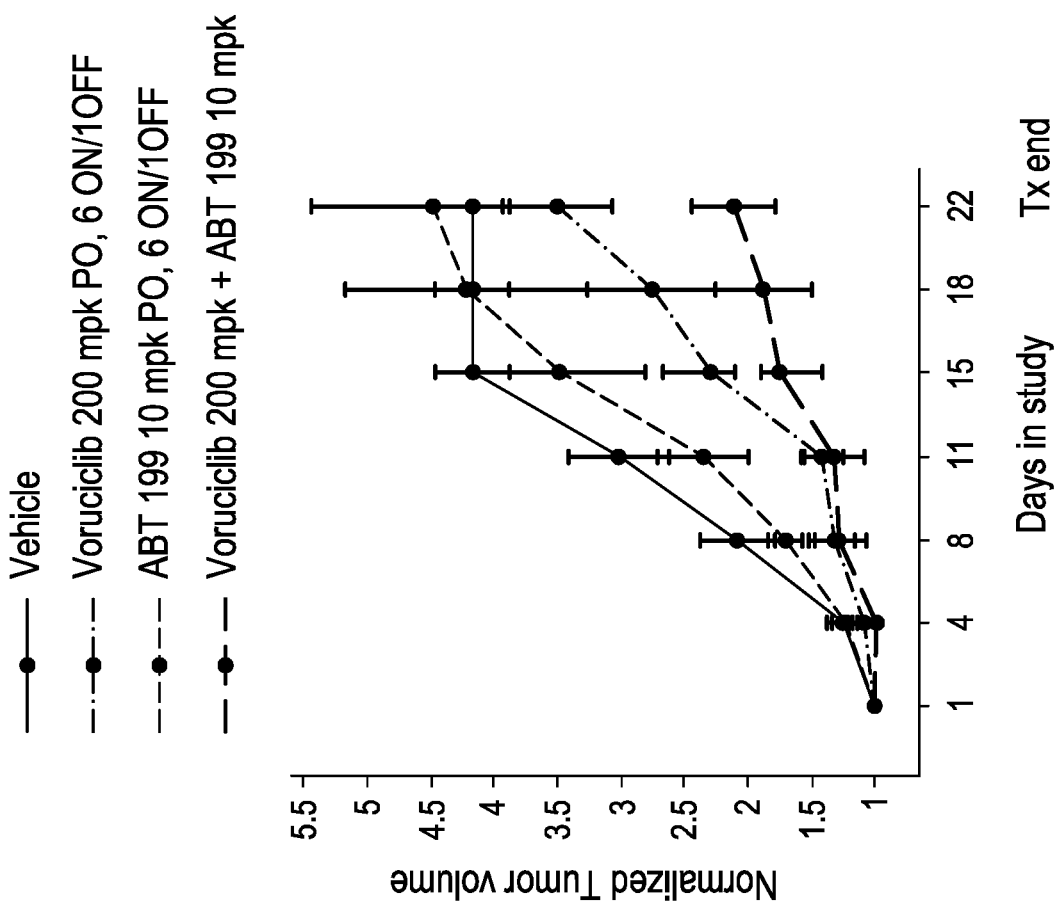
FIG. 32 illustrates the synergistic effect that the combination of voruciclib and venetoclax impedes tumor growth in SKM1 AML xenografts.

Example 15. Voruciclib and Venetoclax Combination Impedes Tumor Growth in AML Xenografts FIG. 32 illustrates that the combination of voruciclib and venetoclax impedes tumor growth in SKM1 AML xenografts. Single agent therapy of venetoclax has a normalized tumor volume similar to that of the vehicle. Voruciclib single agent treatment exhibits slightly lower tumor volume, whereas the combination of voruciclib and venetoclax greatly impedes tumor growth, with the resulting tumor volume approximately half of that of the vehicle by day 22 of the study.

Example 16. Voruciclib Induces Apoptosis as a Single Agent in DLBCL Models

Figure 33:
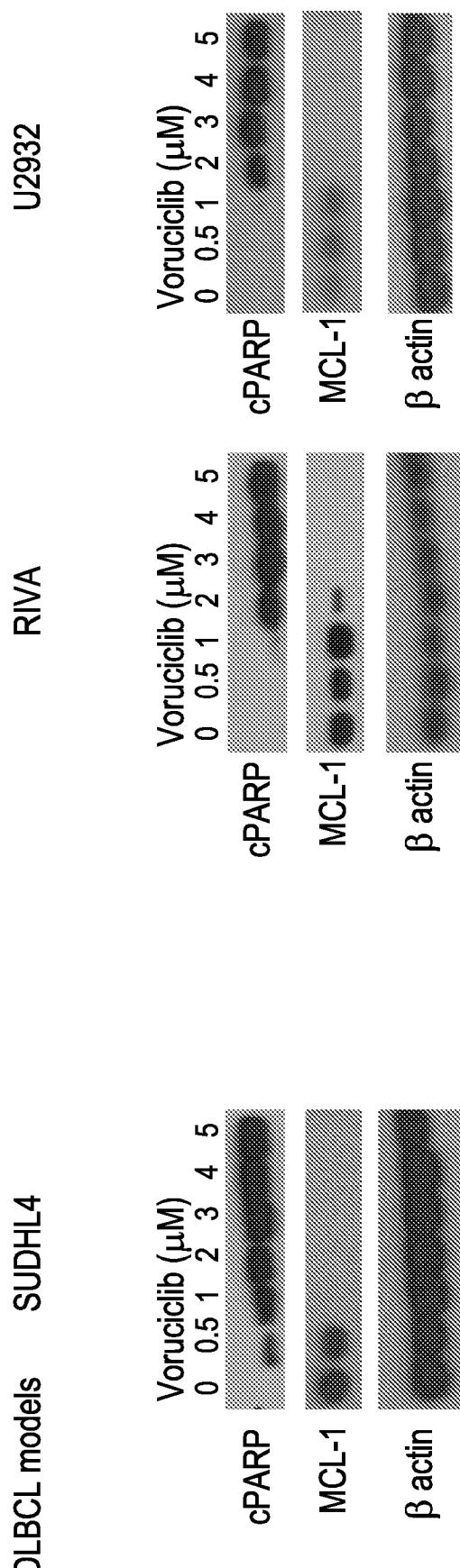
FIG. 33 illustrates that voruciclib-induced apoptosis correlates with repression of MCL.

FIG. 33 illustrates that voruciclib-induced apoptosis correlates with repression of MCL-1. Three DLBCL models were used: SUDHL4, RIvA, and U2932. Cleaved PARP (cPARP) may be used as a biomarker of apoptosis. The Western blot shows that apoptosis increases as the concentration of voruciclib increases. Similarly, voruciclib suppresses MCL-1 and induces apoptosis as the concentration of voruciclib increases.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical composition comprising a therapeutically effective amount of a CDK inhibitor represented by Formula Ib:

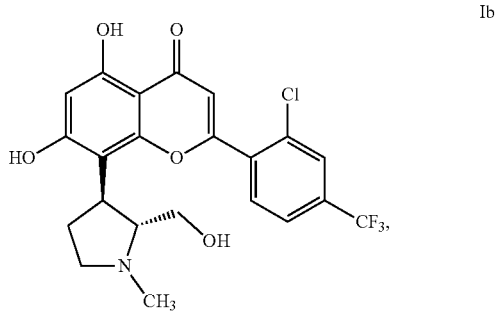 [SMILES: CN1CC[C@@H](c2c(O)cc(O)c3c(=O)cc(-c4ccc(C(F)(F)F)cc4Cl)oc23)[C@@H]1CO]

or a pharmaceutically acceptable salt thereof, a therapeutically effective amount of venetoclax or a pharmaceutically acceptable salt thereof, and a pharmaceutically acceptable excipient.

2. The pharmaceutical composition of claim 1, wherein the CDK inhibitor or a pharmaceutically acceptable salt thereof is (+)-trans-2-(2-chloro-4-trifluoromethylphenyl)-5,7-dihydroxy-8-(2-hydroxymethyl-1-methyl-pyrrolidin-3-yl)-chromen-4-one hydrochloride.

3. A pharmaceutical kit for the treatment of a blood cancer, the kit comprising:
   1) a therapeutically effective amount of a CDK inhibitor represented by Formula Ib:

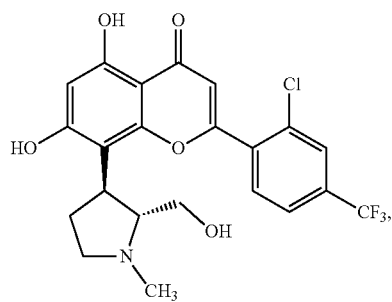

Ib or a pharmaceutically acceptable salt thereof, and
   2) a package insert, wherein the package insert comprises instructions for administering the CDK inhibitor, or a pharmaceutically acceptable salt thereof, in combination with a therapeutically effective amount of venetoclax or a pharmaceutically acceptable salt thereof.

4. The kit of claim 3, wherein the blood cancer is selected from acute myeloid leukemia (AML), chronic myeloid leukemia (CML), acute lymphocytic lymphoma (ALL), and chronic lymphocytic leukemia (CLL), diffuse large B-cell lymphoma (DLBCL), primary mediastinal B-cell lymphoma, intravascular large B-cell lymphoma, follicular lymphoma, small lymphocytic lymphoma (SLL), mantle cell lymphoma, marginal zone B-cell lymphomas, extranodal marginal zone B-cell lymphomas, nodal marginal zone B-cell lymphoma, splenic marginal zone B-cell lymphoma, Burkitt lymphoma, lymphoplasmacytic lymphoma, and primary central nervous system lymphoma.

5. The kit of claim 4, wherein the blood cancer is diffuse large B-cell lymphoma, acute myeloid leukemia or chronic lymphocytic leukemia.

6. The kit of claim 3, wherein the package insert comprises instructions for concurrently administering the CDK inhibitor or a pharmaceutically acceptable salt thereof and venetoclax or a pharmaceutically acceptable salt thereof to a subject in need thereof.

7. The kit of claim 3, wherein the package insert comprises instructions for sequentially administering the CDK inhibitor or a pharmaceutically acceptable salt thereof and venetoclax or a pharmaceutically acceptable salt thereof to a subject in need thereof.

8. The kit of claim 7, wherein the package insert comprises instructions for sequentially administering the CDK inhibitor or a pharmaceutically acceptable salt thereof and venetoclax or a pharmaceutically acceptable salt thereof within about 12 hours of each other to a subject in need thereof.

9. The kit of claim 7, wherein the package insert comprises instructions for sequentially administering the CDK inhibitor or a pharmaceutically acceptable salt thereof and venetoclax or a pharmaceutically acceptable salt thereof within about 5 hours of each other to a subject in need thereof.

10. The kit of claim 3, wherein the package insert comprises instructions for administering the CDK inhibitor or a pharmaceutically acceptable salt thereof and venetoclax or a pharmaceutically acceptable salt thereof daily, every other day, or every third day to a subject in need thereof.

11. The kit of claim 3, wherein the CDK inhibitor or a pharmaceutically acceptable salt thereof is (+)-trans-2-(2-chloro-4-trifluoromethylphenyl)-5,7-dihydroxy-8-(2-hydroxymethyl-1-methyl-pyrrolidin-3-yl)-chromen-4-one hydrochloride.

* * * * *